US010933056B2

(12) United States Patent
Acton, III et al.

(10) Patent No.: US 10,933,056 B2
(45) Date of Patent: *Mar. 2, 2021

(54) 3-(1H-PYRAZOL-4-YL)PYRIDINE ALLOSTERIC MODULATORS OF THE M4 MUSCARINIC ACETYLCHOLINE RECEPTOR

(71) Applicants: Merck Sharp & Dohme Corp., Rahway, NJ (US); MSD R&D (CHINA) CO., LTD., Shanghai (CN)

(72) Inventors: John J. Acton, III, Cranford, NJ (US); Jianming Bao, South San Francisco, CA (US); Melissa Egbertson, Ambler, PA (US); Xiaolei Gao, Bridgewater, NJ (US); Scott T. Harrison, Elkins Park, PA (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Zhaoyang Meng, Ambler, PA (US); Michael T. Rudd, Collegeville, PA (US); Oleg B. Selyutin, West Windsor, NJ (US); David M. Tellers, Lansdale, PA (US); Ling Tong, Warren, NJ (US); Jenny Miu-Chun Wai, Harleysville, PA (US)

(73) Assignees: Merck Sharp & Dohme Corp., Rahway, NJ (US); MSD R&D (China) Co. Ltd., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/674,546

(22) Filed: Nov. 5, 2019

(65) Prior Publication Data

US 2020/0069671 A1  Mar. 5, 2020

Related U.S. Application Data

(63) Continuation of application No. 16/062,500, filed as application No. PCT/US2016/067419 on Dec. 19, 2016, now Pat. No. 10,512,638.

(30) Foreign Application Priority Data

Dec. 23, 2015 (WO) ............... PCT/CN2015/098384

(51) Int. Cl.
| | |
|---|---|
| C07D 401/14 | (2006.01) |
| C07D 405/14 | (2006.01) |
| C07D 471/04 | (2006.01) |
| A61K 31/4439 | (2006.01) |
| A61P 25/28 | (2006.01) |
| A61P 25/18 | (2006.01) |
| A61P 25/16 | (2006.01) |
| A61K 31/437 | (2006.01) |

(52) U.S. Cl.
CPC ........ *A61K 31/4439* (2013.01); *A61K 31/437* (2013.01); *A61P 25/16* (2018.01); *A61P 25/18* (2018.01); *A61P 25/28* (2018.01); *C07D 401/14* (2013.01); *C07D 405/14* (2013.01); *C07D 471/04* (2013.01)

(58) Field of Classification Search
CPC .... C07D 401/14; A61K 31/4439; A61P 25/28
USPC ...................................................... 514/300
See application file for complete search history.

(56) References Cited

U.S. PATENT DOCUMENTS

| | | |
|---|---|---|
| 5,574,044 A | 11/1996 | Thompson et al. |
| 5,691,323 A | 11/1997 | Thompson et al. |
| 6,699,880 B1 | 3/2004 | Yamakawa et al. |
| 6,900,224 B2 | 5/2005 | Ledoussal et al. |
| 7,074,801 B1 | 7/2006 | Yoshida et al. |
| 7,858,635 B2 | 12/2010 | Makings et al. |
| 7,964,602 B2 | 6/2011 | MacDonald et al. |
| 8,071,776 B2 | 12/2011 | Rubio Esteban et al. |
| 8,168,639 B2 | 5/2012 | Kogan |
| 8,349,850 B2 | 1/2013 | Tworowski et al. |
| 8,614,319 B2 | 12/2013 | Tworowski et al. |
| 9,034,872 B2 | 5/2015 | Tworowski et al. |
| 9,056,875 B2 | 6/2015 | Lindsley et al. |
| 9,056,876 B2 | 6/2015 | Conn et al. |
| 9,493,481 B2 | 11/2016 | Lindsley et al. |
| 9,593,106 B2 | 3/2017 | Livermore et al. |
| 9,637,498 B2 | 5/2017 | Lindsley et al. |
| 9,670,183 B2 | 6/2017 | Brown et al. |
| 9,758,506 B2 | 9/2017 | Brown et al. |
| 9,868,746 B2 | 1/2018 | Lindsley et al. |
| 10,512,638 B2 | 12/2019 | Rudd et al. |

(Continued)

FOREIGN PATENT DOCUMENTS

| | | |
|---|---|---|
| CN | 102015655 | 4/2011 |
| JP | 2014047192 | 3/2014 |

(Continued)

OTHER PUBLICATIONS

Bymaster FB et al , Role of cholinergic muscarine system in bipolar disorder and related mechanism of action of antipsychotic agents. (Year: 2002).*

(Continued)

*Primary Examiner* — Rita J Desai
(74) *Attorney, Agent, or Firm* — J. Eric Thies; John C. Todaro

(57) ABSTRACT

The present invention is directed to pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

11 Claims, No Drawings

(56) References Cited

U.S. PATENT DOCUMENTS

| | | | |
|---|---|---|---|
| 2007/0004763 | A1 | 1/2007 | Baindur et al. |
| 2008/0306107 | A1 | 12/2008 | Griffin et al. |
| 2012/0202784 | A1 | 8/2012 | Aronov et al. |
| 2013/0096144 | A1 | 4/2013 | Huang et al. |
| 2014/0288084 | A1 | 9/2014 | Lindsley et al. |
| 2015/0307451 | A1 | 10/2015 | Yamada et al. |
| 2015/0307479 | A1 | 10/2015 | Kuduk et al. |
| 2015/0307497 | A1 | 10/2015 | Sugimoto et al. |
| 2016/0200733 | A1 | 7/2016 | Lindsley et al. |
| 2017/0096437 | A1 | 4/2017 | Congreve et al. |
| 2017/0369505 | A1 | 12/2017 | Lindsley et al. |

FOREIGN PATENT DOCUMENTS

| | | |
|---|---|---|
| WO | WO2005100351 | 10/2005 |
| WO | WO2006/125180 | 11/2006 |
| WO | WO2011087776 | 7/2011 |
| WO | WO2012020813 | 2/2012 |
| WO | WO2013055895 | 4/2013 |
| WO | WO2013056015 | 4/2013 |
| WO | WO2014/035829 | 3/2014 |
| WO | WO2014101373 | 7/2014 |
| WO | WO2016/147011 | 9/2016 |
| WO | WO2017/021728 | 2/2017 |
| WO | WO2017/077292 | 5/2017 |
| WO | WO2017/107087 | 6/2017 |

OTHER PUBLICATIONS

Bewley, Blake R., et al., Discovery of a novel, CNS penetrant M4PAM chemotype based on a 6-fluoro-4-(piperiden-1-yl)quinoline-3-carbonitrile core, Bioorganic and Med Chem Letters, 2017, 4274-4279, 27.

Byun, Nellie B, et al., Antipsychotic Drug-like Effects of the Selective M4 Muscarinic Acetylcholine Receptor Positive Allosteric Modulator VU02552100, Neuropsychopharmacology, 2014, 1578-1593, 39.

Eglen, Richard M., Muscarinic receptor ligands and their therapeutic potential, Current Opinion in Chemical Biology, 1999, 426-432, 3.

Kargbo, Robert B., Allosteric Modulators of the M4 Muuscarinic Acetylcholine Receptor, ACS Medicinal Chemistry Letters, 2017, 903-904, 8.

Lindsley, Craig W., et al., Discovery of the mAChR subtype selective M4 positive allosteric moduclators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VU0476406, a non-human primate in vivo tool compound for translational pharmacology, Bioorganic and Med Chem Letters, 2017, 2296-2301, 27.

Salovich, James M., et al., Discovery of N-(4-methoxy-7-methylbenzo[d]thiazol-2-yl) . . . , Bioorganic and Med Chem Letters, 2012, 5084-5088, 22.

Tarr, James C., Challenges in the development of an M4PAM preclinical candidate: The discovery, SAR and in vivo characterization of a . . . , Bioorganic and Med Chem Letters, 2017, 2990-2995, 27.

Tarr, James C., et al., Challenges in the development of an M4PAM Preclinical candidate: . . . , Bioorganic and Med Chem Letters, 2017, 5179-5184, 27.

Utley, Thomas, Synthesis and SAR of a novel metabotropic glutamate receptor 4 . . . , Bioorganic and Med Chem Letters, 2011, 6955-6959, 21.

Wood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

European Search Report, EP 20190356.4, dated Oct. 9, 2020, 9 pages.

U.S. Appl. No. 16/062,500, filed Jun. 14, 2018.

* cited by examiner

3-(1H-PYRAZOL-4-YL)PYRIDINE ALLOSTERIC MODULATORS OF THE M4 MUSCARINIC ACETYLCHOLINE RECEPTOR

CROSS REFERENCE TO RELATED APPLICATIONS

This application is a Continuation of application Ser. No. 16/062,500, filed Jun. 14, 2018, which is a U.S. National Phase application under 35 U.S.C. § 371 of PCT Application No. PCT/US2016/067419, filed Dec. 19, 2016, which claims priority from PCT Application No. PCT/CN2015/098384, filed Dec. 23, 2015.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

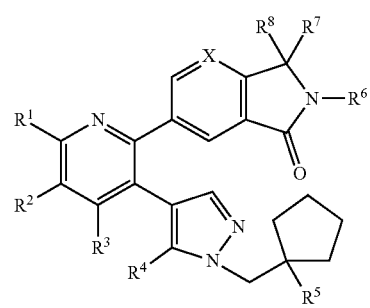

I wherein:

X is N or CH;

R¹ is selected from the group consisting of:
(1) hydrogen,
(2) halogen,
(3) —CN,
(4) —$C_{1-6}$alkyl, which is unsubstituted or substituted with a hydroxy, or 1-3 fluoro,
(5) —O—$C_{1-6}$alkyl, which is unsubstituted or substituted with a hydroxy, or 1-3 fluoro,
(6) —C≡CH,
(7) —(C=O)—NH₂, and
(8) —(C=O)—NH(—$C_{1-6}$alkyl);

R² is selected from the group consisting of:
(1) hydrogen,
(2) halogen,
(3) —$C_{1-6}$alkyl, and
(4) —NH₂,
or R¹ and R² are joined together with a —(CH₂)₃— or —(C=O)(CH₂)₂— to form a 5-membered ring, which is unsubstituted or substituted with a hydroxy, or 1-3 fluoro,
or R¹ and R² are joined together with a —(CH₂)₄—, —(C=O)(CH₂)₃—, or —(CH₂)(C=O)(CH₂)₂— to form a 6-membered ring, which is unsubstituted or substituted with a hydroxy, or 1-3 fluoro;

R³ is selected from the group consisting of:
(1) hydrogen,
(2) halogen,
(3) —CN,
(4) —$C_{1-6}$alkyl, and
(5) —NH₂;

R⁴ is selected from the group consisting of:
(1) hydrogen,
(2) —CN,
(3) chloro, and
(4) fluoro;

R⁵ is selected from the group consisting of:
(1) hydrogen, and
(2) —CH₃;

R⁶ is selected from the group consisting of:
(1) hydrogen,
(2) —$C_{1-6}$alkyl, which is unsubstituted or substituted with a —CN, 1-3 fluoro, or phenyl which is unsubstituted or substituted with a hydroxy or a —SO₂—NH₂,
(3) —$C_{3-6}$cycloalkyl, which is unsubstituted or substituted with a —CN, or —(C=O)—NH₂;
(4) —(CH$_{2-5}$cycloalkyl-O—),
(5) —$C_{1-6}$alkyl-$C_{3-6}$cycloalkyl,
(6) —$C_{1-6}$alkyl-(CH$_{2-5}$cycloalkyl-O—),
(7) —$C_{1-6}$alkyl-O—$C_{1-6}$alkyl,
(8) —$C_{1-6}$alkyl-C≡CH,
(9) —$C_{1-6}$alkyl-C≡C—$C_{1-6}$alkyl, and
(10) phenyl;

each of R⁷ and R⁸ is independently selected from the group consisting of:
(1) hydrogen, and
(2) $C_{1-6}$alkyl,
or R⁷ and R⁸ taken together form a keto group;
or a pharmaceutically acceptable salt thereof.

An embodiment of the present invention includes compounds of the formula Ia:

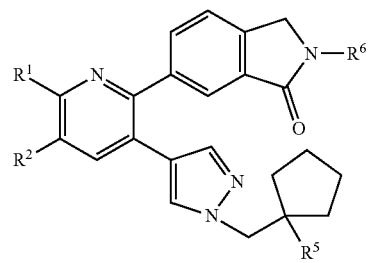

Ia wherein R¹, R², R⁵ and R⁶ are defined herein; or a pharmaceutically acceptable salt thereof.

An embodiment of the present invention includes compounds of the formula Ib:

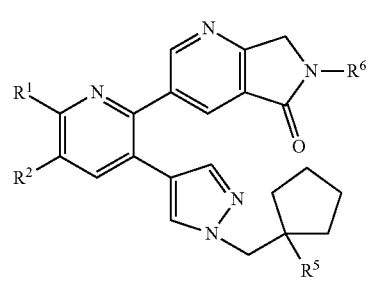

Ib wherein R¹, R², R⁵ and R⁶ are defined herein; or a pharmaceutically acceptable salt thereof.

An embodiment of the present invention includes compounds wherein X is N. An embodiment of the present invention includes compounds wherein X is CH.

An embodiment of the present invention includes compounds wherein R¹ is selected from the group consisting of:
(1) hydrogen,
(2) fluoro,
(3) chloro,
(4) —CN, and
(5) methyl.

An embodiment of the present invention includes compounds wherein R¹ is selected from the group consisting of:
(1) hydrogen,
(2) —CN, and
(3) methyl.

An embodiment of the present invention includes compounds wherein R² is selected from the group consisting of:
(1) hydrogen, and
(2) methyl.

An embodiment of the present invention includes compounds R¹ and R² are joined together with a —(CH₂)₃— to form a 5-membered ring, which is unsubstituted or substituted with a hydroxy, or 1-3 fluoro.

An embodiment of the present invention includes compounds R¹ and R² are joined together with a —(C=O)(CH₂)₂— to form a 5-membered ring, which is unsubstituted or substituted with a hydroxy, or 1-3 fluoro.

An embodiment of the present invention includes compounds wherein R³ is selected from the group consisting of:
(1) hydrogen,
(2) —CN, and
(2) methyl.

An embodiment of the present invention includes compounds wherein $R^3$ is hydrogen.

An embodiment of the present invention includes compounds wherein $R^4$ is hydrogen. An embodiment of the present invention includes compounds wherein $R^4$ is cyano.

An embodiment of the present invention includes compounds wherein $R^4$ is fluoro.

An embodiment of the present invention includes compounds wherein $R^5$ is hydrogen. An embodiment of the present invention includes compounds wherein $R^5$ is methyl.

An embodiment of the present invention includes compounds wherein $R^6$ is selected from the group consisting of:
(1) hydrogen,
(2) —$C_{1-6}$alkyl, which is unsubstituted or substituted with a —CN, 1-3 fluoro, or phenyl which is unsubstituted or substituted with a hydroxy or a —$SO_2$—$NH_2$,
(3) —$C_{3-6}$cycloalkyl, which is unsubstituted or substituted with a —CN, or —(C=O)—$NH_2$;
(4) —($CH_{2-5}$cycloalkyl-O—),
(5) —$C_{1-6}$alkyl-$C_{3-6}$cycloalkyl,
(6) —$C_{1-6}$alkyl-O—$C_{1-6}$alkyl,
(7) —$C_{1-6}$alkyl-C≡CH, and
(8) —$C_{1-6}$alkyl-C≡C—$C_{1-6}$alkyl.

An embodiment of the present invention includes compounds wherein $R^6$ is selected from the group consisting of:
(1) hydrogen,
(2) —$C_{1-6}$alkyl, which is unsubstituted or substituted with a —CN, 1-3 fluoro, or phenyl which is unsubstituted or substituted with a hydroxy or a —$SO_2$—$NH_2$, and
(3) —$C_{1-6}$alkyl-$C_{3-6}$cycloalkyl.

An embodiment of the present invention includes compounds wherein $R^6$ is selected from the group consisting of:
(1) —$C_{1-6}$alkyl, which is unsubstituted or substituted with a —CN, 1-3 fluoro, and
(2) —$C_{1-6}$alkyl-$C_{3-6}$cycloalkyl.

An embodiment of the present invention includes compounds wherein $R^6$ is methyl. An embodiment of the present invention includes compounds wherein $R^6$ is —$CH_2$-cyclopropyl.

An embodiment of the present invention includes compounds wherein $R^7$ is hydrogen and $R^8$ is hydrogen. An embodiment of the present invention includes compounds wherein $R^7$ and $R^8$ taken together form a keto group.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Similarly, ($CH_{2-5}$cycloalkyl-O—) indicates the presence of cyclopropoxy, cyclobutoxy, tetrahydrofuranyl, or tetrahydropyranyl ring. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}C$ isotope. An embodiment of the present invention includes compounds that are substituted with an $^{18}F$ isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and *Mol Pharmacol*, 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 1000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 μM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, 0-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (+)-2,3-dihydro-5, 6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK3β inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B 1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DAST: diethylaminosulfur trifluoride; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMSO: dimethylsulfoxide; dppf: 1,1'-bis(diphenylphosphino)ferrocene; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; mCPBA: meta-chloroperbenzoic acid; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; NCS: N-chlorosuccinimide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; TBAF: tetra-n-butylammonium fluoride; TFA: trifluoroacetic acid; TFAA: trifluoroacetic anhydride; THF: tetrahydrofuran; TIPS: triisopropylsilyl; TLC: thin layer chromatography; Ts: toluenesulfonyl; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

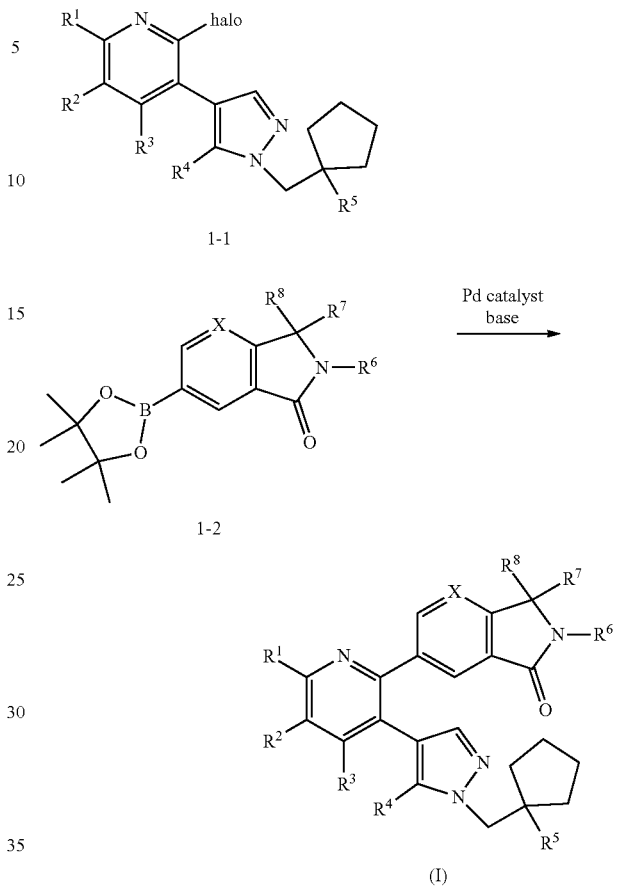

Compounds of formula (I) are synthesized from a palladium-catalyzed Suzuki coupling reaction of prepared intermediate halide 1-1 and a prepared or known boronic ester or acid 1-2. In some cases where there is the stereocenter present, an additional chiral resolution may be carried out to provide enantiomeric products.

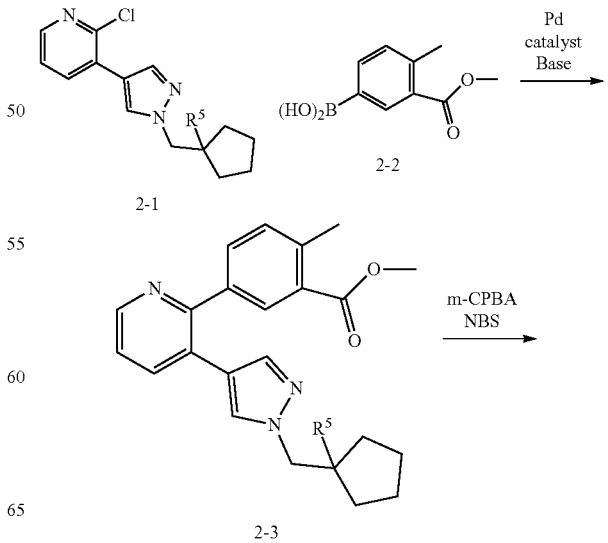

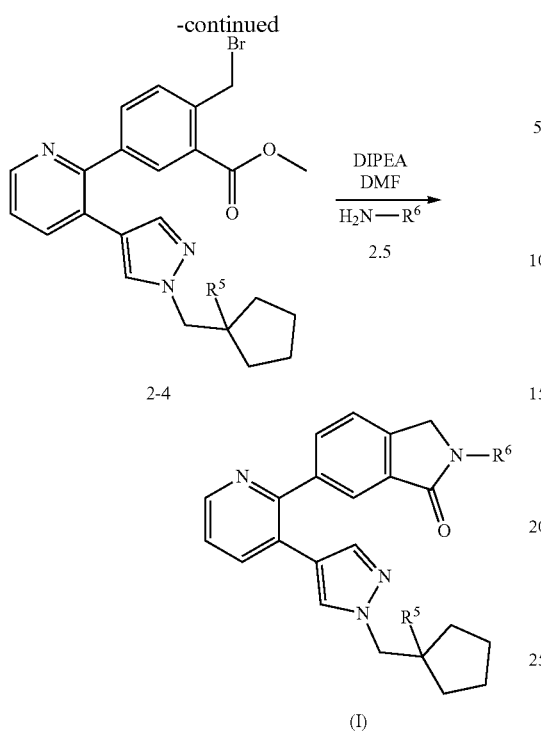

Compounds of formula (I) are prepared from reaction sequence that begins with Suzuki coupling reaction mediated by palladium catalyst of prepared intermediate halide 2-1 and commercial boronic acid 2-2. A radical bromination of tolyl-intermediate 2-3 provides the penultimate benzyl bromide 2-4. Condensation of 2-4 with amines provides compounds of the formula (I).

SCHEME 3

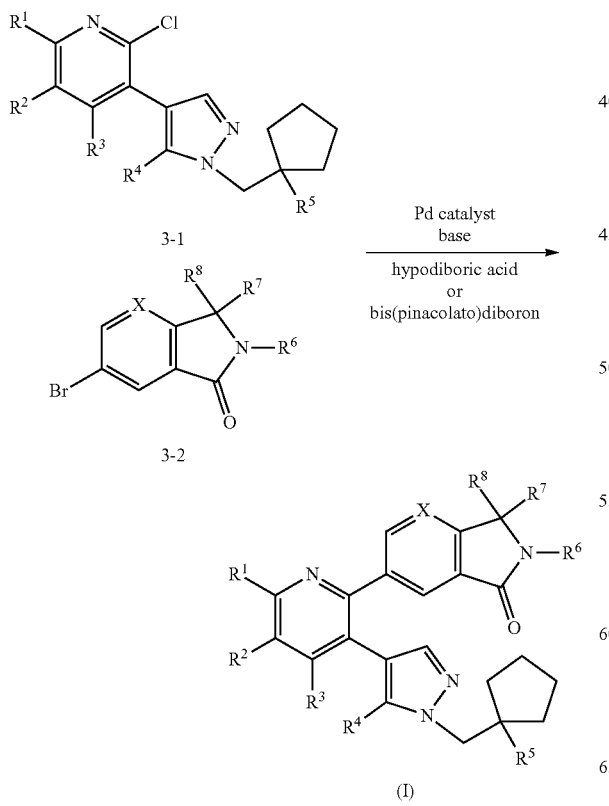

Compounds of formula (I) are prepared from a 2-step, 1-pot protocol for the in situ formation of a boronic ester or acid of bromide 3-2 that undergoes a subsequent Suzuki coupling reaction mediated by palladium catalysts.

SCHEME 4

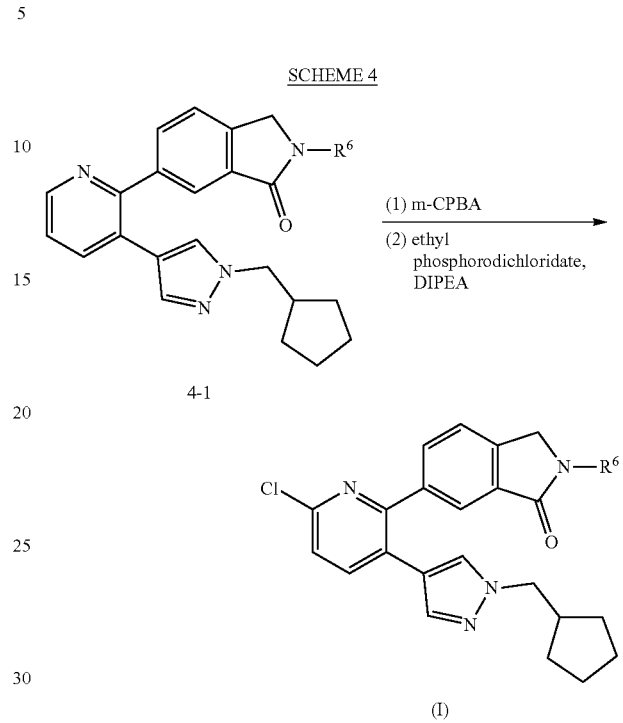

Compounds of formula (I) are prepared from a 2-step protocol that forms an N-oxide intermediate from the corresponding pyridine 4-1. Subsequent exposure to a chlorinating reagent yield compounds of the formula (I).

SCHEME 5

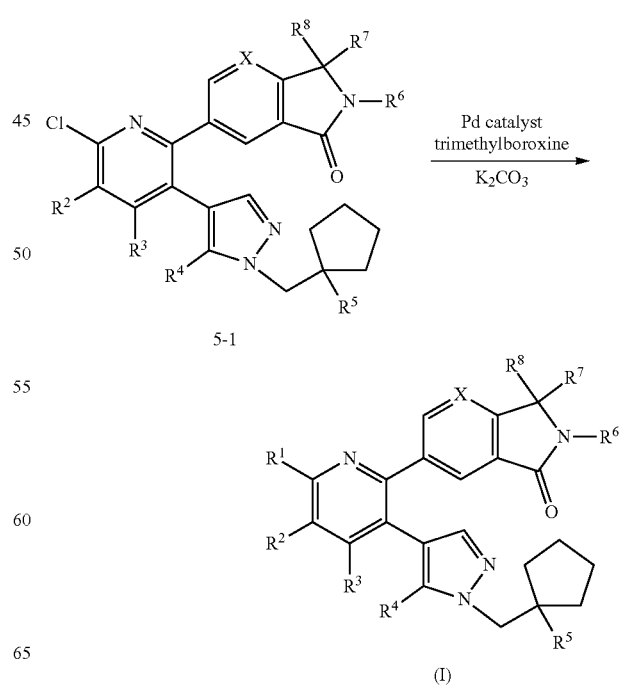

Compounds of formula (I) are prepared via a palladium-mediated Suzuki coupling reaction of a prepared halopyridine 5-1 with trimethylboroxine.

SCHEME 6

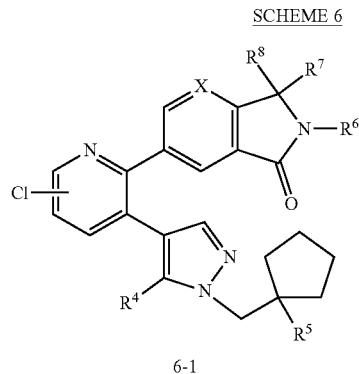

6-1

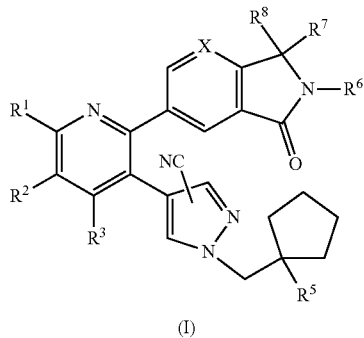

(I)

Compounds of formula (I) are prepared via a palladium-catalyzed Negishi coupling reaction of prepared chloropyridine 6-1 or chloropyrazole 6-2 with zinc cyanide.

SCHEME 7

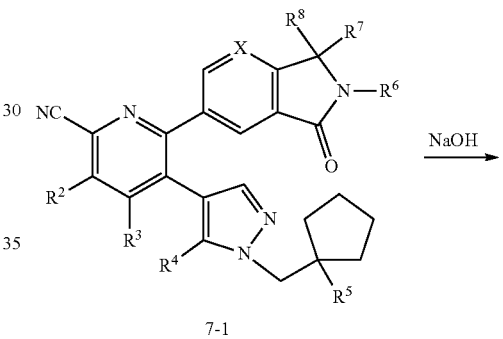

7-1

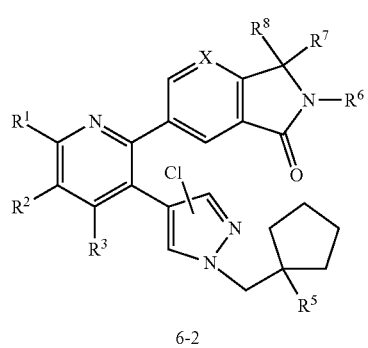

6-2

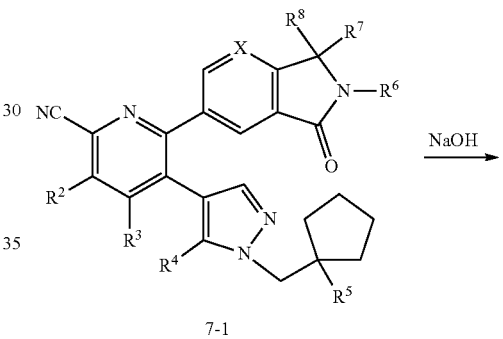

(I)

Compounds of formula (I) are prepared via nitrile hydrolysis of a prepared nitrile 7-1 to the corresponding carboxamide.

SCHEME 8

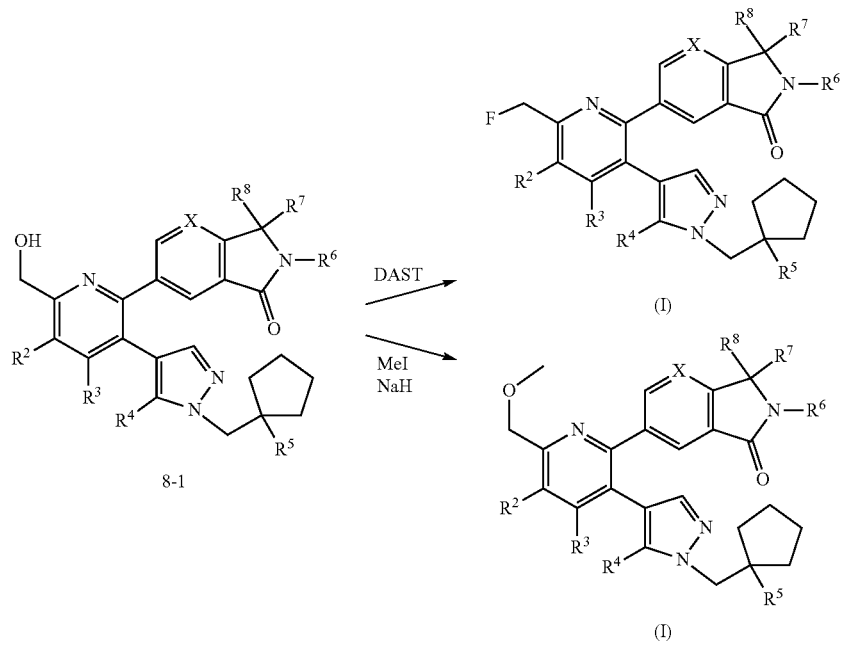

Compounds of formula (I) are prepared according to Scheme 8 from a prepared alcohol 8-1 through either exposure to a fluorinating agent or alkylation conditions with alkyl halides to form the corresponding fluoride or methyl ether, respectively.

SCHEME 9

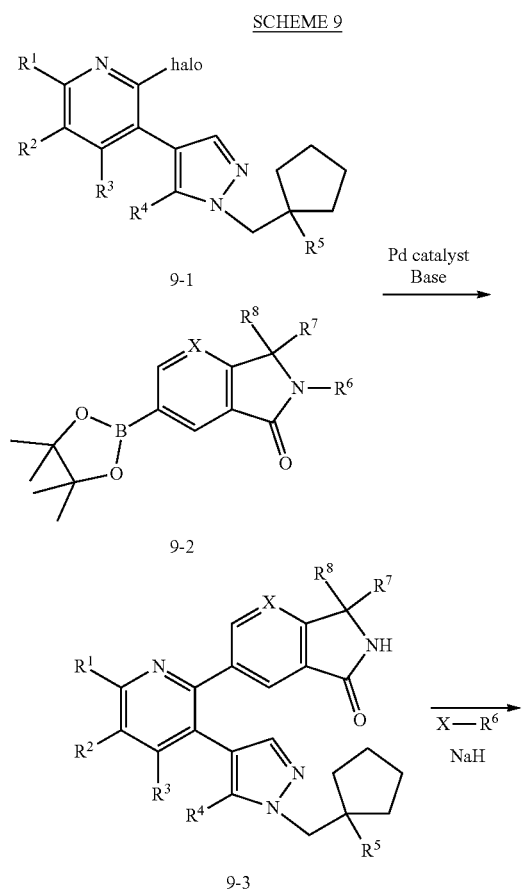

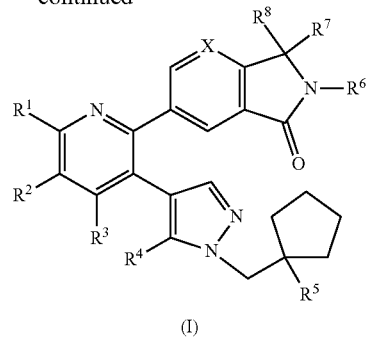

Compounds of formula (I) are synthesized according to scheme 9 commencing with a palladium-mediated Suzuki coupling reaction of a prepared halopyridine 9-1 with a known or prepared boronic ester or acid 9-2. Subsequent alkylation of the lactam 9-3 with a commercial alkylhalide provides compounds of formula (I).

SCHEME 10

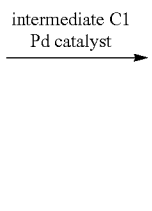

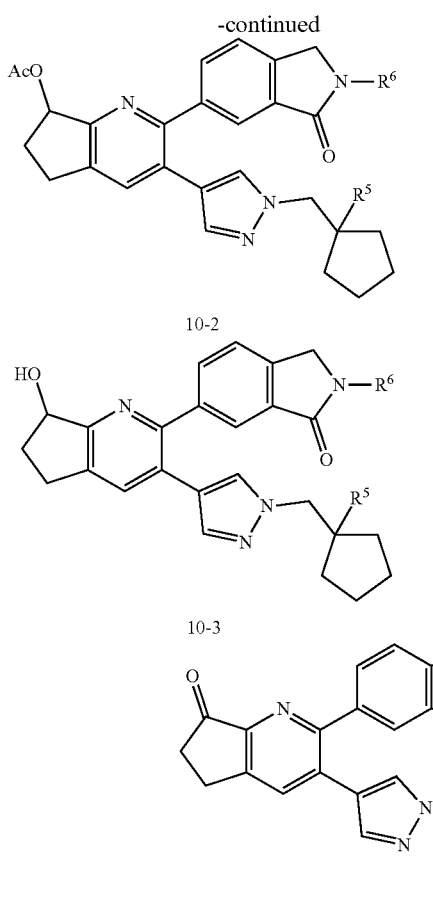

Compounds of formula (I) are prepared according to scheme 10 commencing with a palladium-mediated Suzuki coupling reaction of a prepared halopyridine 10-1 with intermediate C1. Saponification of the acetate 10-2 provides alcohol 10-3. Benzylic oxidation mediated by manganese oxide provides compounds of formula (I).

SCHEME 11

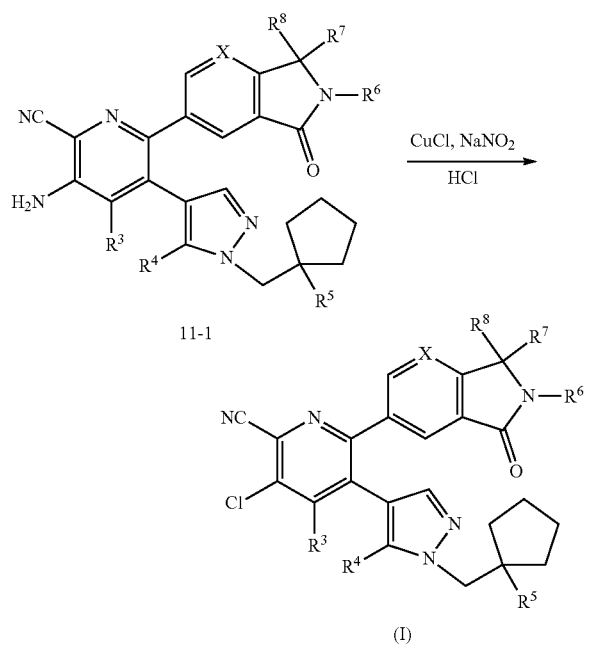

Compounds of formula (I) are synthesized via a Sandmeyer reaction from the corresponding prepared aniline 11-1.

SCHEME 12

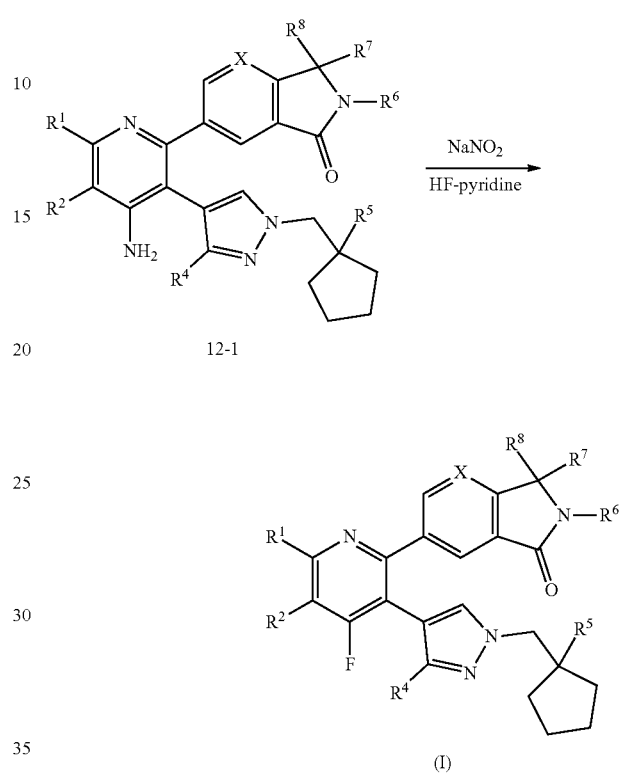

Compounds of formula (I) are prepared from the corresponding prepared aniline 12-1 under modified Balz-Schiemann reaction conditions utilizing Olah's reagent as the fluoride source.

SCHEME 13

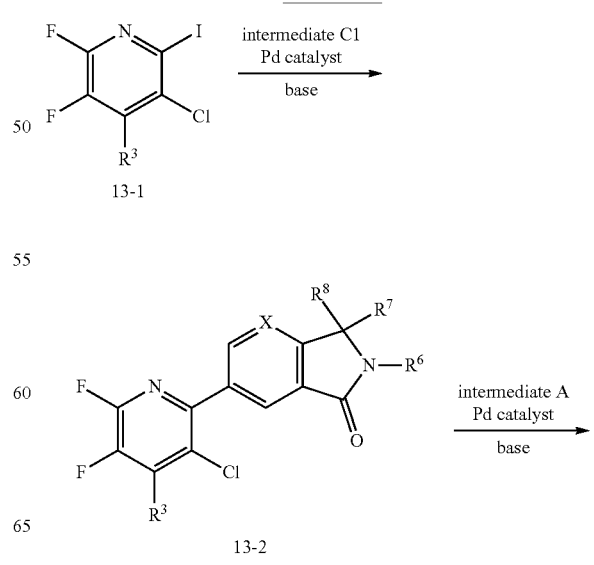

31

-continued

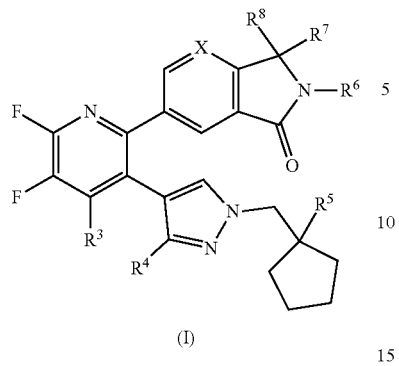

(I)

Compounds of formula (I) are prepared from a commercial 2-iodopyridine 13-1 which was coupled to intermediate C1 via a palladium-mediated Suzuki coupling reaction. A second Suzuki reaction of the resultant 3-chloropyridine 13-2 with intermediate A provides compounds of formula (I).

SCHEME 14

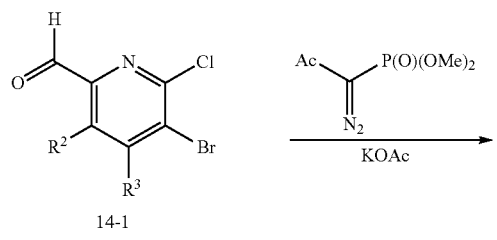

14-1

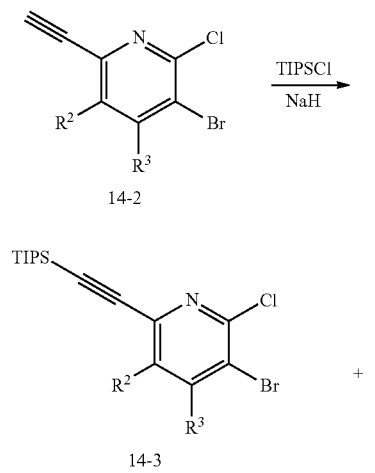

14-2

14-3

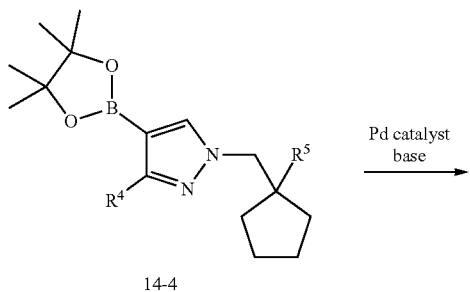

14-4

32

-continued

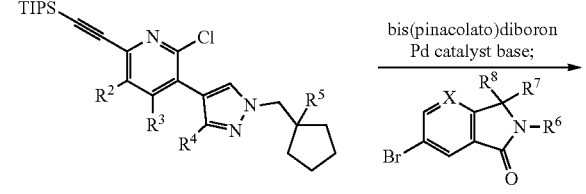

14-6

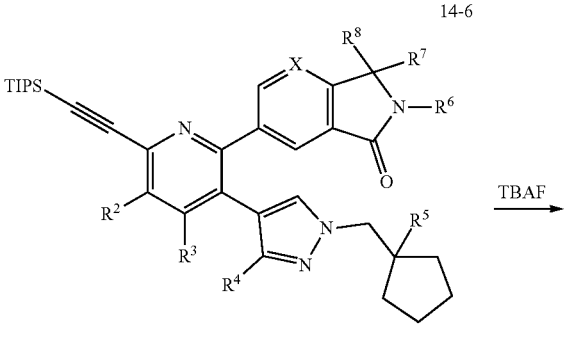

14-7

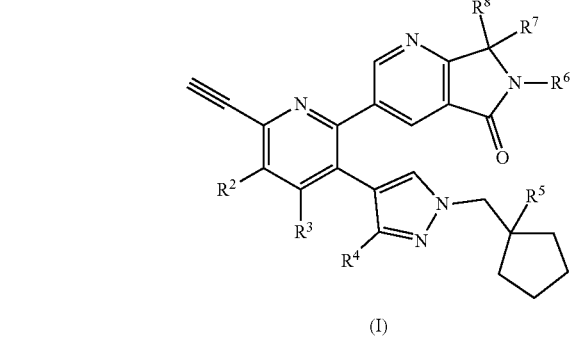

(I)

Compounds of formula (I) are prepared from 5-bromo-6-chloropicolinaldehyde (14-1) which by a Seyferth-Gilbert homologation reaction using the Bestmann-Ohira Reagent is transformed to the corresponding acetylene 14-2. Deprotonation of the terminal acetylene 14-2 and reaction with TIPSCl yields the TIPS-protected pyridine 14-3. A selective palladium-mediated Suzuki coupling reaction of bromide 15-3 with prepared boronic ester 14-4 provides coupled adduct 14-5. Chloride 14-5 is poised for a 2-step, 1-pot protocol for the in situ formation of a boronic ester of bromide 14-6 that undergoes a subsequent Suzuki coupling reaction mediated by palladium catalysts to yield 14-7. Deprotection by TBAF on 14-7 removes the protecting group to provide the final compound.

SCHEME 15

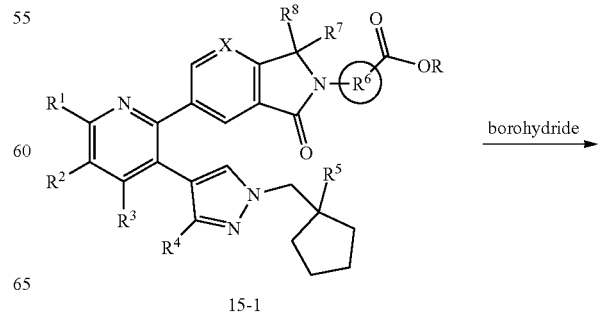

15-1

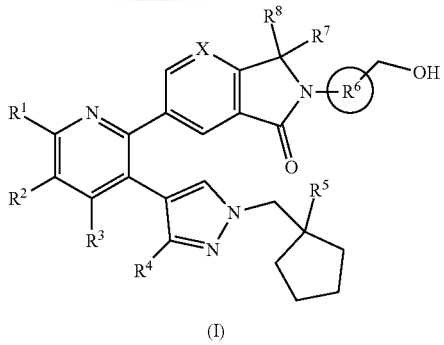

(I)

Compounds of formula (I) are prepared from the corresponding prepared ester 15-1 after reduction by a metal borohydride reagent.

Intermediates

Intermediate compounds of the present invention can be synthesized according to the schemes and procedures outlined below. Because the schemes are an illustration, the invention should not be construed as being limited by the chemical reactions and conditions expressed. The preparation of the various starting materials used in the schemes is within the skill of a person versed in the art.

SCHEME A

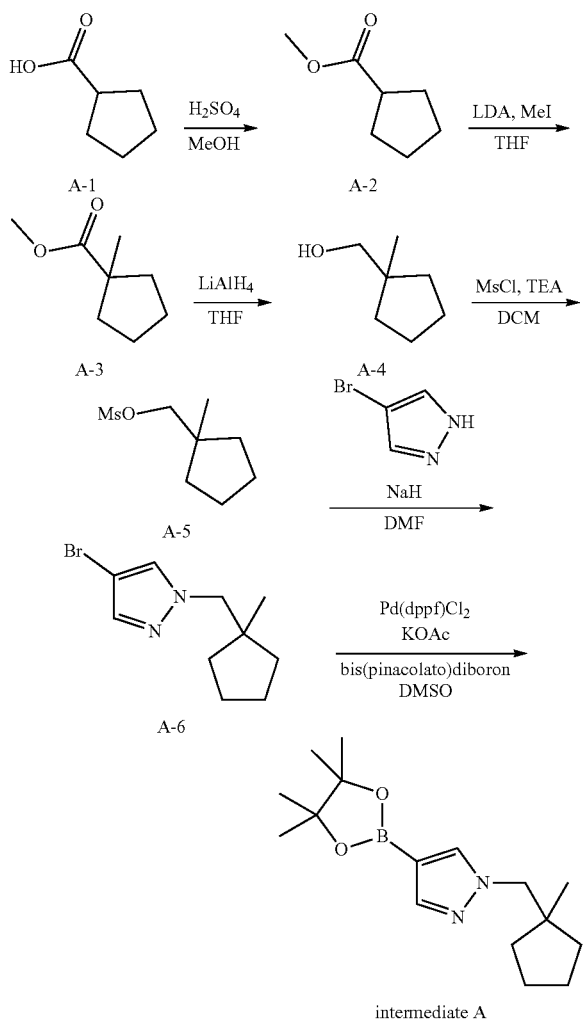

Intermediate A is prepared according to Scheme A via esterification and alkylation to arrive at ester A-3 from a commercially available acid A-1. Alcohol reduction and mesylation provides A-5, which is activated for displacement by 4-bromo-1H-pyrazole to yield bromide A-6. A Miyaura borylation provides intermediate A.

Intermediate A

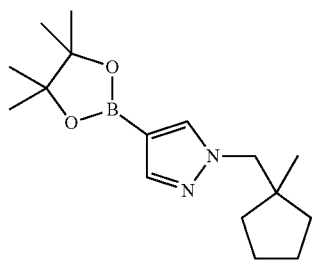 [SMILES: CC1(Cn2cc(B3OC(C)(C)C(C)(C)O3)cn2)CCCC1]

1-((1-Methylcyclopentyl)methyl)-4-(4,4,5,5-tetramethyl-1,3,2-dioxaborolan-2-yl)-1H-pyrazole (Scheme A)

Step 1: Methyl cyclopentanecarboxylate

Into a 10-L, 4-necked round-bottom flask, was placed cyclopentanecarboxylic acid (800 g, 7.01 mol). This was followed by the addition of methanol (4 L), in portions. To this was added sulfuric acid (32 mL), in portions. The resulting solution was stirred overnight at 75° C. in an oil bath. The resulting mixture was concentrated under vacuum. The resulting solution was diluted with water (4 L) and ether (2 L×2). The organic layers were separated and combined, washed with aqueous sodium chloride (2 L), dried over anhydrous sodium sulfate and concentrated under vacuum to yield the title compound.

Step 2: Methyl 1-methylcyclopentane-1-carboxylate

Into a 10 L, 4-necked round-bottom flask purged and maintained with an inert atmosphere of nitrogen, was placed methyl cyclopentanecarboxylate (400 g, 3.12 mol) in a solution of THF (4 L) at −78° C. To this was added LDA (3.12 L,) dropwise with stirring at −78° C. The resulting solution was stirred for 1.5 h at −78° C. before the dropwise addition of methyl iodide (1.33 L) at −78° C. The reaction was allowed to rest overnight and was then quenched by the addition of water (6 L). The resulting solution was partitioned with ether (2 L×3) and the organic layers were combined. The resulting mixture was washed with aqueous sodium chloride (2 L), dried over anhydrous sodium sulfate and concentrated under vacuum. The crude product was purified by distillation under reduced pressure (0.01 mm Hg) and the fraction was collected at 120° C. to yield the title compound.

Step 3: (1-Methylcyclopentyl)methanol

Into a 5 L, 4-necked round-bottom flask purged and maintained with an inert atmosphere of nitrogen, was placed tetrahydrofuran (1 L), LiAlH$_4$ (107 g, 2.82 mol). This was followed by the dropwise addition of a solution of methyl 1-methylcyclopentane-1-carboxylate (200 g, 1.36 mol) in THF (1 L) at 0° C. The resulting solution was stirred overnight at RT. The reaction was then quenched by the addition of water (214 mL) and 15% NaOH (321 g). The solids were filtered out and the filtrate was dried over anhydrous sodium sulfate and concentrated under vacuum. The residue was applied onto a silica gel column (1:10 ethyl acetate:petroleum ether) to yield the title compound.

Step 4: (1-Methylcyclopentyl)methyl methanesulfonate

Into a 3 L, 4-necked round-bottom flask purged and maintained with an inert atmosphere of nitrogen, was charged dichloromethane (1 L), (1-methylcyclopentyl) methanol (130 g, 1.14 mol) and TEA (161 g, 1.59 mol). After cooling to 0° C., a solution of MsCl (160 g) in dichloromethane (500 mL) was added dropwise to the reaction and the resulting solution was maintained at 0° C. for 2 hours and then at RT overnight. The reaction was then quenched by the addition of water (3 L) and the organic was extracted with dichloromethane (1 L×3) and the organic layers were combined. The resulting mixture was washed with brine (1 L), dried over anhydrous sodium sulfate and concentrated under vacuum. The residue was applied onto a silica gel column (1:15 ethyl acetate:petroleum ether) to yield the title compound.

Step 5: 4-Bromo-1-((1-methylcyclopentyl)methyl)-1H-pyrazole

Into a 3 L, 4-necked round-bottom flask purged and maintained with an inert atmosphere of nitrogen, was placed a solution of sodium hydride (53 g, 1.32 mol) in DMF (500 mL), 4-bromo-1H-imidazole (172 g, 1.17 mol). After stirring for 30 min at 40° C., a solution of (1-methylcyclopentyl)methyl methanesulfonate (150 g, 780 mmol) in DMF (1 L) was added portionwise. The resulting solution was stirred overnight at 90° C. The reaction mixture was cooled to 20° C. with a water/ice bath and was quenched by the addition of water (3 L). The organic was extracted with ethyl acetate (1 L×3) and the combined organic layers were washed with brine (1 L), dried over anhydrous sodium sulfate and concentrated under vacuum. The residue was applied onto a silica gel column (1:15 ethyl acetate:petroleum ether) to provide the title compound.

Step 6: 1-((1-Methylcyclopentyl)methyl)-4-(4,4,5,5-tetramethyl-1,3,2-dioxaborolan-2-yl)-1H-pyrazole Into a 3 L, 4-necked round-bottom flask purged and maintained with an inert atmosphere of nitrogen, was placed 4-bromo-1-[(1-methylcyclopentyl)methyl]-1H-imidazole (140 g, 576 mmol), 4,4,5,5-tetramethyl-2-(tetramethyl-1,3,2-dioxaborolan-2-yl)-1,3,2-dioxaborolane (205 g, 807 mmol), Pd(dppf)Cl$_2$ (80 g, 109 mmol), KOAc (119 g, 1.2 mol), DMSO (1.5 L). The resulting solution was stirred overnight at 80° C. The reaction mixture was cooled to RT and was quenched by the addition of water (3 L). The resulting solution was extracted with ethyl acetate (1 L×3) and the organic layers combined and washed with brine (1 L×2). The mixture was dried over anhydrous sodium sulfate, concentrated under reduced pressure and was purified by silica gel chromatography (1:10 ethyl acetate:petroleum ether) to yield the title compound. MS: 291 (M+1).

SCHEME B

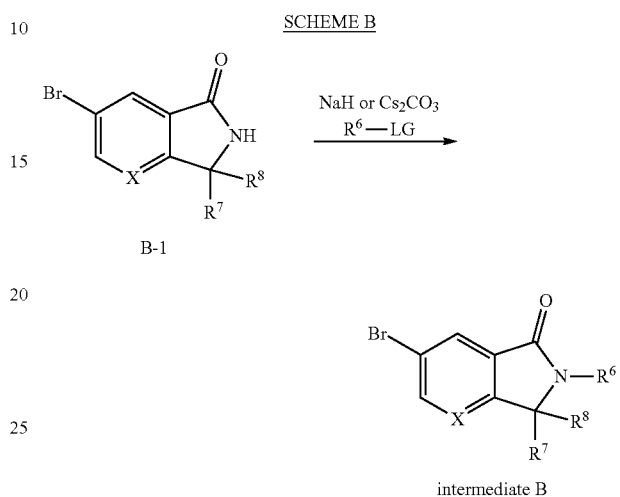

Intermediate B is prepared according to Scheme B via alkylation using a base (NaH or cesium carbonate) in the presence of an alkyl halide.

Intermediate B 1

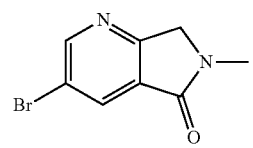

3-Bromo-6-methyl-6,7-dihydro-5H-pyrrolo[3,4-b]pyridin-5-one (Scheme B)

3-Bromo-6,7-dihydro-5H-pyrrolo[3,4-b]pyridin-5-one (320 mg, 1.5 mmol) was suspended using a freshly opened bottle of anhydrous DMF (12 mL) under an atmosphere of nitrogen. Sodium hydride (66 mg, 1.65 mmol) was added portionwise and after stirring for 30 minutes, a solution of iodomethane (103 µL, 1.65 mmol) in DMF (3 mL) was added dropwise. After 3 hours, the reaction was partitioned between water and ethyl acetate and the organic was washed with water (4×). The solution was dried over sodium sulfate, filtered and evaporated before purifying by silica gel chromatography (25-100% EtOAc/hexanes) to give the title compound. MS: 227, 229 (M+1). The following intermediates in table B were prepared according to scheme B using the procedure outlined in the synthesis intermediate B 1 using commercially available bromides or the use of alternative bases (i.e., cesium carbonate) in the presence of an appropriate alkyl bromide or iodide.

TABLE B

| Intermediate | Structure | Name | MS (M + 1) |
|---|---|---|---|
| B2 | 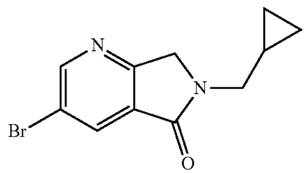 [SMILES: O=C1c2cc(Br)cnc2CN1CC1CC1] | 3-bromo-6-(cyclopropylmethyl)-6,7-dihydro-5H-pyrrolo[3,4-b]pyridin-5-one | 267, 269 |
| B3 | 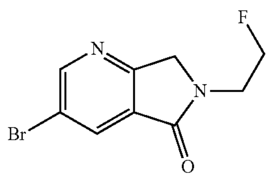 [SMILES: O=C1c2cc(Br)cnc2CN1CCF] | 3-bromo-6-(2-fluoroethyl)-6,7-dihydro-5H-pyrrolo[3,4-b]pyridin-5-one | see NMR data below* |
| B4 | 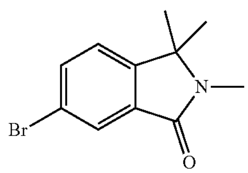 | 6-bromo-2,3,3-trimethylisoindolin-1-one | 254, 256 |
| B5 | 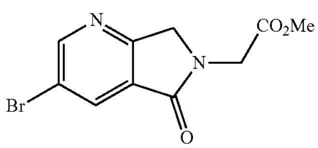 [SMILES: COC(=O)CN1Cc2ncc(Br)cc2C1=O] | methyl 2-(3-bromo-5-oxo-5,7-dihydro-6H-pyrrolo[3,4-b]pyridin-6-yl)acetate | 285, 287 |

*¹H NMR (500 MHz, CDCl₃): δ 3.93 (1 H, t, J = 4.72 Hz), 3.98 (1 H, t, J = 4.70 Hz), 4.57 (2 H, s), 4.65 (1 H, t, J = 4.70 Hz), 4.75 (1 H, t, J = 4.72 Hz), 8.25 (1 H, s), 8.80 (1 H, s).

SCHEME C

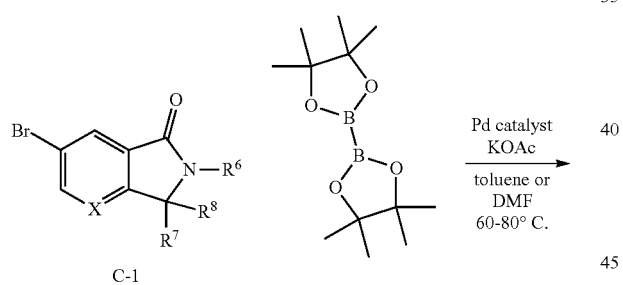

Intermediate C1

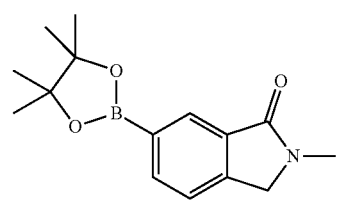

2-Methyl-6-(4,4,5,5-tetramethyl-1,3,2-dioxaborolan-2-yl)isoindolin-1-one (Scheme C)

To a solution of 6-bromo-2-methylisoindolin-1-one (5 g, 22.1 mmol) in DMF (30 mL) was added bis(pinacolato)diboron (6.18 g, 24.3 mmol) and potassium acetate (6.51 g, 66.4 mmol). The reaction mixture was degassed and back-filled with N₂ gas, and 1,1'-bis(diphenyl-phosphino)ferrocene palladium(II)dichloride dichloromethane (0.903 g, 1.106 mmol) was added. The reaction mixture was stirred at 80° C. for 10 hours. After diluting with EtOAc and water, the organic layer was concentrated and purified on silica column (100% EtOAc) to get the product as a mixture of the title compound as a boronic ester and boronic acid, which was not further purified. MS: 274 (M+1). ¹H NMR (500 MHz, CDCl₃): δ 8.33 (s, 1H), 7.98 (d, 7.5 Hz, 1H), 7.46 (d, 7.5 Hz, 1H), 4.41 (s, 2H), 3.22 (s, 3H), 1.38 (s, 12H). The following intermediates in table C were prepared according to scheme Intermediate C is prepared via a Miyaura borylation reaction that can be performed in either toluene or DMF with either 1,1'-bis(di-tert-butylphosphino)ferrocene palladium dichloride or 1,1'-bis(diphenylphosphino)ferrocene palladium(II)dichloride dichloromethane complex as the palladium catalyst.

C using the procedure outlined in the synthesis intermediate C1 using 1,1'-bis(di-tert-butylphosphino)ferrocene palladium dichloride or 1,1'-bis(diphenylphosphino)ferrocene palladium(II)dichloride dichloromethane complex as the palladium catalyst with toluene or DMF as the reaction solvent. The starting material bromide was either commercially available, known in the literature, or prepared using the protocol in scheme B.

TABLE C

| Intermediate | Structure | Name | MS (M + 1) |
|---|---|---|---|
| C2 | 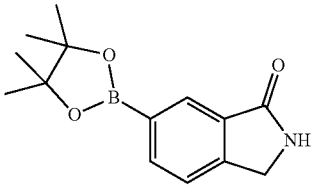 [SMILES: CC1(C)OB(c2ccc3c(c2)C(=O)NC3)OC1(C)C] | 6-(4,4,5,5-tetramethyl-1,3,2-dioxaborolan-2-yl)isoindolin-1-one | 260 |
| C3 | 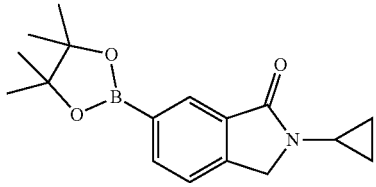 [SMILES: CC1(C)OB(c2ccc3c(c2)C(=O)N(C2CC2)C3)OC1(C)C] | 2-cyclopropyl-6-(4,4,5,5-tetramethyl-1,3,2-dioxaborolan-2-yl)isoindolin-1-one | 300 |
| C4 | 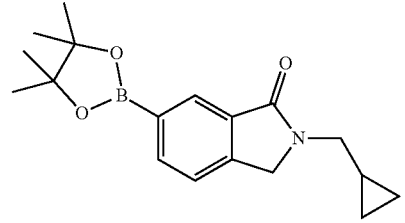 [SMILES: CC1(C)OB(c2ccc3c(c2)C(=O)N(CC2CC2)C3)OC1(C)C] | 2-(cyclopropylmethyl)-6-(4,4,5,5-tetramethyl-1,3,2-dioxaborolan-2-yl)isoindolin-1-one | 314 |
| C5 | 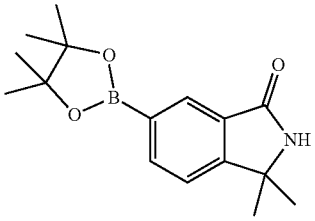 | 3,3-dimethyl-6-(4,4,5,5-tetramethyl-1,3,2-dioxaborolan-2-yl)isoindolin-1-one | 288 |
| C6 | 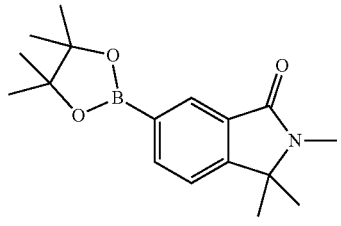 | 2,3,3-trimethyl-6-(4,4,5,5-tetramethyl-1,3,2-dioxaborolan-2-yl)isoindolin-1-one | 302 |
| C7 | 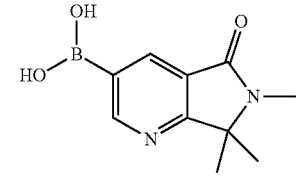 [SMILES: CN1C(=O)c2cc(B(O)O)cnc2C1(C)C] | (6,7,7-trimethyl-5-oxo-6,7-dihydro-5H-pyrrolo[3,4-b]pyridin-3-yl)boronic acid | 221 |
| C8 | 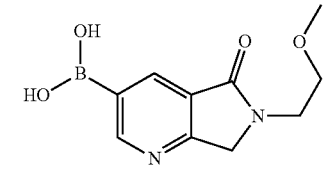 [SMILES: COCCN1Cc2ncc(B(O)O)cc2C1=O] | (6-(2-methoxyethyl)-5-oxo-6,7-dihydro-5H-pyrrolo[3,4-b]pyridin-3-yl)boronic acid | 237 |

TABLE C-continued

| Intermediate | Structure | Name | MS (M + 1) |
|---|---|---|---|
| C9 | 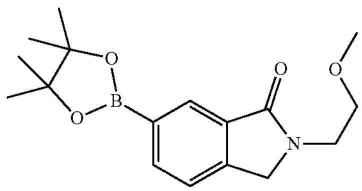 | 2-(2-methoxyethyl)-6-(4,4,5,5-tetramethyl-1,3,2-dioxaborolan-2-yl)isoindolin-1-one | 318 |
| C10 | 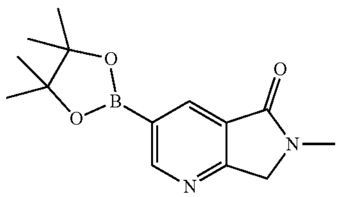 | 6-methyl-3-(4,4,5,5-tetramethyl-1,3,2-dioxaborolan-2-yl)-6,7-dihydro-5H-pyrrolo[3,4-6]pyridin-5-one | 193* |
| C11 | 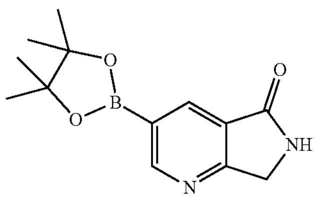 [SMILES: CC1(C)OB(c2cnc3c(c2)C(=O)NC3)OC1(C)C] | 3-(4,4,5,5-tetramethyl-1,3,2-dioxaborolan-2-yl)-6,7-dihydro-5H-pyrrolo[3,4-6]pyridin-5-one | 179* |
| C12 | 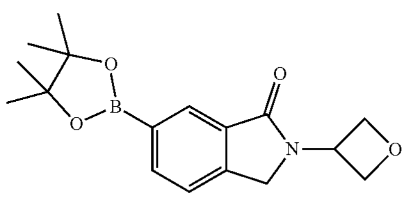 [SMILES: CC1(C)OB(c2ccc3c(c2)C(=O)N(C2COC2)C3)OC1(C)C] | 2-(oxetan-3-yl)-6-(4,4,5,5-tetramethyl-1,3,2-dioxaborolan-2-yl)isoindolin-1-one | 316 |
| C13 | 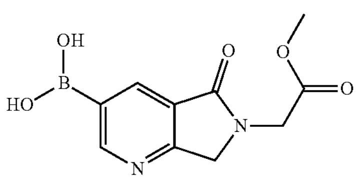 [SMILES: COC(=O)CN1Cc2ncc(B(O)O)cc2C1=O] | (6-(2-methoxy-2-oxoethyl)-5-oxo-6,7-dihydro-5H-pyrrolo[3,4-b]pyridin-3-yl)boronic acid | 251 |
| C14 | 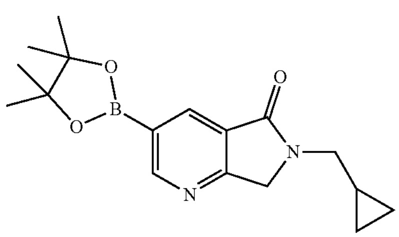 [SMILES: CC1(C)OB(c2cnc3c(c2)C(=O)N(CC2CC2)C3)OC1(C)C] | 6-(cyclopropylmethyl)-3-(4,4,5,5-tetramethyl-1,3,2-dioxaborolan-2-yl)-6,7-dihydro-5H-pyrrolo[3,4-b]pyridin-5-one | 233* |

*observed mass corresponds to the boronic acid

SCHEME D

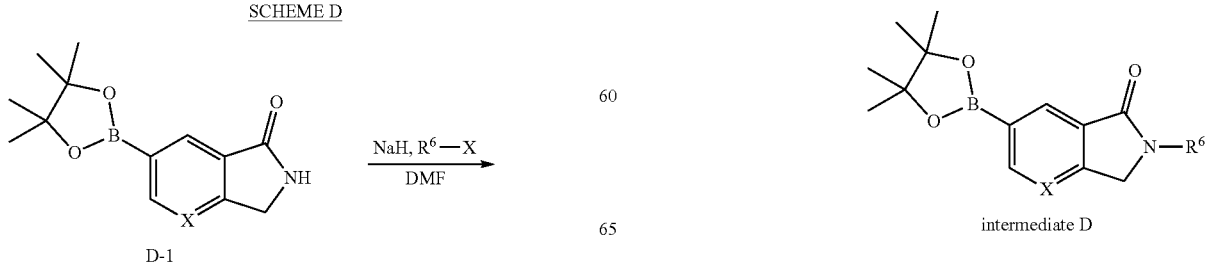

intermediate D

Intermediate D is prepared via alkylation of a prepared or commercially available boronic ester according to scheme D.

Intermediate D1

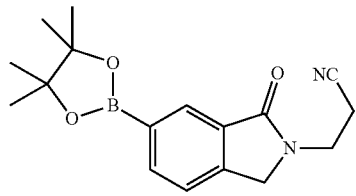 [SMILES: CC1(C)OB(c2ccc3c(c2)C(=O)N(CCC#N)C3)OC1(C)C]

3-(1-Oxo-6-(4,4,5,5-tetramethyl-1,3,2-dioxaborolan-2-yl)isoindolin-2-yl)propanenitrile (Scheme D)

To a 50 mL, one-necked round-bottomed flask was added 6-(4,4,5,5-tetramethyl-1,3,2-dioxaborolan-2-yl)isoindolin-1-one (intermediate C2, 200 mg, 0.77 mmol) in DMF (6 mL). The solution was cooled to 0° C., before adding sodium hydride (93 mg, 2.32 mmol). The reaction was then stirred for 12 h at 30° C. and was then quenched with water (6 mL). The volatiles were removed under reduced pressure and the reaction was extracted with DCM (10 mL×6). The combine organic layers were dried over anhydrous $Na_2SO_4$, filtered, concentrated and purified by prep-TLC (1:2 petroleum ether:EtOAc) to give the title compound. MS: 313 (M+1). The following intermediate in table D was prepared according to scheme D using the procedure outlined in the synthesis intermediate D1 using an appropriate akyl halide.

SCHEME E

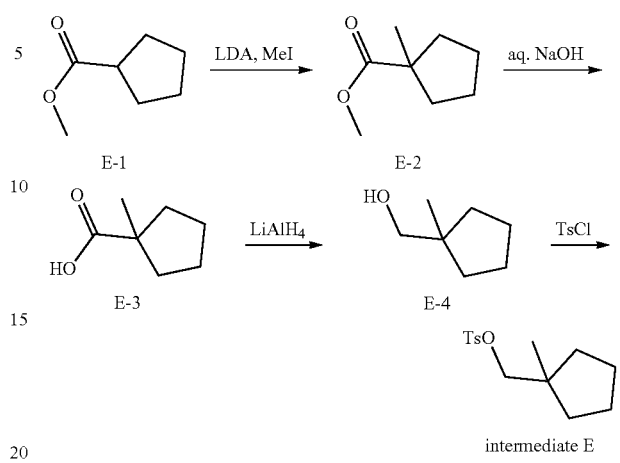

Intermediate E is prepared according to scheme E via alkylation commercially available ester E-1. Subsequent saponification to acid E-3 and reduction provides alcohol E-4, which is then tosylated to yield intermediate E.

Intermediate E

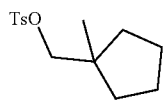

(1-Methylcyclopentyl)methyl 4-methylbenzenesulfonate (Scheme E)

TABLE D

| Intermediate | Structure | Name | MS (M + 1) |
|---|---|---|---|
| D2 | 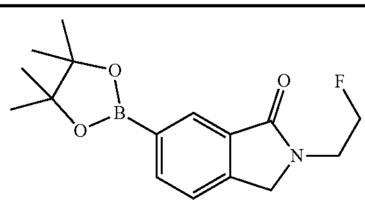 | 2-(2-fluoroethyl)-6-(4,4,5,5-tetramethyl-1,3,2-dioxaborolan-2-yl)isoindolin-1-one | 306 |
| D3 | 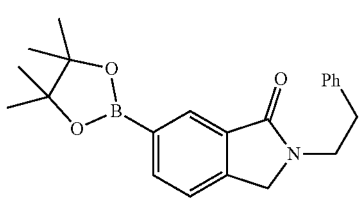 [SMILES: CC1(C)OB(c2ccc3c(c2)C(=O)N(CCc2ccccc2)C3)OC1(C)C] | 2-phenethyl-6-(4,4,5,5-tetramethyl-1,3,2-dioxaborolan-2-yl)isoindolin-1-one | 364 |
| D4 | 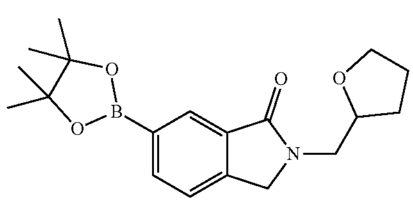 [SMILES: CC1(C)OB(c2ccc3c(c2)C(=O)N(CC2CCCO2)C3)OC1(C)C] | 2-((tetrahydrofuran-2-yl)methyl)-6-(4,4,5,5-tetramethyl-1,3,2-dioxaborolan-2-yl)isoindolin-1-one | 344 |

Step 1: Methyl 1-methylcyclopentane-1-carboxylate

To a solution of diisopropylamine (276 mL, 1.97 mol) in THF (400 mL) was added n-BuLi (664 mL, 1.66 mol) at 0° C. The reaction mixture was stirred at this temperature for 15 min before warming to RT and aging for 45 min. The system was then cooled to −70° C. and a solution of methyl cyclopentanecarboxylate (100 g, 780 mmol) in THF (800 mL) was added dropwise. After stirring for 2 h at this temperature, iodomethane (166 g, 1.18 mol) was added dropwise and the reaction mixture was stirred for an additional for 16 h. The mixture poured into aqueous $NH_4Cl$ and was extracted with EtOAc (2×). The organic was washed with brine, dried and concentrated before distillation to obtain the title compound.

Step 2: 1-Methylcyclopentane-1-carboxylic acid

To a stirred suspension of methyl 1-methylcyclopentane-1-carboxylate (100 g, 0.704 mol) in MeOH (500 mL) at RT was added aq. NaOH (352 mL, 1.4 mol). The mixture was stirred for 4 h and was then acidified with 4 N HCl to pH=2-3. The organic was extracted with EtOAc (3×), washed with brine, dried over anhydrous $Na_2SO_4$, and concentrated to give the title compound.

Step 3: (1-Methylcyclopentyl)methanol

To a mixture of $LiAlH_4$ (53.5 g, 1.41 mol) in THF (600 mL) was added a solution of 1-methylcyclopentane-1-carboxylic acid (100 g, 781 mmol) in THF at 0° C. The system was stirred for 30 min at the same temperature before warming to RT and aging the reaction for an additional 16 h. The reaction mixture was quenched by cautious addition of water, 15% NaOH solution, and water again at 0° C. After stirring for 1 h, the mixture was filtered and the filtrate washed with brine, dried and concentrated to give the title compound.

Step 4: (1-Methylcyclopentyl)methyl 4-methylbenzenesulfonate

To a solution of (1-methylcyclopentyl)methanol (170 g, 1.49 mol) in pyridine (1.5 L) at RT was added TsCl (284 g, 1.49 mol) in one portion. After stirring for 16 h, the reaction was poured into 1N HCl and was extracted with EtOAc (3×). The combined organics were washed with 1N HCl, brine, dried over sodium sulfate and concentrated. Purification by silica gel chromatography (100:1-50:1 petroleum ether:EtOAc) yielded the title compound. $^1$H NMR (500 MHz, $CDCl_3$): δ 7.811-7.790 (t, J=6.8 Hz, 2H), 7.369-7.284 (t, J=8.4 Hz, 2H), 3.766 (s, 2H), 2.463 (s, 3H), 1.630-1.271 (m, J=7.2 Hz, 8H), 0.983 (s, 3H).

SCHEME F

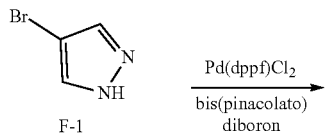

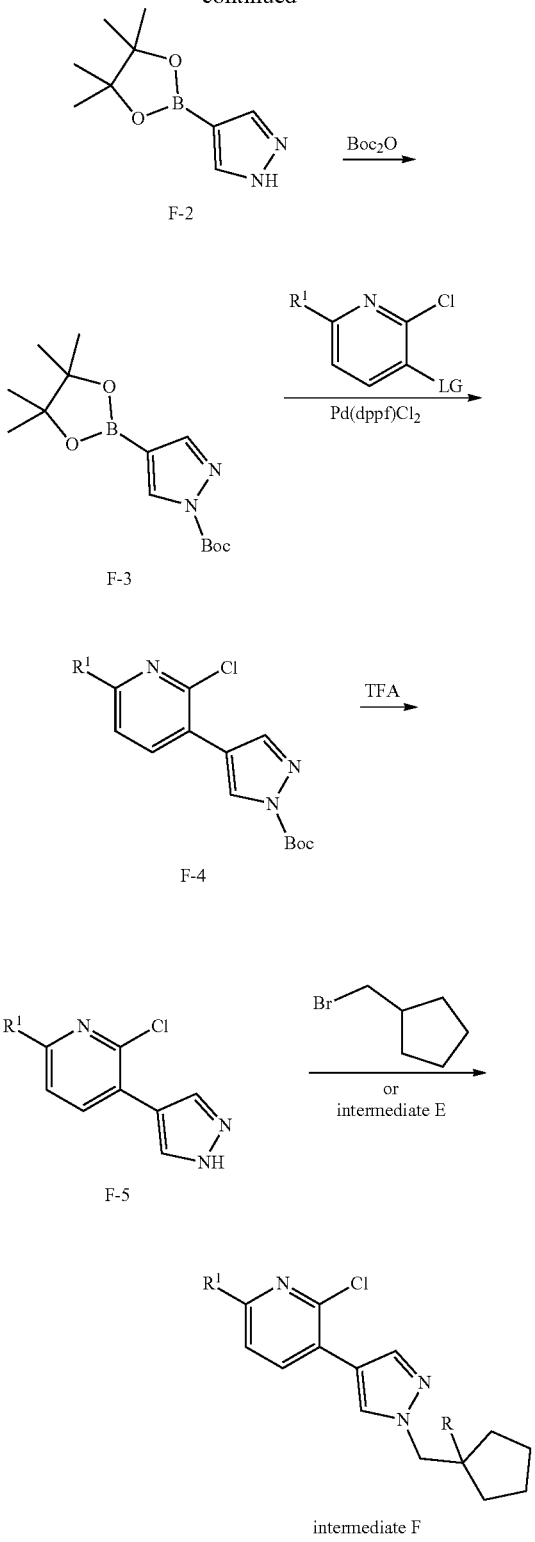

Intermediate F is prepared from a commercial bromopyrazole F-1, which is borylated to provide boronic ester F-2. Protection of the pyrazole enables a Suzuki cross-coupling with a known iodide or bromide to yield product F-4. Deprotection and subsequent alkylation with intermediate E or bromomethylcyclopentane provides intermediate F.

Intermediate F1

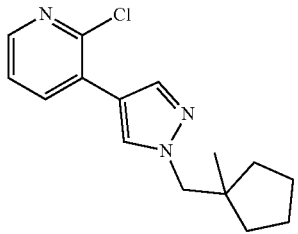 [SMILES: CC1(Cn2cc(-c3cccnc3Cl)cn2)CCCC1]

2-Chloro-3-(1-((1-methylcyclopentyl)methyl)-1H-pyrazol-4-yl)pyridine (Scheme F)

Step 1: 4-(4,4,5,5-Tetramethyl-1,3,2-dioxaborolan-2-yl)-1H-pyrazole

A flask charged with Pd(dppf)Cl$_2$ (20 g, 0.023 mol), KOAc(264 g, 2.72 mol), and bis(pinacolato)diboron (380 g, 1.48 mol) was flushed with N$_2$. Dioxane (3 L) and 4-bromo-1H-pyrazole (200 g×2, 1.36 mol) were then added. After being stirred at 80° C. for an appropriate period, the mixture was cooled and poured into water. The organic was extracted with EtOAc and then washed with water and brine, and dried over anhydrous Na$_2$SO$_4$ before concentrating to dryness. The residue was purified by silica gel column (5:1 petroleum ether:EtOAc) to give the title compound.

Step 2: tert-Butyl 4-(4,4,5,5-tetramethyl-1,3,2-dioxaborolan-2-yl)-1H-pyrazole-1-carboxylate Boc$_2$O (96 g, 0.48 mol) and DMAP (64 g, 0.64 mol) were added to a solution of 4-(4,4,5,5-tetramethyl-1,3,2-dioxaborolan-2-yl)-1H-pyrazole in DMF (1 L). The reaction mixture was stirred at room temperature for 7 h before the mixture was poured into water and EtOAc. The organic layer was separated and washed with water and brine, and dried over anhydrous Na$_2$SO$_4$ before concentrating to dryness. The resulting residue was purified by silica gel column (10:1 petroleum ether:EtOAc) to give the title compound.

Step 3: tert-Butyl 4-(2-chloropyridin-3-yl)-1H-pyrazole-1-carboxylate

2-Chloro-3-iodopyridine (100 g x 2, 0.42 mol) and tert-butyl 4-(2-chloropyridin-3-yl)-1H-pyrazole-1-carboxylate (123 g, 0.42 mol) was dissolved in dioxane (2 L). The system was placed under N$_2$ and Pd(dppf)Cl$_2$ (15 g, 17 mmol) was added to the solution and the reaction was heated to 65° C. for 3 h. The reaction was cooled to RT and the mixture was poured into water and partitioned with EtOAc. The organic was washed with water and brine, then dried over anhydrous Na$_2$SO$_4$ before concentrating to dryness. The title compound was obtained and was used without further purification.

Step 4: 2-Chloro-3-(1H-pyrazol-4-yl)pyridine

A solution of tert-butyl 4-(2-chloropyridin-3-yl)-1H-pyrazole-1-carboxylate (90 g, 0.32 mmol) in dioxane (600 mL) and 4 N HCl (400 mL in dioxane) was stirred at RT for 5 h. The mixture was filtered and the solids were washed with EtOAc and then dissolved into water (adjust pH~9 with aqueous NaOH). The organic was separated the organic, washed with water and brine, dried over anhydrous Na$_2$SO$_4$, and concentrated to give the title compound. MS: 313 (M+1). $^1$H NMR (500 MHz, CDCl$_3$): δ 8.326-8.310 (dd, J=1.6, 8.8 Hz, 1H), 8.040 (s, 2H), 7.837-7.813 (dd, J=2.0, 7.6 Hz, 1H), 7.307-7.276 (dd, J=4.8, 7.6 Hz, 1H).

The following intermediates in table F were prepared according to scheme F using the procedure outlined in the synthesis intermediate F1 using commercially available iodides or bromides in step 3 and using intermediate E or commercially available bromides for step 5.

TABLE F

| Intermediate | Structure | Name | MS (M + 1) |
|---|---|---|---|
| F2 | 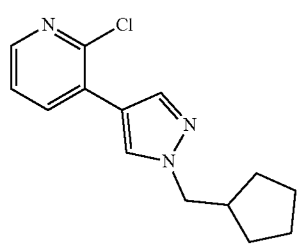 [SMILES: Clc1ncccc1-c1cnn(CC2CCCC2)c1] | 2-chloro-3-(1-(cyclopentylmethyl)-1H-pyrazol-4-yl)pyridine | 262 |
| F3 | 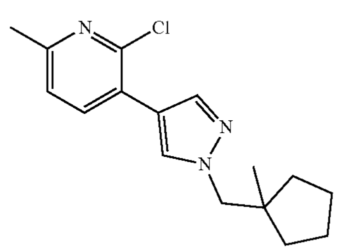 [SMILES: Cc1ccc(-c2cnn(CC3(C)CCCC3)c2)c(Cl)n1] | 2-chloro-6-methyl-3-(1-((1-methylcyclopentyl)methyl)-1H-pyrazol-4-yl)pyridine | 290 |

TABLE F-continued

| Intermediate | Structure | Name | MS (M + 1) |
|---|---|---|---|
| F4 | 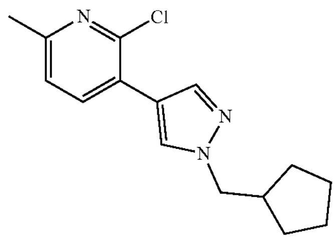 [SMILES: Cc1ccc(-c2cnn(CC3CCCC3)c2)c(Cl)n1] | 2-chloro-3-(1-(cyclopentylmethyl)-1H-pyrazol-4-yl)-6-methylpyridine | 276 |

SCHEME G

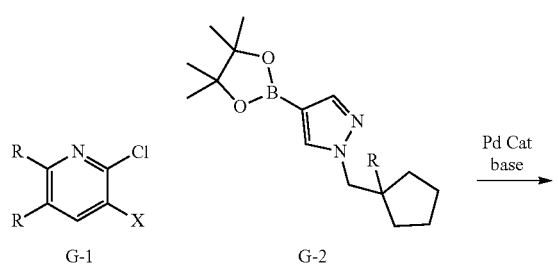

Intermediate G is prepared via a Suzuki reaction of a commercially available, known or prepared pyridines (G-1) and boronic ester G-2, which is commercially available or prepared.

Intermediate G1

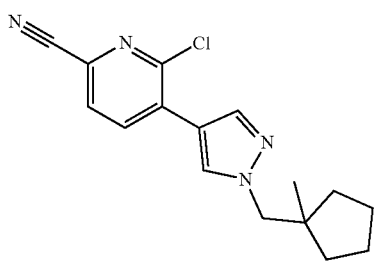

6-Chloro-5-(1-((1-methylcyclopentyl)methyl)-1H-pyrazol-4-yl)picolinonitrile (Scheme G)

Into a 5 L, 4-necked round-bottom flask purged and maintained with an inert atmosphere of nitrogen, was placed 1-[(1-methylcyclopentyl)methyl]-4-(tetramethyl-1,3,2-dioxaborolan-2-yl)-1H-pyrazole (intermediate A, 46.5 g, 160.23 mmol), 5-bromo-6-chloropyridine-2-carbonitrile (for preparation, see: Pettersson, M.; et. al. Bioorganic & Medicinal Chemistry Letters, 2012, 22(8), 2906-2911 or Am Ende, C. W.; et. al. PCT Int. Appl., 2012131539, 4 Oct. 2012) (42 g, 193 mmol), Pd(dppf)Cl$_2$ (28.5 g, 40 mmol), potassium carbonate (55.3 g, 400.72 mmol), dioxane (1.45 L), and water (580 mL). The resulting solution was stirred for 10 min at 25° C. and then at 100° C. for 3 h. The reaction was then quenched by the addition of water (2 L) and was partitioned with EtOAc (3 L×3). The combined organic layers were dried over anhydrous sodium sulfate and concentrated under reduced pressure. The residue was applied onto a silica gel column (5:1 petroleum ether:EtOAc) to yield the title compound. MS: 301 (M+1). $^1$H NMR (400 MHz, CDCl$_3$): δ 1.01 (3H, s), 1.38-1.42 (2H, m), 1.42-1.74 (6H, m), 4.09 (2H, s), 7.63-7.65 (1H, s), 7.86 (1H, s), 7.92-7.94 (1H, m), 8.00 (1H, s). The following intermediates in table G were prepared according to scheme G using the procedure outlined in the synthesis intermediate G1 using intermediate A or 1-(cyclopentylmethyl)-4-(4,4, 5,5-tetramethyl-1,3,2-dioxaborolan-2-yl)-1H-pyrazole (CAS: 1233526-51-6) and commercially available, known (i.e., Frei, Beat; et. al. PCT Int. Appl. WO 2014086705, Jun. 12, 2014) or prepared 2-halopyridines. Alternative conditions can be used in this reaction, such that the catalyst is 1,1'-bis(di-tert-butylphosphino)ferrocene palladium dichloride or the solvent is THF and temperature can range from RT to 110° C. as appropriate for each substrate.

TABLE G

| Intermediate | Structure | Name | MS (M + 1) |
|---|---|---|---|
| G2 | 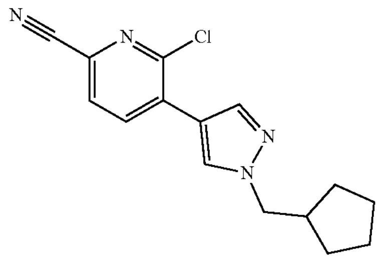 [SMILES: CC1(Cn2cc(-c3ccc(C#N)nc3Cl)cn2)CCCC1] | 6-chloro-5-(1-(cyclopentylmethyl)-1H-pyrazol-4-yl)picolinonitrile | 287 |
| G3 | 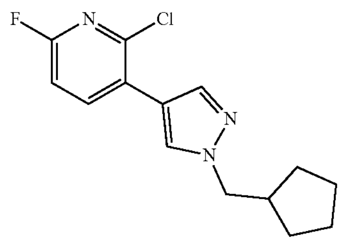 [SMILES: Fc1ccc(-c2cnn(CC3CCCC3)c2)c(Cl)n1] | 2-chloro-3-(1-(cyclopentylmethyl)-1H-pyrazol-4-yl)-6-fluoropyridine | 280 |
| G4 | 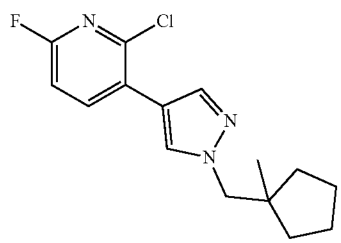 [SMILES: CC1(Cn2cc(-c3ccc(F)nc3Cl)cn2)CCCC1] | 2-chloro-6-fluoro-3-(1-((1-methylcyclopentyl)methyl)-1H-pyrazol-4-yl)pyridine | 294 |
| G5 | 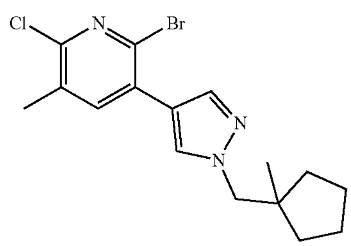 [SMILES: Cc1cc(-c2cnn(CC3(C)CCCC3)c2)c(Br)nc1Cl] | 2-bromo-6-chloro-5-methyl-3-(1-((1-methylcyclopentyl)methyl)-1H-pyrazol-4-yl)pyridine | 368, 370 |
| G6 | 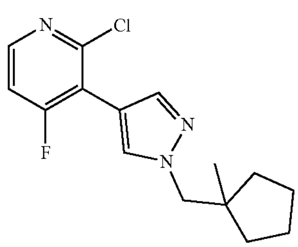 [SMILES: CC1(Cn2cc(-c3c(F)ccnc3Cl)cn2)CCCC1] | 2-chloro-3-(1-(cyclopentylmethyl)-1H-pyrazol-4-yl)-4-fluoropyridine | 280 |
| G7 | 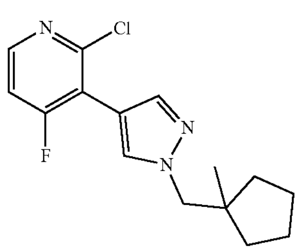 [SMILES: CC1(Cn2cc(-c3c(F)ccnc3Cl)cn2)CCCC1] | 2-chloro-4-fluoro-3-(1-((1-methylcyclopentyl)methyl)-1H-pyrazol-4-yl)pyridine | 294 |

TABLE G-continued

| Intermediate | Structure | Name | MS (M + 1) |
| --- | --- | --- | --- |
| G8 | 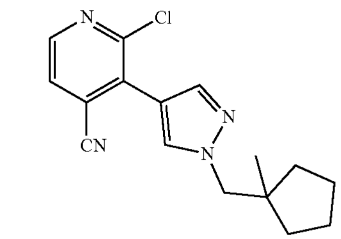 [SMILES: CC1(Cn2cc(-c3c(C#N)ccnc3Cl)cn2)CCCC1] | 2-chloro-3-(1-((1-methylcyclopentyl)methyl)-1H-pyrazol-4-yl)isonicotinonitrile | 301 |
| G9 | 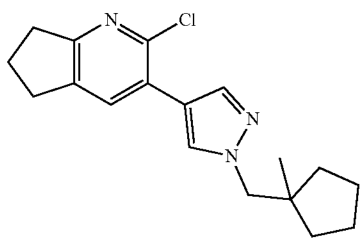 [SMILES: CC1(Cn2cc(-c3cc4c(nc3Cl)CCC4)cn2)CCCC1] | 2-chloro-3-(1-((1-methylcyclopentyl)methyl)-1H-pyrazol-4-yl)-6,7-dihydro-5H-cyclopenta[b]pyridine | 316 |
| G10 | 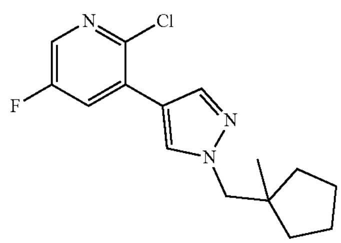 [SMILES: CC1(Cn2cc(-c3cc(F)cnc3Cl)cn2)CCCC1] | 2-chloro-5-fluoro-3-(1-((1-methylcyclopentyl)methyl)-1H-pyrazol-4-yl)pyridine | 294 |
| G11 | 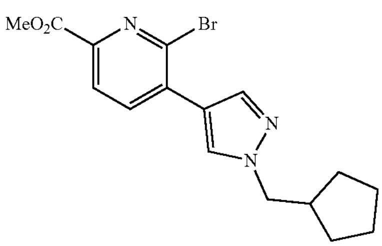 [SMILES: COC(=O)c1ccc(-c2cnn(CC3CCCC3)c2)c(Br)n1] | methyl 6-chloro-5-(1-(cyclopentylmethyl)-1H-pyrazol-4-yl)picolinate | 320 |
| G12 | 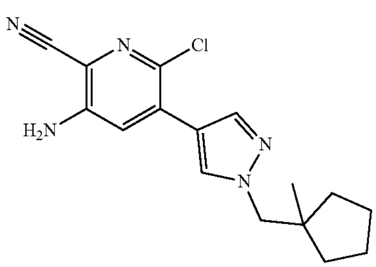 | 3-amino-6-chloro-5-(1-((1-methylcyclopentyl)methyl)-1H-pyrazol-4-yl)picolinonitrile | 316 |
| G13 | 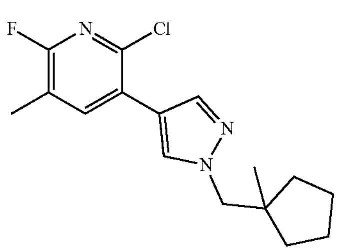 [SMILES: Cc1cc(-c2cnn(CC3(C)CCCC3)c2)c(Cl)nc1F] | 2-chloro-6-fluoro-5-methyl-3-(1-((1-methylcyclopentyl)methyl)-1H-pyrazol-4-yl)pyridine | 308 |

TABLE G-continued

| Intermediate | Structure | Name | MS (M + 1) |
|---|---|---|---|
| G14 | 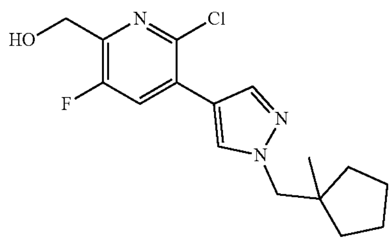 [SMILES: CC1(Cn2cc(-c3cc(F)c(CO)nc3Cl)cn2)CCCC1] | (6-chloro-3-fluoro-5-(1-((1-methylcyclopentyl)methyl)-1H-pyrazol-4-yl)pyridin-2-yl)methanol | 324 |
| G15 | 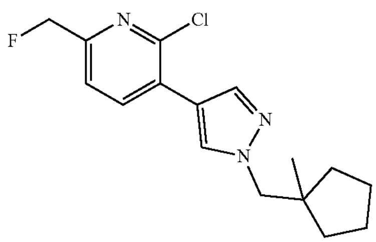 [SMILES: CC1(Cn2cc(-c3ccc(CF)nc3Cl)cn2)CCCC1] | 2-chloro-6-(fluoromethyl)-3-(1-((1-methylcyclopentyl)methyl)-1H-pyrazol-4-yl)pyridine | 308 |
| G16 | 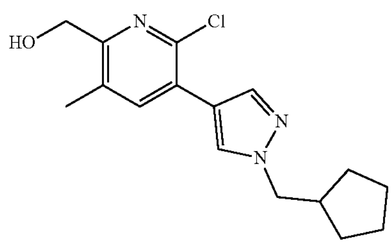 [SMILES: Cc1cc(-c2cnn(CC3CCCC3)c2)c(Cl)nc1CO] | (6-chloro-3-methyl-5-(1-((1-methylcyclopentyl)methyl)-1H-pyrazol-4-yl)pyridin-2-yl)methanol | 320 |
| G17 | 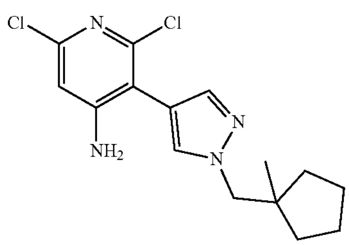 [SMILES: CC1(Cn2cc(-c3c(N)cc(Cl)nc3Cl)cn2)CCCC1] | 2,6-dichloro-3-(1-((1-methylcyclopentyl)methyl)-1H-pyrazol-4-yl)pyridin-4-amine | 325 |
| G18 | 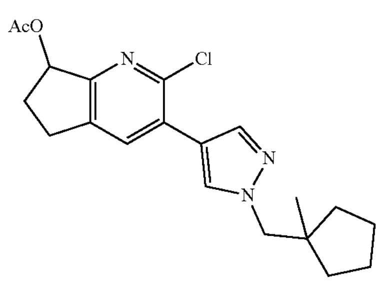 [SMILES: CC(=O)OC1CCc2cc(-c3cnn(CC4(C)CCCC4)c3)c(Cl)nc21] | 2-chloro-3-(1-((1-methylcyclopentyl)methyl)-1H-pyrazol-4-yl)-6,7-dihydro-5H-cyclopenta[b]pyridin-7-yl acetate | 374 |
| G19 | 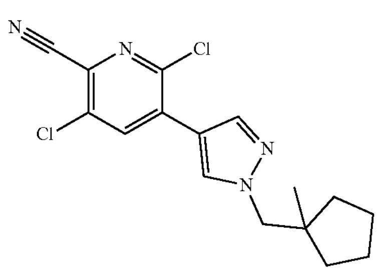 [SMILES: CC1(Cn2cc(-c3cc(Cl)c(C#N)nc3Cl)cn2)CCCC1] | 3,6-dichloro-5-(1-((1-methylcyclopentyl)methyl)-1H-pyrazol-4-yl)picolinonitrile | *see NMR data |

TABLE G-continued

| Intermediate | Structure | Name | MS (M + 1) |
|---|---|---|---|
| G20 | 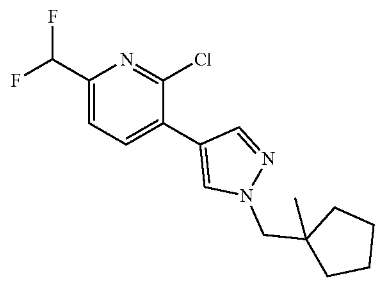 [SMILES: CC1(Cn2cc(-c3ccc(C(F)F)nc3Cl)cn2)CCCC1] | 2-chloro-6-(difluoromethyl)-3-(1-((1-methylcyclopentyl)methyl)-1H-pyrazol-4-yl)pyridine | 326 |
| G21 | 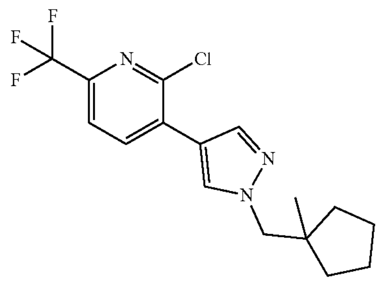 [SMILES: CC1(Cn2cc(-c3ccc(C(F)(F)F)nc3Cl)cn2)CCCC1] | 2-chloro-3-(1-((1-methylcyclopentyl)methyl)-1H-pyrazol-4-yl)-6-(trifluoromethyl)pyridine | 344 |
| G22** | 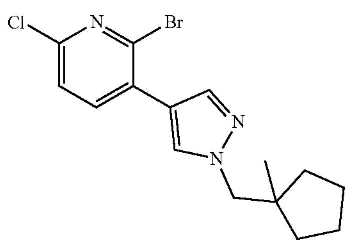 [SMILES: CC1(Cn2cc(-c3ccc(Cl)nc3Br)cn2)CCCC1] | 2-bromo-6-chloro-3-(1-((1-methylcyclopentyl)methyl)-1H-pyrazol-4-yl)pyridine | 354, 356 |

*intermediate G19: $^1$H NMR (400 MHz, CDCl$_3$): δ 7.96 (s, 1H), 7.87 (s, 1H), 7.81 (s, 1H), 4.02 (s, 2H), 1.60-1.66 (m, 5H), 1.30-1.37 (m, 3H), 1.17 (s, 3H).
**reaction run with commerically available 2-bromo-6-chloro-3-iodopyridine

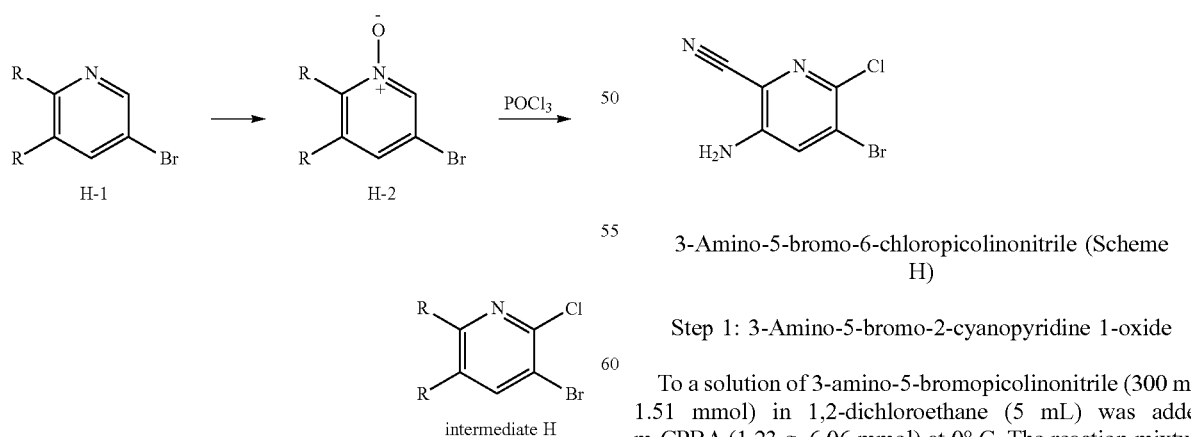

Intermediate H is prepared according to scheme H via an esterification of carboxylic acid H-1 followed by N-oxide formation and chlorination.

Intermediate H1

3-Amino-5-bromo-6-chloropicolinonitrile (Scheme H)

Step 1: 3-Amino-5-bromo-2-cyanopyridine 1-oxide

To a solution of 3-amino-5-bromopicolinonitrile (300 mg, 1.51 mmol) in 1,2-dichloroethane (5 mL) was added m-CPBA (1.23 g, 6.06 mmol) at 0° C. The reaction mixture was stirred 0° C. for 1 h and then 80° C. for 20 h. The reaction quenched with saturated aqueous Na$_2$S$_2$O$_3$ (10 mL) and then extracted with DCM (10 mL×3). The combined organics were dried over anhydrous Na$_2$SO$_4$ and concentrated. The residue was purified by silica gel chromatography (20%-80% EtOAc/petroleum ether) to give the title compound. MS: 214, 216 (M+1).

Step 2: 3-Amino-5-bromo-6-chloropicolinonitrile

3-Amino-5-bromo-2-cyanopyridine 1-oxide (50 mg, 0.23 mmol) in phosphoryl trichloride (358 mg, 2.336 mmol) was stirred 16 h at 25° C. The reaction solution was carefully added to water. The mixture was extracted with DCM (3×10 mL) and the combined organics were dried over anhydrous $Na_2SO_4$ and concentrated. The residue was purified by prep TLC (1:1 petroleum ether:EtOAc, $R_f$=0.7) to give the title compound. MS: 232, 234, 236 (M+1). The following intermediates in table H were prepared according to scheme H using the procedure outlined in the synthesis intermediate H1 using commercially available pyridines.

TABLE H

| Intermediate | Structure | Name | MS (M + 1) |
|---|---|---|---|
| H2 | (structure) | 3-bromo-2-chloro-6-fluoro-5-methylpyridine | 224, 226 |

SCHEME I

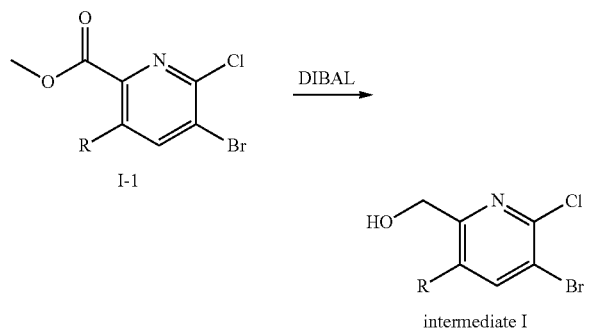

Intermediate I is prepared according to scheme I from the reduction of a commercial pyridine (CAS: 1211528-83-4 or 1256807-25-6).

Intermediate I1

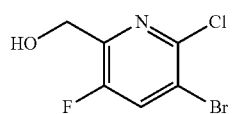

(5-Bromo-6-chloro-3-fluoropyridin-2-yl)methanol
(Scheme I)

Dibal-H (1 M in THF, 1.49 mL) was added through an additional funnel over 1.5 h to a stirring, cooled (−78° C.) solution of methyl 5-bromo-6-chloro-3-fluoropicolinate (200 mg, 0.745 mmol). After 2 h at this temperature, an additional portion of Dibal-H (1 M in THF, 1.49 mL,) was added and the reaction was warmed to rt. After 2 h, methanol (15 mL) was added via additional funnel over 30 min. The reaction was diluted with water and partitioned with DCM (50 mL×2) and the combined organic layers were washed with brine, dried over anhydrous $Na_2SO_4$, and concentrated. The crude material was purified by silica gel (0-25% EtOAc/hexanes) to yield the title compound. MS: 240, 242 (M+1). The following intermediates in table I were prepared according to scheme I using the procedure outlined in the synthesis intermediate I2 using commercially available pyridines.

TABLE I

| Intermediate | Structure | Name | MS (M + 1) |
|---|---|---|---|
| I2 | (structure) | (5-bromo-6-chloro-3-methylpyridin-2-yl)methanol | 236, 238 |

SCHEME J

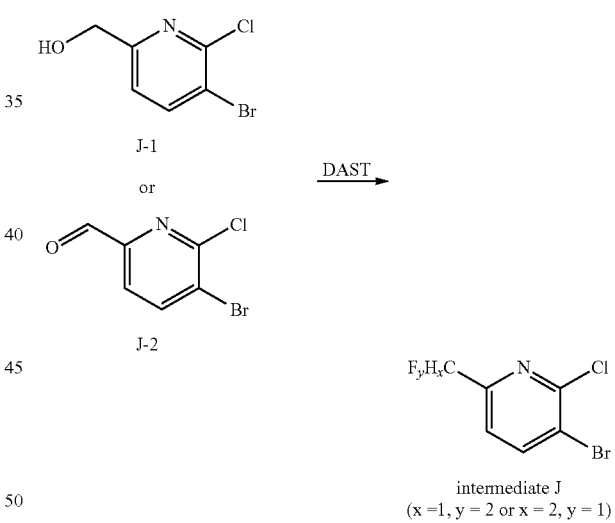

Intermediate J is prepared according to scheme J from treatment with DAST with either commercial alcohol J-1 or aldehyde J-2.

Intermediate J1

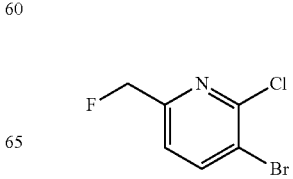

3-Bromo-2-chloro-6-(fluoromethyl)pyridine (Scheme J)

To a solution of (5-bromo-6-chloropyridin-2-yl)methanol (200 mg, 0.90 mmol) in DCM (5 mL) was added DAST (0.36 mL, 2.7 mmol) at 25° C. The resulting mixture was stirred for 12 h at 25° C., before the reaction mixture was quenched with saturated aqueous NaHCO$_3$ (15 mL). The organic was extracted with DCM (20 mL×3) and the combined organic layers were washed with water (10 mL) then brine (10 mL), dried over anhydrous sodium sulfate, filtered and concentrated to give the title compound. The material was used without further purification. MS: 224, 226 (M+1). The following intermediate in table J was prepared according to scheme J using the procedure outlined in the synthesis intermediate J1 using the corresponding commercial aldehyde with the reaction carried out at 0° C. for 3 h.

TABLE J

| Intermediate | Structure | Name | MS (M + 1) |
|---|---|---|---|
| J2 | ![F,F,N,Cl,Br structure] | 3-bromo-2-chloro-6-(difluoromethyl)pyridine | *see NMR data |

*intermediate J2: $^1$H NMR (400 MHz, CDCl$_3$): δ 8.07 (d, J = 8.4 Hz, 1H), 7.44 (d, J = 8.0 Hz, 1H), 6.54 (t, J = 55 Hz, 1 H).

3-Bromo-2-chloro-6,7-dihydro-5H-cyclopenta[b]pyridin-7-yl acetate (Scheme K)

Step 1: 3-Bromo-2-chloro-6,7-dihydro-5H-cyclopenta[b]pyridine 1-oxide

To a stirred solution of 3-bromo-2-chloro-6,7-dihydro-5H-cyclopenta[b]pyridine (80 mg, 0.34 mmol) in DCM (3 mL) was added m-CPBA (119 mg, 0.69 mmol) at 0° C. The reaction was allowed to warm to RT and was stirred for an additional 6 h. Aqueous NaHCO$_3$ was added to reaction (pH=8) and mixture was extracted with EtOAc (50 mL×2). The combined organic layers were washed with brine, dried over anhydrous Na$_2$SO$_4$ and concentrated under reduced pressure. The residue was purified by prep-TLC (3:1 petroleum ether: EtOAc, R$_f$=0.3) to give the title compound. MS: 248, 250 (M+1)

Step 2: 3-Bromo-2-chloro-6,7-dihydro-5H-cyclopenta[b]pyridin-7-yl acetate

To 3-bromo-2-chloro-6,7-dihydro-5H-cyclopenta[b]pyridine 1-oxide (45 mg, 0.18 mmol) was added Ac$_2$O (3 mL). The reaction was stirred at 100° C. for 10 h after which the mixture diluted with saturated aqueous Na$_2$CO$_3$ (30 mL) and was extracted with EtOAc (50 mL×2). The combined organic layers were dried over anhydrous Na$_2$SO$_4$, filtered and concentrated under reduced pressure. The crude product was purified by prep-TLC (5:1 petroleum ether:EtOAc, R$_f$=0.5) to give the title compound. MS: 290, 292 (M+1).

SCHEME K

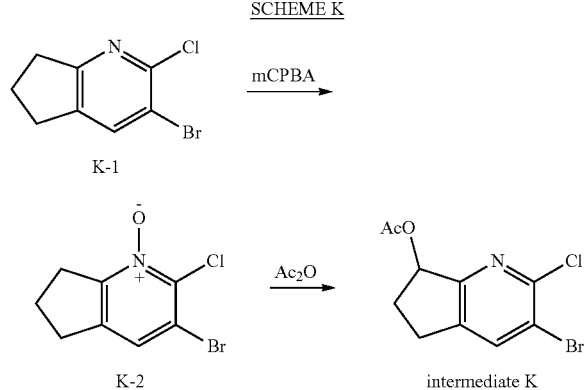

Intermediate K is prepared from a commercial bromide (CAS: 1508793-36-9) according to scheme K after formation of N-oxide K-2 and rearrangement in the presence of acetic anhydride.

Intermediate K

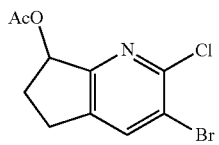 [SMILES: CC(=O)OC1CCc2cc(Br)c(Cl)nc21]

SCHEME L

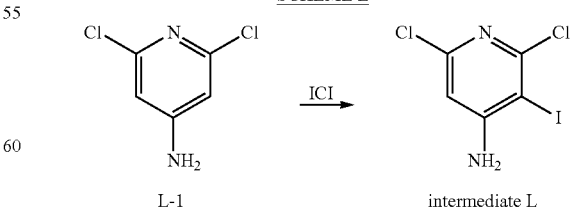

Intermediate L is prepared according to scheme L from 2,6-dichloropyridin-4-amine after treatment with iodine monochloride.

Intermediate L

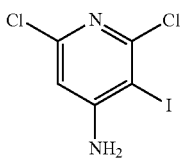

2,6-Dichloro-3-iodopyridin-4-amine (Scheme L)

2,6-Dichloropyridin-4-amine (200 mg) was added to ICl (1 M in AcOH, 1.22 mL) followed by KOAc (120 mg). The reaction was stirred at RT for 8 h before additional ICl (1 M in AcOH, 1.22 mL). The reaction was stirred overnight and water was added (4 mL) and the slurry was filtered and was dried under reduced pressure to yield the title compound. MS: 289 (M+1).

SCHEME M

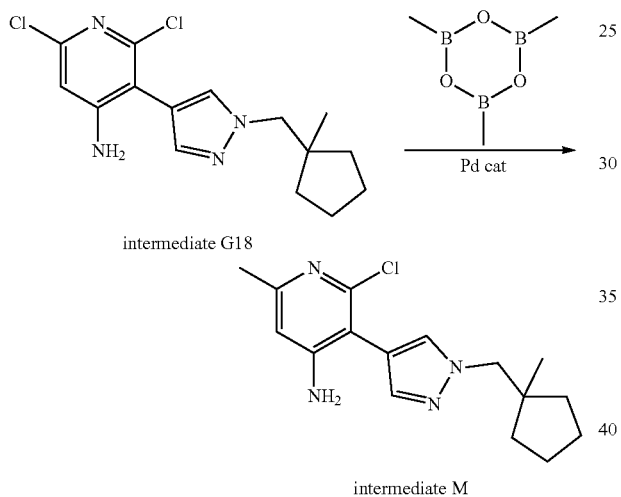

Intermediate M is prepared according to scheme M from intermediate G18 after a Suzuki coupling reaction with trimethylboroxin.

Intermediate M

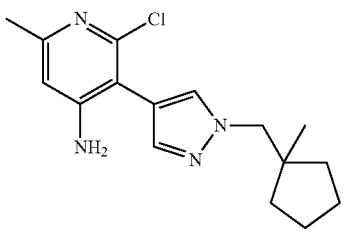 [SMILES: Cc1cc(N)c(-c2cnn(CC3(C)CCCC3)c2)c(Cl)n1]

2-Chloro-6-methyl-3-(1-((1-methylcyclopentyl)methyl)-1H-pyrazol-4-yl)pyridin-4-amine (Scheme M)

2,4,6-Trimethyl-1,3,5,2,4,6-trioxatriborinane (164 mg, 1.3 mmol), 2,6-dichloro-3-(1-((1-methylcyclopentyl)methyl)-1H-pyrazol-4-yl)pyridin-4-amine (intermediate G18, 355 mg, 1.09 mmol) and 1,1'-bis(di-tert-butylphosphino)ferrocene palladium dichloride (71 mg, 0.109 mmol) were placed in a 4 mL reaction vial under a nitrogen atmosphere. 1,4-Dioxane (1 mL) and potassium carbonate (3.27 mL, 3 M in water) was added to the sealed vial and the system was heated to 90° C. for 40 min. The crude mixture was filtered and purified by mass triggered reverse phase HPLC (ACN/water with 0.1% $NH_3OH$ modifier) to afford the title compound. MS: 285 (M+1).

SCHEME N

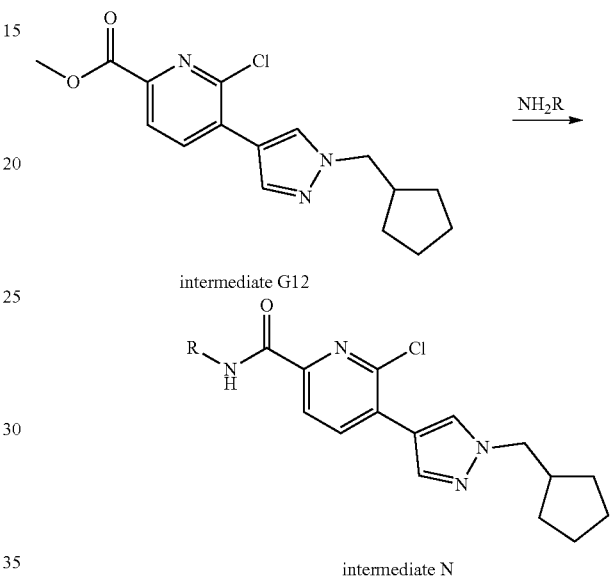

Intermediate N is prepared according to scheme N by treatment of intermediate G12 with an amine.

Intermediate N1

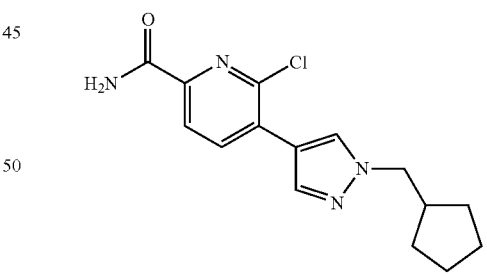

6-Chloro-5-(1-(cyclopentylmethyl)-1H-pyrazol-4-yl)picolinamide (Scheme N)

Methyl 6-chloro-5-(1-(cyclopentylmethyl)-1H-pyrazol-4-yl)picolinate was suspended in $NH_3$ (7 N in MeOH, 14.27 mL) in a pressure vial. The reaction was stirred at RT for 2 h. Excess solvent was removed under reduced pressure to yield the title compound. MS: 305 (M+1). The following intermediate in table N was prepared according to scheme N using the procedure outlined in the synthesis intermediate N1 using methyl amine. MS: 305 (M+1).

TABLE N

| Intermediate | Structure | Name | MS (M + 1) |
|---|---|---|---|
| N2 | 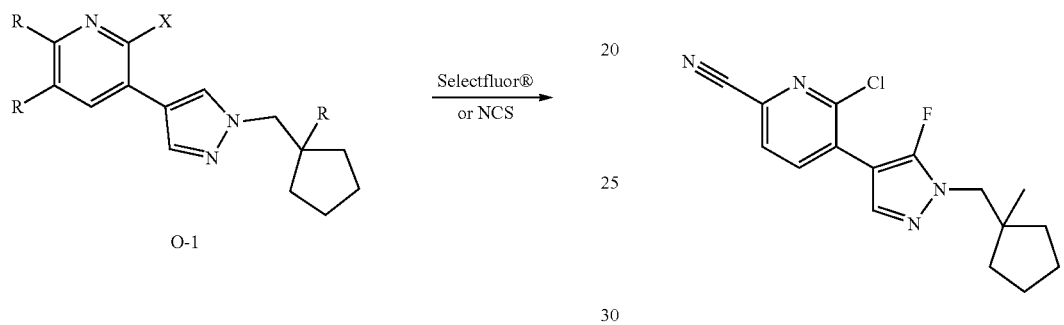 | 6-chloro-5-(1-(cyclopentylmethyl)-1H-pyrazol-4-yl)-N-methylpicolinamide | 319 |

SCHEME O

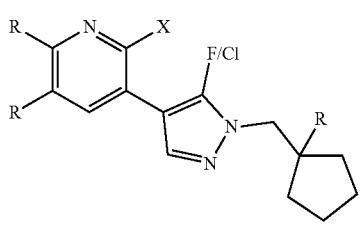

Intermediate O is prepared according to scheme O by treatment of intermediate G1 with Selectfluor® or NCS to result in the pyrazole halogenation.

Intermediate O1

6-Chloro-5-(5-fluoro-1-((1-methylcyclopentyl)methyl)-1H-pyrazol-4-yl)picolinonitrile (Scheme O)

Selectfluor® (464 mg, 1.309 mmol) was added to a mixture of 6-chloro-5-(1-((1-methylcyclopentyl)methyl)-1H-pyrazol-4-yl)picolinonitrile (intermediate G1, 358 mg, 1.19 mmol) in MeCN (4 mL) and the mixture was stirred at 165° C. under microwave irradiation for 30 min. The reaction mixture was concentrated and the residue was purified by column chromatography on silica gel (15:1 EtOAc: isohexane) to give the title compound. MS: 319 (M+1). The following intermediates in table O were prepared according to scheme O using the procedure outlined in the synthesis intermediate O1 using prepared intermediates (from table G) or untilizing alternative conditions using N-chlorosuccinimide at 100° C. (microwave irradiation) to yield the corresponding chloropyrazole product.

TABLE O

| Intermediate | Structure | Name | MS (M + 1) |
|---|---|---|---|
| O2 | 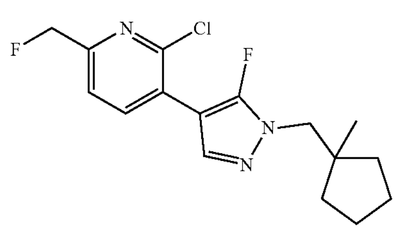 [SMILES: CC1(Cn2ncc(-c3ccc(CF)nc3Cl)c2F)CCCC1] | 2-chloro-3-(5-fluoro-1-((1-methylcyclopentyl)methyl)-1H-pyrazol-4-yl)-6-(fluoromethyl)pyridine | 326 |

TABLE O-continued

| Intermediate | Structure | Name | MS (M + 1) |
|---|---|---|---|
| O3 | 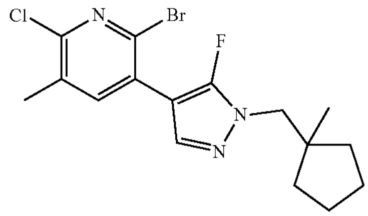 [SMILES: Cc1cc(-c2cnn(CC3(C)CCCC3)c2F)c(Br)nc1Cl] | 2-bromo-6-chloro-3-(5-fluoro-1-((1-methylcyclopentyl)methyl)-1H-pyrazol-4-yl)-5-methylpyridine | 386, 388 |
| O4 | 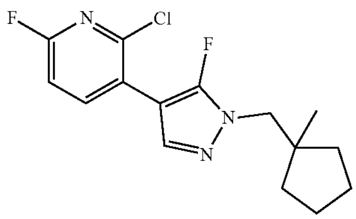 [SMILES: CC1(Cn2ncc(-c3ccc(F)nc3Cl)c2F)CCCC1] | 2-chloro-6-fluoro-3-(5-fluoro-1-((1-methylcyclopentyl)methyl)-1H-pyrazol-4-yl)pyridine | 312 |
| O5 | 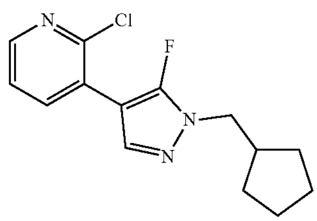 [SMILES: Fc1c(-c2cccnc2Cl)cnn1CC1CCCC1] | 2-chloro-3-(1-(cyclopentylmethyl)-5-fluoro-1H-pyrazol-4-yl)pyridine | 280 |
| O6 | 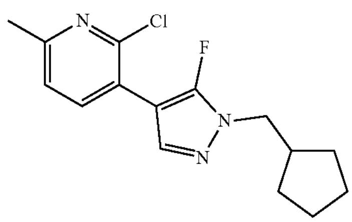 [SMILES: Cc1ccc(-c2cnn(CC3CCCC3)c2F)c(Cl)n1] | 2-chloro-3-(1-(cyclopentylmethyl)-5-fluoro-1H-pyrazol-4-yl)-6-methylpyridine | 294 |
| O7 | 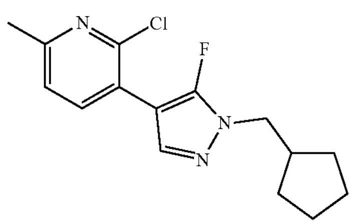 [SMILES: Cc1ccc(-c2cnn(CC3CCCC3)c2F)c(Cl)n1] | 2-chloro-3-(5-fluoro-1-((1-methylcyclopentyl)methyl)-1H-pyrazol-4-yl)-6-methylpyridine | 308 |
| O8 | 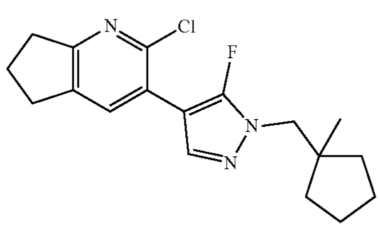 [SMILES: CC1(Cn2ncc(-c3cc4c(nc3Cl)CCC4)c2F)CCCC1] | 2-chloro-3-(5-fluoro-1-((1-methylcyclopentyl)methyl)-1H-pyrazol-4-yl)-6,7-dihydro-5H-cyclopenta[b]pyridine | 334 |
| O9 | 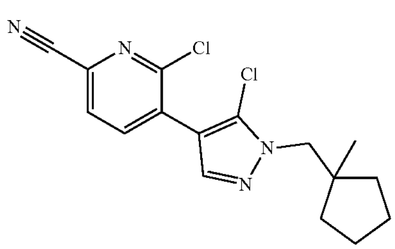 [SMILES: CC1(Cn2ncc(-c3ccc(C#N)nc3Cl)c2Cl)CCCC1] | 6-chloro-5-(5-chloro-1-((1-methylcyclopentyl)methyl)-1H-pyrazol-4-yl)picolinonitrile | 335, 337 |

SCHEME P

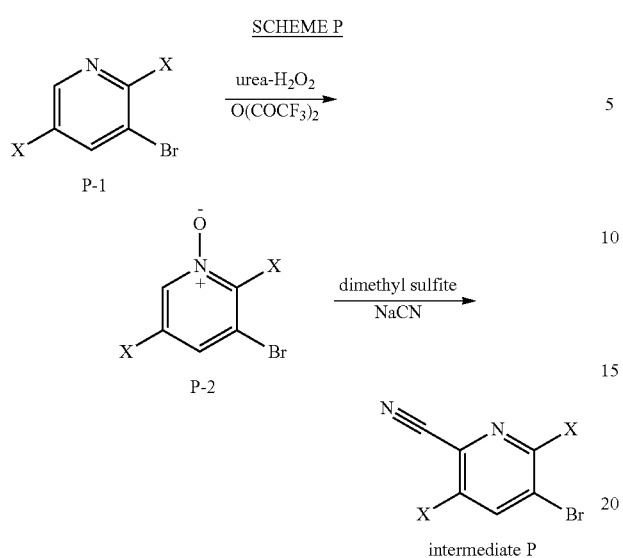

Intermediate P is prepared according to scheme P beginning with commercial pyridine P-1. Oxidation with urea-.hydrogen peroxide in the presence of trifluoroacetic anhydride provides N-oxide P-2. Subsequent o-methylation with dimethyl sulfide followed by Reissert-Kaufmann reaction with sodium cyanide affords intermediate P.

Intermediate P

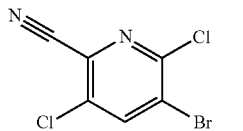

5-Bromo-3,6-dichloropicolinonitrile (Scheme P)

Step 1: 3-Bromo-2,5-dichloropyridine 1-oxide

To a solution of urea-hydrogen peroxide (4.98 g, 52.9 mmol) in DCM (20 mL) was added 2,2,2-trifluoroacetic anhydride (11.11 g, 52.9 mmol) under nitrogen atmosphere. The mixture was stirred at 50° C. for 0.5 h, before 3-bromo-2,5-dichloropyridine (2 g, 8.81 mmol) was added. After stirring at 50° C. for 1 h, the reaction was quenched with aqueous saturated $Na_2SO_3$ (100 mL) and partitioned with EtOAc (50 mL×2). The combined organic layers were washed with brine (50 mL×2), dried over anhydrous $Na_2SO_4$ and concentrated to give the title compound. This crude material was used without further purification. $^1$H NMR (400 MHz, methanol-$d_4$): δ 8.66 (d, J=2.0 Hz, 1H), 7.98 (d, J=2.0 Hz, 1H).

Step 2: 5-Bromo-3,6-dichloropicolinonitrile

A solution of 3-bromo-2,5-dichloropyridine 1-oxide (500 mg, 2.06 mmol) in dimethyl sulfite (11.5 g, 104 mmol) was stirred at 100° C. for 1 h under nitrogen atmosphere. The mixture was cooled to 0° C., and water (5 mL) and cyanosodium (1.79 g, 36.5 mmol) were added. The reaction was stirred at RT for 12 h and upon completion was diluted with water (10 mL) and extracted with EtOAc (20 mL×2). The combined organics were washed with brine (30 mL×2), dried over anhydrous $Na_2SO_4$, filtered and concentrated under reduced pressure. The resultant residue was purified by silica gel chromatography (1%-10% EtOAc/petroleum ether) to give the title compound. $^1$H NMR (400 MHz, methanol-$d_4$,): δ 8.59 (s, 1H).

SCHEME Q

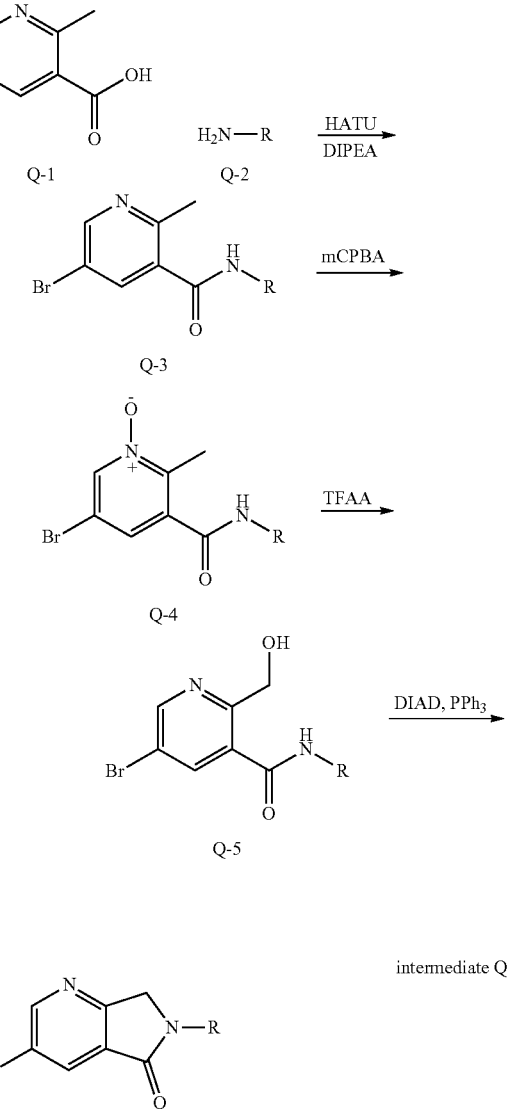

Intermediate Q is prepared according to scheme Q from commercial acid Q-1 and amine Q-2, which is transformed under the action of HATU to form the corresponding amide Q-3. Oxidation with m-CPBA provides N-oxide Q-4 which undergoes rearrangement in the presence of trifluoroacetic anhydride to benzyl alcohol Q-5. Intramolecular ring-closure under Mitsunobu conditions affords intermediate Q.

Intermediate Q

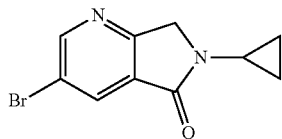 [SMILES: O=C1c2cc(Br)cnc2CN1C1CC1]

3-Bromo-6-cyclopropyl-6,7-dihydro-5H-pyrrolo[3,4-b]pyridin-5-one (Scheme Q)

Step 1:
5-Bromo-N-cyclopropyl-2-methylnicotinamide

5-Bromo-2-methylnicotinic acid (1.0 g, 4.63 mmol) was dissolved in DMF (11.6 mL). To this mixture was added HATU (2.20 g, 5.79 mmol), cyclopropanamine (0.48 mL, 6.94 mmol) and DIPEA (1.62 mL, 9.26 mmol). After stirring for 2 h at RT, the reaction was partitioned with ethyl acetate and saturated aqueous NH$_4$Cl. The organic was separated, washed with saturated aqueous NaHCO$_3$, brine, dried over anhydrous sodium sulfate, filtered and evaporated to dryness. The title compound was used without further purification. MS: 255, 257 (M+1).

Step 2:
5-Bromo-3-(cyclopropylcarbamoyl)-2-methylpyridine 1-oxide

To a solution of 5-bromo-N-cyclopropyl-2-methylnicotinamide (255 mg, 1.00 mmol) in CH$_2$Cl$_2$ (7.5 mL) was added m-CPBA (296 mg, 1.20 mmol). The reaction was stirred for 2.5 h at RT and then m-CPBA (47 mg, 0.27 mmol) was added. After 15 min, the reaction was diluted with additional CH$_2$Cl$_2$ and quenched with saturated aqueous NaHCO$_3$. The organic was separated, washed with saturated aqueous NaHCO$_3$ (2×), brine, dried over anhydrous sodium sulfate, filtered and concentrated. The title compound was used without further purification. MS: 271, 273 (M+1).

Step 3: 5-Bromo-N-cyclopropyl-2-(hydroxymethyl)nicotinamide

TFAA (0.165 mL, 1.171 mmol) was added dropwise to a solution of 5-bromo-3-(cyclopropylcarbamoyl)-2-methylpyridine 1-oxide (127 mg, 0.468 mmol) in DCM (1.0 mL). After 8 h at RT, the reaction was heated to 50° C. for 3 h. The solvent was removed under reduced pressure and then the residue was dissolved in a mixture of DCM (7.5 mL) and Na$_2$CO$_3$ (2 M in water, 20 mL). After stirring for 3 h, the organic was separated then dried over anhydrous sodium sulfate, filtered and concentrated. The crude material was purified by silica gel chromatography (10-80% 3:1 EtOAc:EtOH/hexanes) to afford the title compound. MS: 271, 273 (M+1).

Step 4: 3-Bromo-6-cyclopropyl-6,7-dihydro-5H-pyrrolo[3,4-b]pyridin-5-one

To a solution of 5-bromo-N-cyclopropyl-2-(hydroxymethyl)nicotinamide (19.1 mg, 0.070 mmol) in THF (470 µL) was added Ph$_3$P (22.2 mg, 0.085 mmol), followed by dropwise addition of DIAD (15.07 µL, 0.077 mmol). After 1 h, the solvent was removed under reduced pressure and the crude residue was purified by silica gel chromatography (20-100% EtOAc/hexanes). MS: 253, 255 (M+1).

SCHEME R

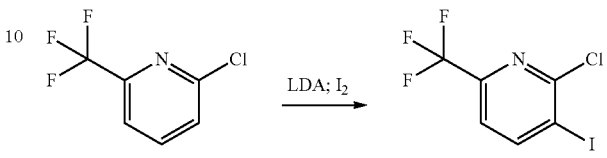

Intermediate R is prepared according to scheme R via deprotonation of commercial pyridine R-1 in the presence of iodine.

Intermediate R

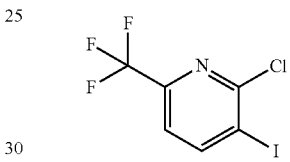

2-Chloro-3-iodo-6-(trifluoromethyl)pyridine
(Scheme R)

To a solution of 2-chloro-6-(trifluoromethyl)pyridine (5 g, 27.5 mmol) in THF (100 mL) was added lithium diisopropylamide (2 M in THF, 15.2 mL, 30.3 mmol) dropwise at −78° C. The reaction was stirred for 30 min at −78° C., then a solution of iodine (8.39 g, 33.1 mmol) in THF (50 mL) was added dropwise to the mixture. After the addition was complete, the reaction was allowed to warm to RT and was stirred for 12 h. The reaction was quenched with water (25 mL), extracted with ethyl acetate (250 mL×3) and the combined organic layers were dried over sodium sulfate and concentrated in vacuo. The resultant residue was purified by silica gel chromatography (100:1 petroleum ether/EtOAc) to give the title compound. $^1$H NMR (400 MHz, CDCl$_3$): δ 8.28 (d, J=8.0 Hz, 1H), 7.25 (d, J=7.6 Hz, 1H).

SCHEME S

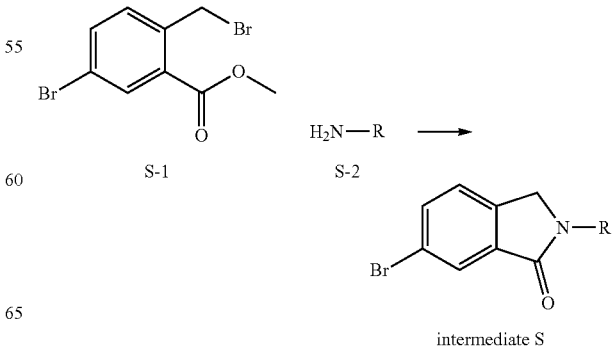

intermediate S

Intermediate S is prepared according to scheme S from commercial ester S-1 and amine S-2, which cyclize to a lactam to form intermediate S.

Intermediate S

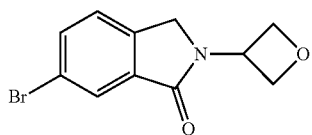 [SMILES: O=C1c2cc(Br)ccc2CN1C1COC1]

6-bromo-2-(oxetan-3-yl)isoindolin-1-one (Scheme S)

A mixture of methyl 5-bromo-2-(bromomethyl)benzoate (300 mg, 1.02 mmol) and oxetan-3-amine (223 mg, 3.06 mmol) were stirred in a solution of DCM (6 mL) at RT for 18 h. The reaction was worked-up with water (50 mL) and extracted with additional DCM (30 mL×2). The combined organics were dried over sodium sulfate and was concentrated to dryness. The resultant material was of sufficient purity to use without further purification. MS: 268, 270 (M+1).

SCHEME T

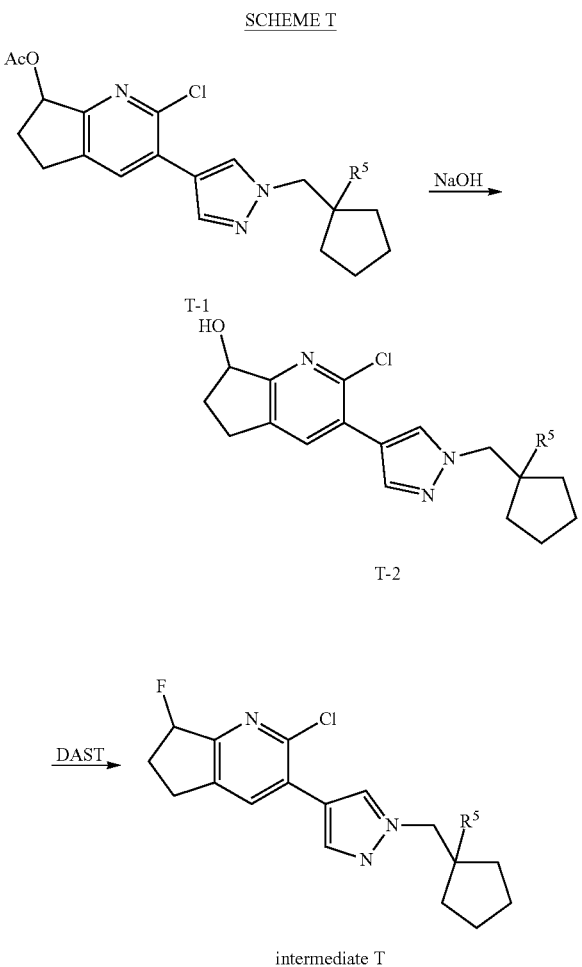

intermediate T

Intermediate T is prepared after deacylation of prepared acetate T-1 followed by reaction of alcohol T-2 with DAST.

Intermediate T

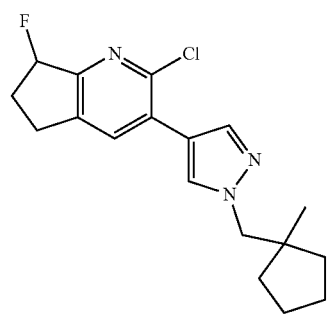 [SMILES: CC1(Cn2cc(-c3cc4c(nc3Cl)C(F)CC4)cn2)CCCC1]

2-Chloro-7-fluoro-3-(1-((1-methylcyclopentyl)methyl)-1H-pyrazol-4-yl)-6,7-dihydro-5H-cyclopenta[b]pyridine (Scheme T)

Step 1: 2-Chloro-3-(1-((1-methylcyclopentyl)methyl)-1H-pyrazol-4-yl)-6,7-dihydro-5H-cyclopenta[b]pyridin-7-ol To a stirred solution of 2-chloro-3-(1-((1-methylcyclopentyl)methyl)-1H-pyrazol-4-yl)-6,7-dihydro-5H-cyclopenta[b]pyridin-7-yl acetate (intermediate G18, 200 mg, 0.535 mmol) in MeOH (5 mL) was added NaOH (42.8 mg, 1.070 mmol). The reaction mixture was stirred for 1 h at 20° C. before volatiles were removed under reduced pressure. The residue dissolved in 5/1 EtOAc/MeOH (12 mL). The mixture was stirred for 10 min, filtered and the filtrate was concentrated in vacuo and purified by prep-TLC (1:1 petroleum ether: EtOAc) to afford the title compound. MS: 332 (M+1).

Step 2: 2-Chloro-7-fluoro-3-(1-((1-methylcyclopentyl)methyl)-1H-pyrazol-4-yl)-6,7-dihydro-5H-cyclopenta[b]pyridine To a stirred solution of 2-chloro-3-(1-((1-methylcyclopentyl)methyl)-1H-pyrazol-4-yl)-6,7-dihydro-5H-cyclopenta[b]pyridin-7-ol (80 mg, 0.241 mmol) in DCM (3 mL) was added DAST (0.048 mL, 0.362 mmol) at 0° C. for 1 h. The reaction mixture was concentrated in vacuo and the residue was dissolved in 5:1 EtOAc/MeOH (12 mL). The mixture was stirred for 10 min, filtered and the filtrate was concentrated in vacuo. Purification by prep-TLC (1:1 petroleum ether:EtOAc) provided the title compound. MS: 344 (M+1).

EXAMPLES

Example compounds of the present invention can be synthesized according to the schemes and procedures outlined below. Because the schemes are an illustration, the invention should not be construed as being limited by the chemical reactions and conditions expressed. The preparation of the various starting materials used in the schemes is within the skill of a person versed in the art. Absolute

Example 1

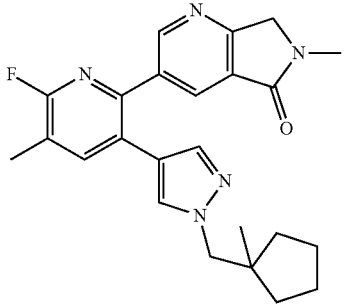 [SMILES: Cc1cc(-c2cnn(CC3(C)CCCC3)c2)c(-c2cnc3c(c2)C(=O)N(C)C3)nc1F]

3-(6-Fluoro-5-methyl-3-(1-((1-methylcyclopentyl)methyl)-1H-pyrazol-4-yl)pyridin-2-yl)-6-methyl-6,7-dihydro-5H-pyrrolo[3,4-b]pyridin-5-one To a solution of 2-chloro-6-fluoro-5-methyl-3-(1-((1-methylcyclopentyl)methyl)-1H-pyrazol-4-yl)pyridine (intermediate G13, 50 mg, 0.162 mmol) in 1,4-dioxane (4 mL) and water (1 mL) was added 6-methyl-3-(4,4,5,5-tetramethyl-1,3,2-dioxaborolan-2-yl)-6,7-dihydro-5H-pyrrolo[3,4-b]pyridin-5-one (intermediate C10, 44.5 mg, 0.162 mmol), $K_3PO_4$ (43.3 mg, 0.162 mmol), and $PdCl_2$(dppf)-$CH_2Cl_2$ adduct (133 mg, 0.162 mmol). The system was degassed and placed under a $N_2$ (g) atmosphere. The mixture was stirred 2 h at 60° C. After cooling to RT, the reaction was diluted with brine (5 mL) and was extracted with EtOAc (3×10 mL). The combined organic was dried with anhydrous sodium sulfate and was concentrated under reduced pressure. The crude material was purified by reverse phase HPLC (ACN/water with 0.1% $NH_3OH$ modifier) to yield the title compound. MS: 420 (M+1). $^1$H NMR (400 MHz, $CDCl_3$): δ 8.62 (1H, d, J=1.6 Hz), 8.08 (1H, d, J=1.6 Hz), 7.61 (1H, d, J=9.2 Hz), 7.19 (1H, s), 7.25 (1H, s), 6.92 (1H, s), 4.38 (2H, s), 3.82 (2H, s), 3.16 (3H, s), 3.30 (3H, s), 1.45-1.6 (4H, m), 1.30-1.40 (2H, m), 1.15-1.25 (2H, m), 0.78 (3H, s).

Examples 1A and 1B

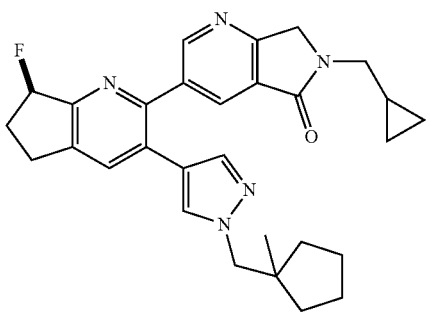

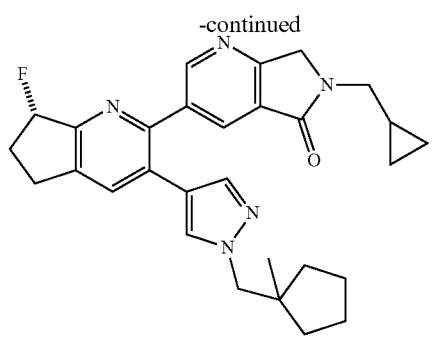

(R)-6-(cyclopropylmethyl)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridine-5-one and (S)-6-(cyclopropylmethyl)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one To a solution of 2-chloro-7-fluoro-3-(1-((1-methylcyclopentyl)methyl)-1H-pyrazol-4-yl)-6,7-dihydro-5H-cyclopenta[b]pyridine (intermediate T, 80 mg, 0.240 mmol), 6-(cyclopropylmethyl)-3-(4,4,5,5-tetramethyl-1,3,2-dioxaborolan-2-yl)-5H-pyrrolo[3,4-b]pyridin-7(6H)-one (intermediate C14, 75 mg, 0.240 mmol) and tripotassium phosphate trihydrate TRIHYDRATE (191 mg, 0.719 mmol) in dioxane (4 mL) and water (1 mL) was added 1,1'-bis(di-tert-butylphosphino)ferrocene palladium dichloride (1.562 mg, 2.396 μmol). The resulting mixture was stirred at 80° C. for 2 h under an atmosphere of nitrogen. The mixture was cooled to RT and then diluted with water (10 mL) and extracted with EtOAc (10 mL×3). The combined organic layers were washed with brine (30 mL), dried over anhydrous sodium sulfate, filtered, and concentrated in vacuo. The residue was purified by prep-TLC (80% EtOAc in hexanes) to give the racemate. The material was then purified by chiral SFC (AD column, 55% EtOH/$CO_2$) to afford Example 1A (faster eluting isomer): MS: 486 (M+1). $^1$H NMR (400 MHz, $CDCl_3$): δ 8.78 (1H, s), 8.18 (1H, s), 7.74 (1H, s), 7.27 (1H, s), 6.98 (1H, s), 5.99 (1H, dd, J=28.0, 4.4 Hz), 4.57 (2H, s), 3.88 (2H, s), 3.53 (2H, d, J=7.2 Hz), 3.25-3.35 (1H, m), 2.95-3.05 (1H, m), 2.45-2.64 (2H, m), 1.61 (4H, br s), 1.40-1.47 (2H, m), 1.20-1.35 (2H, m), 1.09 (1H, br s), 0.84 (3H, s), 0.60-0.70 (2H, m), 0.35-0.45 (2H, m) and Example 1B (slower eluting isomer): MS: 486 (M+1). $^1$H NMR (400 MHz, $CDCl_3$): δ 8.78 (1H, s), 8.18 (1H, s), 7.74 (1H, s), 7.31 (1H, s), 6.97 (1H, s), 5.99 (1H, dd, J=28.0, 4.4 Hz), 4.57 (2H, s), 3.89 (2H, s), 3.53 (2H, d, J=7.2 Hz), 3.25-3.35 (1H, m), 2.95-3.05 (1H, m), 2.45-2.64 (2H, m), 1.61 (4H, brs), 1.40-1.47 (2H, m), 1.20-1.35 (2H, m), 1.091 (1H, brs), 0.84 (3H, s), 0.60-0.70 (2H, m), 0.36-0.45 (2H, m).

Example 2

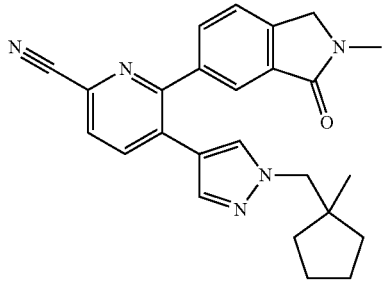 [SMILES: CN1Cc2ccc(-c3nc(C#N)ccc3-c3cnn(CC4(C)CCCC4)c3)cc2C1=O]

6-(2-Methyl-3-oxoisoindolin-5-yl)-5-(1-((1-methyl-cyclopentyl)methyl)-1H-pyrazol-4-yl)picolinonitrile
(Scheme 1)

To 2-methyl-6-(4,4,5,5-tetramethyl-1,3,2-dioxaborolan-2-yl)isoindolin-1-one (intermediate C1, 545 mg, 2.0 mmol), 6-chloro-5-(1-((1-methylcyclopentyl)methyl)-1H-pyrazol-4-yl)picolinonitrile (intermediate G1, 500 mg, 1.66 mmol), potassium carbonate (1 M in water, 4.99 mL, 4.99 mmol) and THF (8.3 mL) was added to a vial under an atmosphere of $N_{2\ (g)}$. 1,1'-Bis(di-tert-butylphosphino)ferrocene palladium dichloride (87 mg, 0.133 mmol) was added and the system was a purged and flushed with $N_2$ (g) and it was stirred at 60° C. for 5 hr. After cooling to RT, the reaction was diluted with water and was extracted with EtOAc. The organic was dried with anhydrous sodium sulfate and was concentrated under reduced pressure. The crude material was purified by silica gel column (0-60% 3:1 EtOAc:EtOH/hexanes) to yield the title compound. MS: 412 (M+1). $^1$H NMR (500 MHz, CDCl$_3$): δ 7.87-7.89 (m, 2H), 7.67 (d, J=8.02 Hz, 1H), 7.59 (dd, J=7.77, 1.67 Hz, 1H), 7.45 (d, J=7.78 Hz, 1H), 7.31 (s, 1H), 6.89 (s, 1H), 4.39 (s, 3H), 3.83 (s, 2H), 3.19 (s, 3H), 1.52-1.61 (m, 4H), 1.36-1.41 (m, 2H), 1.19-1.24 (m, 2H), 0.80 (s, 3H).

The following compounds were prepared according to the general procedure provided in the examples and procedures herein using known or prepared pyridyl chlorides or bromides with known or prepared boronic esters or acids, as described in the reaction schemes and examples herein. The requisite starting materials are either prepared as described in the intermediates section, commercially available, or may be prepared from commercially available reagents using conventional reactions well known in the art without undue experimentation. The reaction can be performed with either 1,1'-bis(diphenylphosphino)ferrocene palladium(II)dichloride dichloromethane complex 1,1'-bis(di-tert-butylphosphino)ferrocene palladium dichloride as using conditions outlined in Examples 1, 1A, 1B and 2 with the reaction temperature ranging from room temperature to 110° C. as appropriate for each substrate.

TABLE 1

| Example | Structure | Name | MS (M + 1) |
|---|---|---|---|
| 3 | 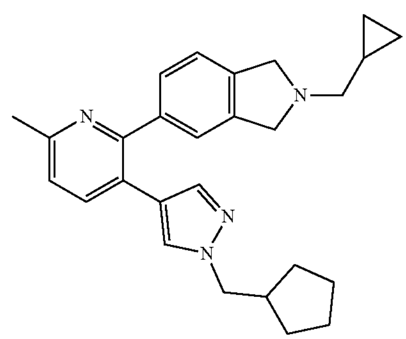 [SMILES: Cc1ccc(-c2cnn(CC3CCCC3)c2)c(-c2ccc3c(c2)CN(CC2CC2)C3)n1] | 6-(3-(1-(cyclopentylmethyl)-1H-pyrazol-4-yl)-6-methylpyridin-2-yl)-2-(cyclopropylmethyl)isoindolin-1-one | 427 |
| 4 | 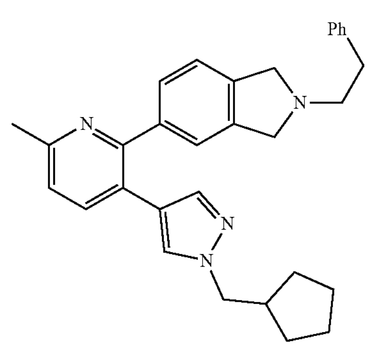 [SMILES: Cc1ccc(-c2cnn(CC3CCCC3)c2)c(-c2ccc3c(c2)CN(CCc2ccccc2)C3)n1] | 6-(3-(1-(cyclopentylmethyl)-1H-pyrazol-4-yl)-6-methylpyridin-2-yl)-2-phenethylisoindolin-1-one | 477 |

TABLE 1-continued

| Example | Structure | Name | MS (M + 1) |
|---|---|---|---|
| 5 | 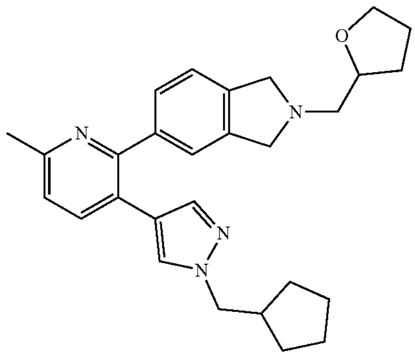 [SMILES: Cc1ccc(-c2cnn(CC3CCCC3)c2)c(-c2ccc3c(c2)CN(CC2CCCO2)C3)n1] | 6-(3-(1-(cyclopentylmethyl)-1H-pyrazol-4-yl)-6-methylpyridin-2-yl)-2-((tetrahydrofuran-2-yl)methyl)isoindolin-1-one | 457 |
| 6 | 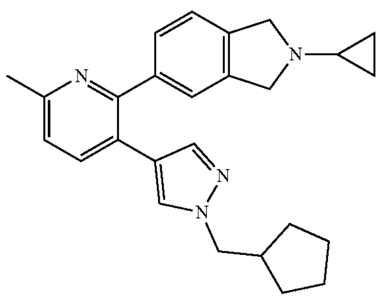 [SMILES: Cc1ccc(-c2cnn(CC3CCCC3)c2)c(-c2ccc3c(c2)CN(C2CC2)C3)n1] | 6-(3-(1-(cyclopentylmethyl)-1H-pyrazol-4-yl)-6-methylpyridin-2-yl)-2-cyclopropylisoindolin-1-one | 413 |
| 7 | 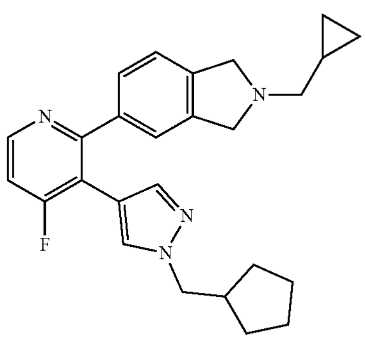 [SMILES: Fc1ccnc(-c2ccc3c(c2)CN(CC2CC2)C3)c1-c1cnn(CC2CCCC2)c1] | 6-(3-(1-(cyclopentylmethyl)-1H-pyrazol-4-yl)-4-fluoropyridin-2-yl)-2-(cyclopropylmethyl)isoindolin-1-one | 431 |
| 8 | 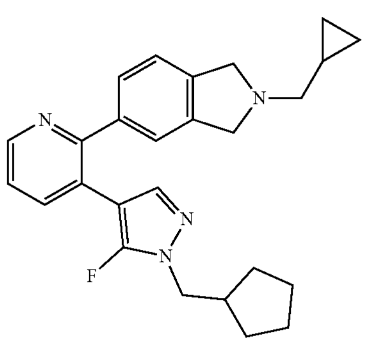 [SMILES: Fc1c(-c2cccnc2-c2ccc3c(c2)CN(CC2CC2)C3)cnn1CC1CCCC1] | 6-(3-(1-(cyclopentylmethyl)-5-fluoro-1H-pyrazol-4-yl)pyridin-2-yl)-2-(cyclopropylmethyl)isoindolin-1-one | 431 |

TABLE 1-continued

| Example | Structure | Name | MS (M + 1) |
|---|---|---|---|
| 9 | 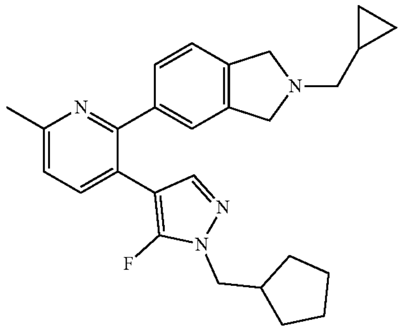 [SMILES: Cc1ccc(-c2cnn(CC3CCCC3)c2F)c(-c2ccc3c(c2)CN(CC2CC2)C3)n1] | 6-(3-(1-(cyclopentylmethyl)-5-fluoro-1H-pyrazol-4-yl)-6-methylpyridin-2-yl)-2-(cyclopropylmethyl)isoindolin-1-one | 445 |
| 10 | 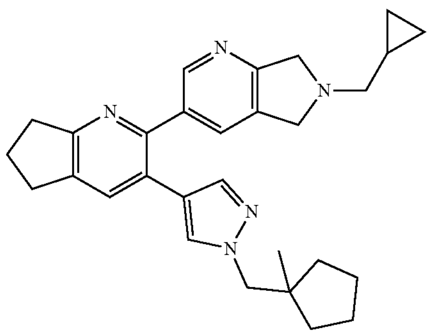 [SMILES: CC1(Cn2cc(-c3cc4c(nc3-c3cnc5c(c3)CN(CC3CC3)C5)CCC4)cn2)CCCC1] | 6-(cyclopropylmethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 468 |
| 11 | 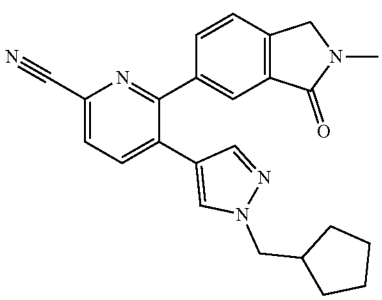 [SMILES: CN1Cc2ccc(-c3nc(C#N)ccc3-c3cnn(CC4CCCC4)c3)cc2C1=O] | 5-(1-(cyclopentylmethyl)-1H-pyrazol-4-yl)-6-(2-methyl-3-oxoisoindolin-5-yl)picolinonitrile | 398 |
| 12 | 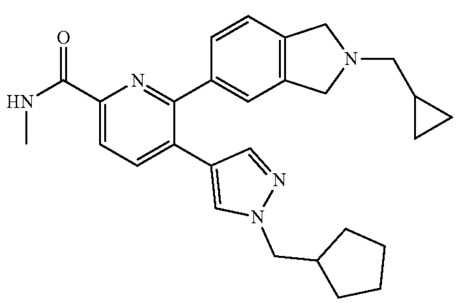 [SMILES: CNC(=O)c1ccc(-c2cnn(CC3CCCC3)c2)c(-c2ccc3c(c2)CN(CC2CC2)C3)n1] | 5-(1-(cyclopentylmethyl)-1H-pyrazol-4-yl)-6-(2-(cyclopropylmethyl)-3-oxoisoindolin-5-yl)-N-methylpicolinamide | 470 |
| 13 | 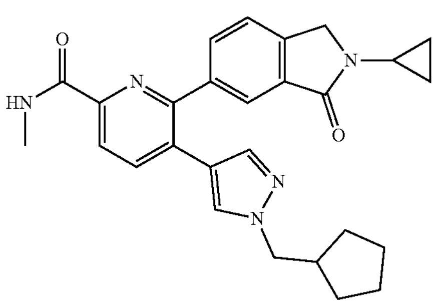 [SMILES: CNC(=O)c1ccc(-c2cnn(CC3CCCC3)c2)c(-c2ccc3c(c2)C(=O)N(C2CC2)C3)n1] | 5-(1-(cyclopentylmethyl)-1H-pyrazol-4-yl)-6-(2-cyclopropyl-3-oxoisoindolin-5-yl)-N-methylpicolinamide | 456 |

TABLE 1-continued

| Example | Structure | Name | MS (M + 1) |
|---|---|---|---|
| 14 | 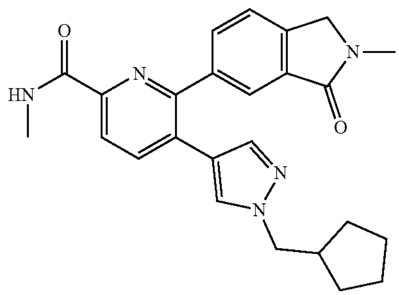 [SMILES: CNC(=O)c1ccc(-c2cnn(CC3CCCC3)c2)c(-c2ccc3c(c2)C(=O)N(C)C3)n1] | 5-(1-(cyclopentylmethyl)-1H-pyrazol-4-yl)-N-methyl-6-(2-methyl-3-oxoisoindolin-5-yl)picolinamide | 430 |
| 15 | 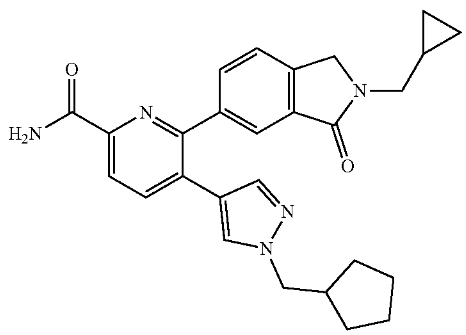 [SMILES: NC(=O)c1ccc(-c2cnn(CC3CCCC3)c2)c(-c2ccc3c(c2)C(=O)N(CC2CC2)C3)n1] | 5-(1-(cyclopentylmethyl)-1H-pyrazol-4-yl)-6-(2-(cyclopropylmethyl)-3-oxoisoindolin-5-yl)picolinamide | 456 |
| 16 | 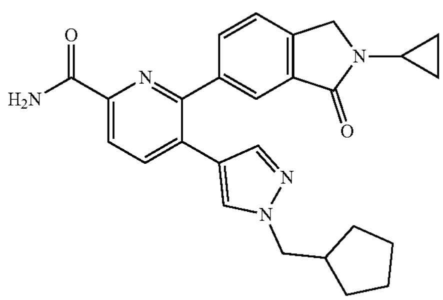 [SMILES: NC(=O)c1ccc(-c2cnn(CC3CCCC3)c2)c(-c2ccc3c(c2)C(=O)N(C2CC2)C3)n1] | 5-(1-(cyclopentylmethyl)-1H-pyrazol-4-yl)-6-(2-cyclopropyl-3-oxoisoindolin-5-yl)picolinamide | 442 |
| 17 | 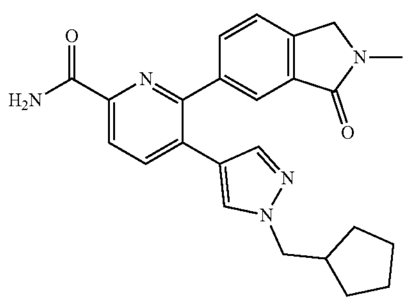 [SMILES: CN1Cc2ccc(-c3nc(C(N)=O)ccc3-c3cnn(CC4CCCC4)c3)cc2C1=O] | 5-(1-(cyclopentylmethyl)-1H-pyrazol-4-yl)-6-(2-methyl-3-oxoisoindolin-5-yl)picolinamide | 416 |
| 18 | 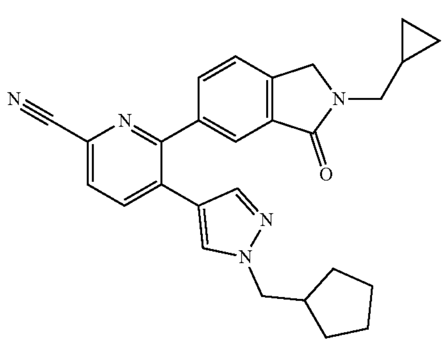 [SMILES: N#Cc1ccc(-c2cnn(CC3CCCC3)c2)c(-c2ccc3c(c2)C(=O)N(CC2CC2)C3)n1] | 5-(1-(cyclopentylmethyl)-1H-pyrazol-4-yl)-6-(2-(cyclopropylmethyl)-3-oxoisoindolin-5-yl)picolinonitrile | 438 |

TABLE 1-continued

| Example | Structure | Name | MS (M + 1) |
|---|---|---|---|
| 19 | 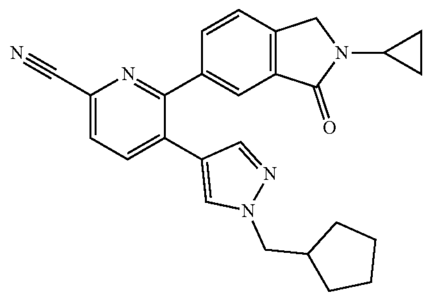 [SMILES: N#Cc1ccc(-c2cnn(CC3CCCC3)c2)c(-c2ccc3c(c2)C(=O)N(C2CC2)C3)n1] | 5-(1-(cyclopentylmethyl)-1H-pyrazol-4-yl)-6-(2-cyclopropyl-3-oxoisoindolin-5-yl)picolinonitrile | 424 |
| 20 | 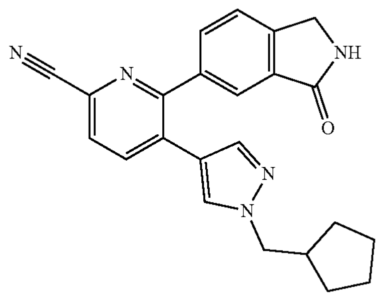 [SMILES: N#Cc1ccc(-c2cnn(CC3CCCC3)c2)c(-c2ccc3c(c2)C(=O)NC3)n1] | 5-(1-(cyclopentylmethyl)-1H-pyrazol-4-yl)-6-(3-oxoisoindolin-5-yl)picolinonitrile | 384 |
| 21 | 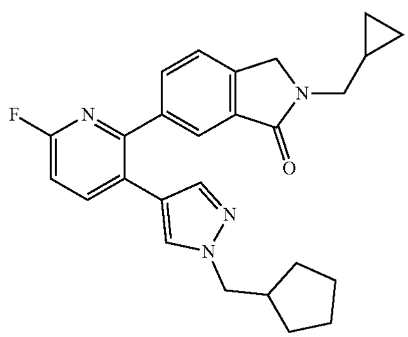 [SMILES: O=C1c2cc(-c3nc(F)ccc3-c3cnn(CC4CCCC4)c3)ccc2CN1CC1CC1] | 6-(3-(1-(cyclopentylmethyl)-1H-pyrazol-4-yl)-6-fluoropyridin-2-yl)-2-(cyclopropylmethyl)isoindolin-1-one | 431 |
| 22 | 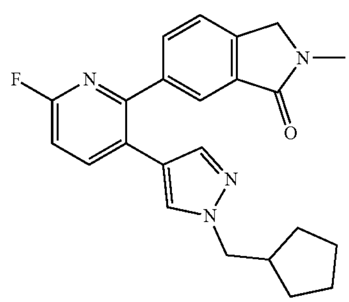 [SMILES: CN1Cc2ccc(-c3nc(F)ccc3-c3cnn(CC4CCCC4)c3)cc2C1=O] | 6-(3-(1-(cyclopentylmethyl)-1H-pyrazol-4-yl)-6-fluoropyridin-2-yl)-2-methylisoindolin-1-one | 391 |
| 23 | 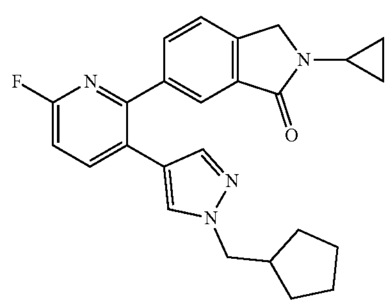 [SMILES: O=C1c2cc(-c3nc(F)ccc3-c3cnn(CC4CCCC4)c3)ccc2CN1C1CC1] | 6-(3-(1-(cyclopentylmethyl)-1H-pyrazol-4-yl)-6-fluoropyridin-2-yl)-2-cyclopropylisoindolin-1-one | 417 |

TABLE 1-continued

| Example | Structure | Name | MS (M + 1) |
|---|---|---|---|
| 24 | 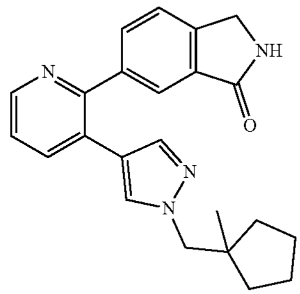 [SMILES: CC1(Cn2cc(-c3cccnc3-c3ccc4c(c3)C(=O)NC4)cn2)CCCC1] | 6-(3-(1-((1-methylcyclopentyl)methyl)-1H-pyrazol-4-yl)pyridin-2-yl)isoindolin-1-one | 373 |
| 25 | 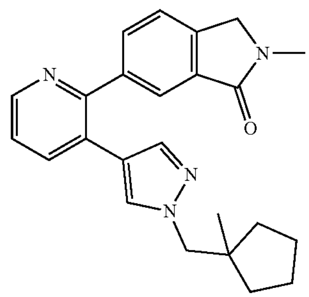 [SMILES: CN1Cc2ccc(-c3ncccc3-c3cnn(CC4(C)CCCC4)c3)cc2C1=O] | 2-methyl-6-(3-(1-((1-methylcyclopentyl)methyl)-1H-pyrazol-4-yl)pyridin-2-yl)isoindolin-1-one | 387 |
| 26 | 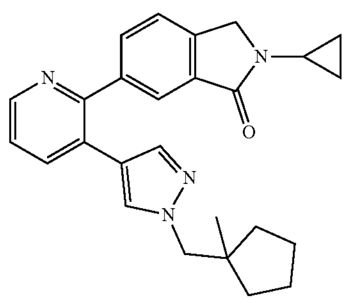 [SMILES: CC1(Cn2cc(-c3cccnc3-c3ccc4c(c3)C(=O)N(C3CC3)C4)cn2)CCCC1] | 2-cyclopropyl-6-(3-(1-((1-methylcyclopentyl)methyl)-1H-pyrazol-4-yl)pyridin-2-yl)isoindolin-1-one | 413 |
| 27 | 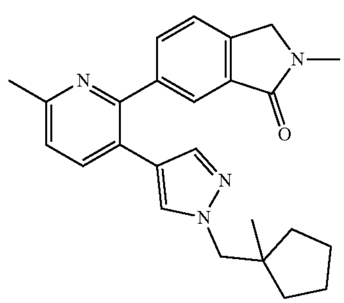 | 2-methyl-6-(6-methyl-3-(1-((1-methylcyclopentyl)methyl)-1H-pyrazol-4-yl)pyridin-2-yl)isoindolin-1-one | 401 |
| 28 | 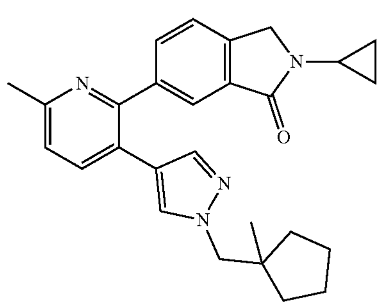 [SMILES: Cc1ccc(-c2cnn(CC3(C)CCCC3)c2)c(-c2ccc3c(c2)C(=O)N(C2CC2)C3)n1] | 2-cyclopropyl-6-(6-methyl-3-(1-((1-methylcyclopentyl)methyl)-1H-pyrazol-4-yl)pyridin-2-yl)isoindolin-1-one | 427 |

TABLE 1-continued

| Example | Structure | Name | MS (M + 1) |
|---|---|---|---|
| 29 | 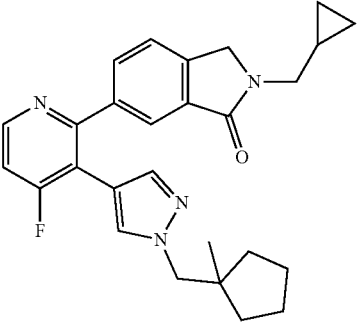 [SMILES: CC1(Cn2cc(-c3c(F)ccnc3-c3ccc4c(c3)C(=O)N(CC3CC3)C4)cn2)CCCC1] | 2-(cyclopropylmethyl)-6-(4-fluoro-3-(1-((1-methylcyclopentyl)methyl)-1H-pyrazol-4-yl)pyridin-2-yl)isoindolin-1-one | 445 |
| 30 | 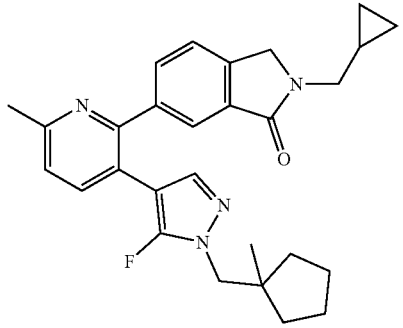 [SMILES: Cc1ccc(-c2cnn(CC3(C)CCCC3)c2F)c(-c2ccc3c(c2)C(=O)N(CC2CC2)C3)n1] | 2-(cyclopropylmethyl)-6-(3-(5-fluoro-1-((1-methylcyclopentyl)methyl)-1H-pyrazol-4-yl)-6-methylpyridin-2-yl)isoindolin-1-one | 459 |
| 31 | 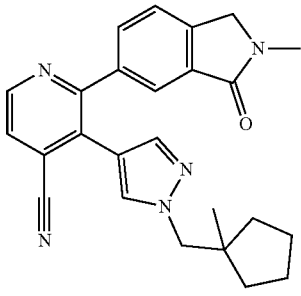 [SMILES: CN1Cc2ccc(-c3nccc(C#N)c3-c3cnn(CC4(C)CCCC4)c3)cc2C1=O] | 2-(2-methyl-3-oxoisoindolin-5-yl)-3-(1-((1-methylcyclopentyl)methyl)-1H-pyrazol-4-yl)isonicotinonitrile | 412 |
| 32 | 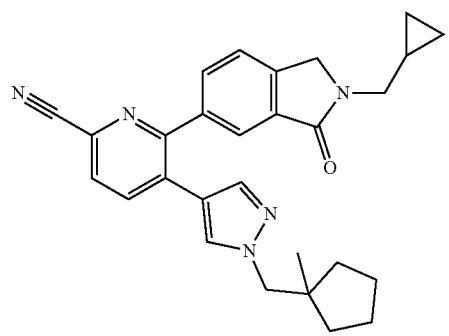 [SMILES: CC1(Cn2cc(-c3ccc(C#N)nc3-c3ccc4c(c3)C(=O)N(CC3CC3)C4)cn2)CCCC1] | 6-(2-(cyclopropylmethyl)-3-oxoisoindolin-5-yl)-5-(1-((1-methylcyclopentyl)methyl)-1H-pyrazol-4-yl)picolinonitrile | 452 |

TABLE 1-continued

| Example | Structure | Name | MS (M + 1) |
|---|---|---|---|
| 33 | 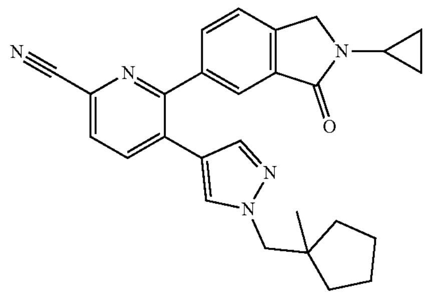 [SMILES: CC1(Cn2cc(-c3ccc(C#N)nc3-c3ccc4c(c3)C(=O)N(C3CC3)C4)cn2)CCCC1] | 6-(2-cyclopropyl-3-oxoisoindolin-5-yl)-5-(1-((1-methylcyclopentyl)methyl)-1H-pyrazol-4-yl)picolinonitrile | 438 |
| 34 | 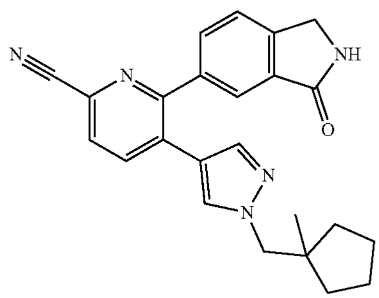 [SMILES: CC1(Cn2cc(-c3ccc(C#N)nc3-c3ccc4c(c3)C(=O)NC4)cn2)CCCC1] | 5-(1-((1-methylcyclopentyl)methyl)-1H-pyrazol-4-yl)-6-(3-oxoisoindolin-5-yl)picolinonitrile | 398 |
| 34A | 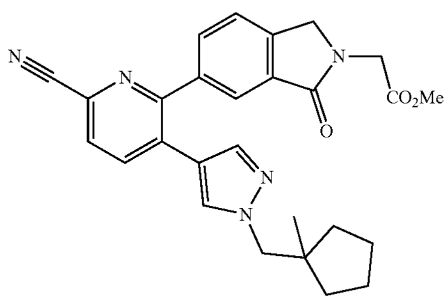 [SMILES: COC(=O)CN1Cc2ccc(-c3nc(C#N)ccc3-c3cnn(CC4(C)CCCC4)c3)cc2C1=O] | methyl 2-(6-(6-cyano-3-(1-((1-methylcyclopentyl)-methyl)-1H-pyrazol-4-yl)pyridin-2-yl)-1-oxoisoindolin-2-yl)acetate | 471 |
| 35 | 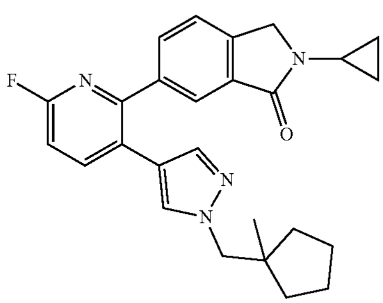 [SMILES: CC1(Cn2cc(-c3ccc(F)nc3-c3ccc4c(c3)C(=O)N(C3CC3)C4)cn2)CCCC1] | 2-cyclopropyl-6-(6-fluoro-3-(1-((1-methylcyclopentyl)methyl)-1H-pyrazol-4-yl)pyridin-2-yl)isoindolin-1-one | 431 |
| 36 | 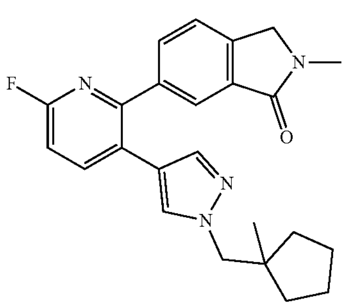 [SMILES: CN1Cc2ccc(-c3nc(F)ccc3-c3cnn(CC4(C)CCCC4)c3)cc2C1=O] | 6-(6-fluoro-3-(1-((1-methylcyclopentyl)methyl)-1H-pyrazol-4-yl)pyridin-2-yl)-2-methylisoindolin-1-one | 405 |

TABLE 1-continued

| Example | Structure | Name | MS (M + 1) |
|---|---|---|---|
| 37 | 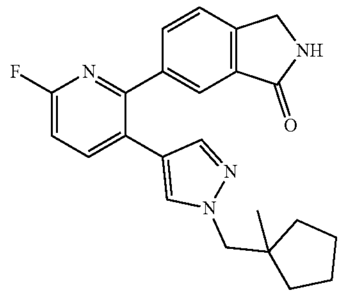 [SMILES: CC1(Cn2cc(-c3ccc(F)nc3-c3ccc4c(c3)C(=O)NC4)cn2)CCCC1] | 6-(6-fluoro-3-(1-((1-methylcyclopentyl)methyl)-1H-pyrazol-4-yl)pyridin-2-yl)isoindolin-1-one | 391 |
| 38 | 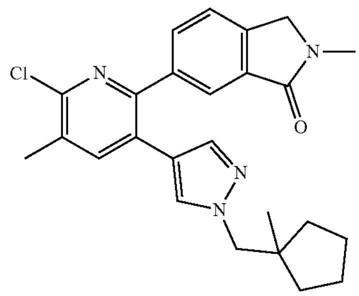 | 6-(6-chloro-5-methyl-3-(1-((1-methylcyclopentyl)methyl)-1H-pyrazol-4-yl)pyridin-2-yl)-2-methylisoindolin-1-one | 435 |
| 39 | 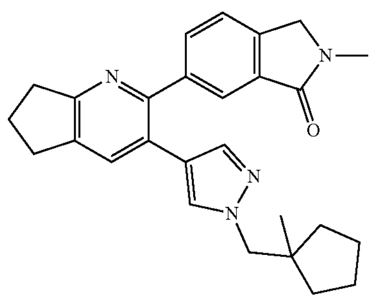 [SMILES: CN1Cc2ccc(-c3nc4c(cc3-c3cnn(CC5(C)CCCC5)c3)CCC4)cc2C1=O] | 2-methyl-6-(3-(1-((1-methylcyclopentyl)methyl)-1H-pyrazol-4-yl)-6,7-dihydro-5H-cyclopenta[b]pyridin-2-yl)isoindolin-1-one | 427 |
| 39A | 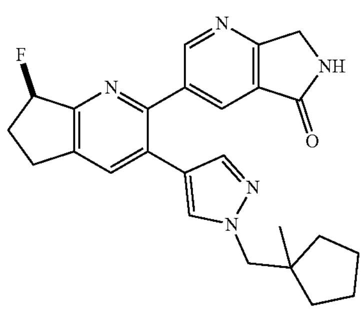 [SMILES: CC1(Cn2cc(-c3cc4c(nc3-c3cnc5c(c3)C(=O)NC5)[C@H](F)CC4)cn2)CCCC1] | (R)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 432 |
| 39B | 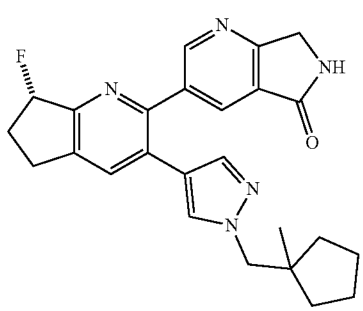 [SMILES: CC1(Cn2cc(-c3cc4c(nc3-c3cnc5c(c3)C(=O)NC5)[C@@H](F)CC4)cn2)CCCC1] | (S)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 432 |

TABLE 1-continued

| Example | Structure | Name | MS (M + 1) |
|---|---|---|---|
| 40 | 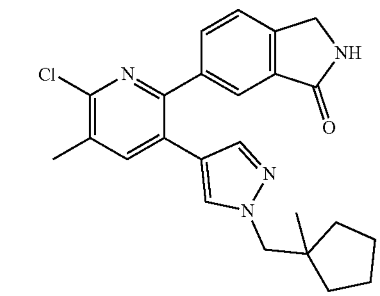 [SMILES: Cc1cc(-c2cnn(CC3(C)CCCC3)c2)c(-c2ccc3c(c2)C(=O)NC3)nc1Cl] | 6-(6-chloro-5-methyl-3-(1-((1-methylcyclopentyl)methyl)-1H-pyrazol-4-yl)pyridin-2-yl)isoindolin-1-one | 421 |
| 41 | 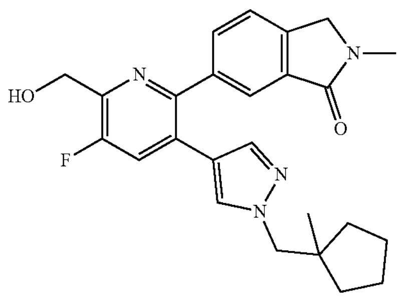 [SMILES: CN1Cc2ccc(-c3nc(CO)c(F)cc3-c3cnn(CC4(C)CCCC4)c3)cc2C1=O] | 6-(5-fluoro-6-(hydroxymethyl)-3-(1-((1-methylcyclopentyl)methyl)-1H-pyrazol-4-yl)pyridin-2-yl)-2-methylisoindolin-1-one | 435 |
| 42 | 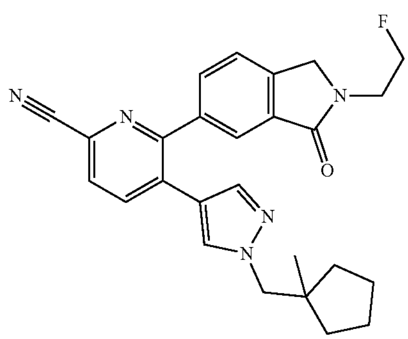 [SMILES: CC1(Cn2cc(-c3ccc(C#N)nc3-c3ccc4c(c3)C(=O)N(CCF)C4)cn2)CCCC1] | 6-(2-(2-fluoroethyl)-3-oxoisoindolin-5-yl)-5-(1-((1-methylcyclopentyl)methyl)-1H-pyrazol-4-yl)picolinonitrile | 444 |
| 43 | 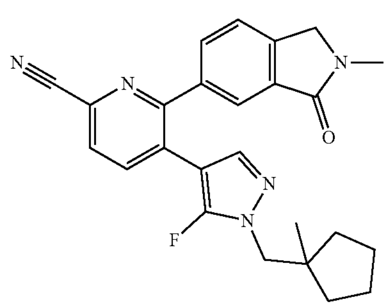 [SMILES: CN1Cc2ccc(-c3nc(C#N)ccc3-c3cnn(CC4(C)CCCC4)c3F)cc2C1=O] | 5-(5-fluoro-1-((1-methylcyclopentyl)methyl)-1H-pyrazol-4-yl)-6-(2-methyl-3-oxoisoindolin-5-yl)picolinonitrile | 430 |
| 43A | 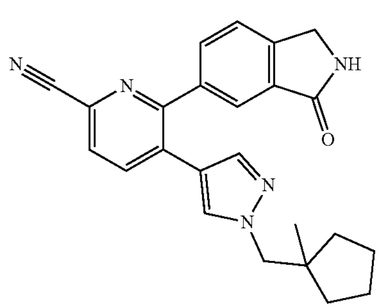 [SMILES: CC1(Cn2cc(-c3ccc(C#N)nc3-c3ccc4c(c3)C(=O)NC4)cn2)CCCC1] | 5-(5-fluoro-1-((1-methylcyclopentyl)methyl)-1H-pyrazol-4-yl)-6-(3-oxoisoindolin-5-yl)picolinonitrile | 416 |

TABLE 1-continued

| Example | Structure | Name | MS (M + 1) |
|---|---|---|---|
| 44 | 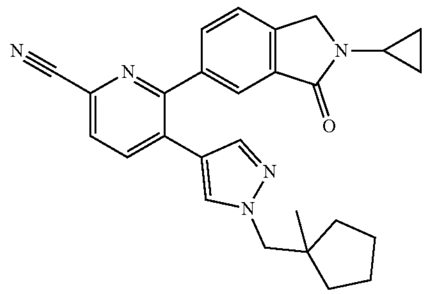 [SMILES: CC1(Cn2cc(-c3ccc(C#N)nc3-c3ccc4c(c3)C(=O)N(C3CC3)C4)cn2)CCCC1] | 6-(2-cyclopropyl-3-oxoisoindolin-5-yl)-5-(5-fluoro-1-((1-methylcyclopentyl)methyl)-1H-pyrazol-4-yl)picolinonitrile | 456 |
| 45 | 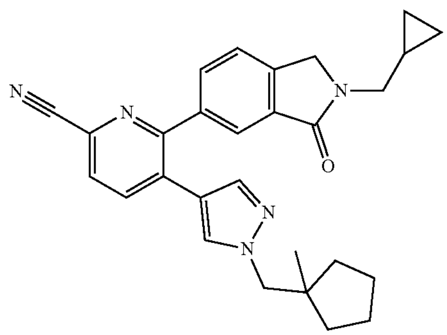 [SMILES: CC1(Cn2cc(-c3ccc(C#N)nc3-c3ccc4c(c3)C(=O)N(CC3CC3)C4)cn2)CCCC1] | 6-(2-(cyclopropylmethyl)-3-oxoisoindolin-5-yl)-5-(5-fluoro-1-((1-methylcyclopentyl)methyl)-1H-pyrazol-4-yl)picolinonitrile | 470 |
| 46 | 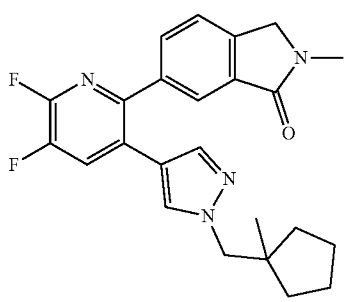 [SMILES: CN1Cc2ccc(-c3nc(F)c(F)cc3-c3cnn(CC4(C)CCCC4)c3)cc2C1=O] | 6-(5,6-difluoro-3-(1-((1-methylcyclopentyl)methyl)-1H-pyrazol-4-yl)pyridin-2-yl)-2-methylisoindolin-1-one | 423 |
| 47 | 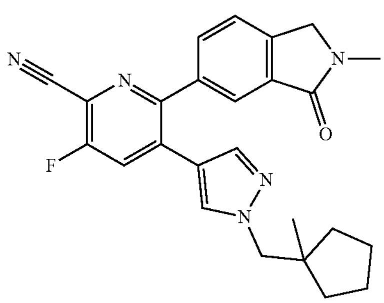 [SMILES: CN1Cc2ccc(-c3nc(C#N)c(F)cc3-c3cnn(CC4(C)CCCC4)c3)cc2C1=O] | 3-fluoro-6-(2-methyl-3-oxoisoindolin-5-yl)-5-(1-((1-methylcyclopentyl)methyl)-1H-pyrazol-4-yl)picolinonitrile | 430 |
| 48 | 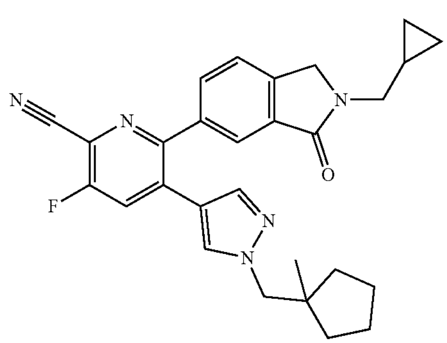 [SMILES: CC1(Cn2cc(-c3cc(F)c(C#N)nc3-c3ccc4c(c3)C(=O)N(CC3CC3)C4)cn2)CCCC1] | 6-(2-(cyclopropylmethyl)-3-oxoisoindolin-5-yl)-3-fluoro-5-(1-((1-methylcyclopentyl)methyl)-1H-pyrazol-4-yl)picolinonitrile | 470 |

TABLE 1-continued

| Example | Structure | Name | MS (M + 1) |
|---|---|---|---|
| 49 | 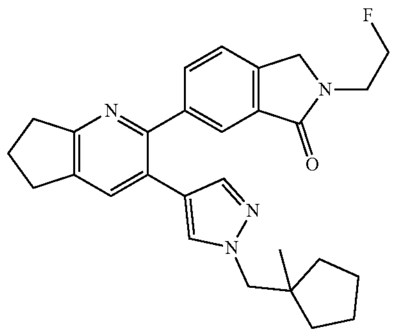 [SMILES: CC1(Cn2cc(-c3cc4c(nc3-c3ccc5c(c3)C(=O)N(CCF)C5)CCC4)cn2)CCCC1] | 2-(2-fluoroethyl)-6-(3-(1-((1-methylcyclopentyl)methyl)-1H-pyrazol-4-yl)-6,7-dihydro-5H-cyclopenta[b]pyridin-2-yl)isoindolin-1-one | 459 |
| 50 | 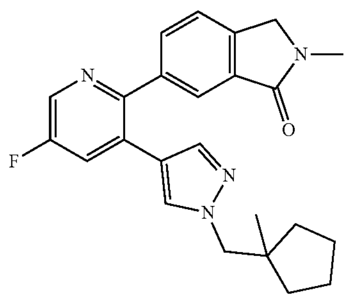 [SMILES: CN1Cc2ccc(-c3ncc(F)cc3-c3cnn(CC4(C)CCCC4)c3)cc2C1=O] | 6-(5-fluoro-3-(1-((1-methylcyclopentyl)methyl)-1H-pyrazol-4-yl)pyridin-2-yl)-2-methylisoindolin-1-one | 405 |
| 51 | 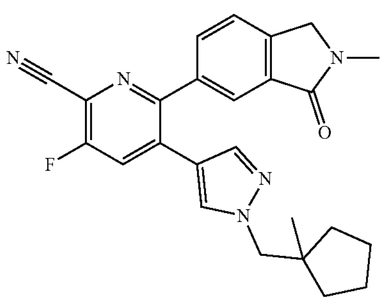 [SMILES: CN1Cc2ccc(-c3nc(C#N)c(F)cc3-c3cnn(CC4(C)CCCC4)c3)cc2C1=O] | 3-amino-6-(2-methyl-3-oxoisoindolin-5-yl)-5-(1-((1-methylcyclopentyl)methyl)-1H-pyrazol-4-yl)picolinonitrile | 427 |
| 52 | 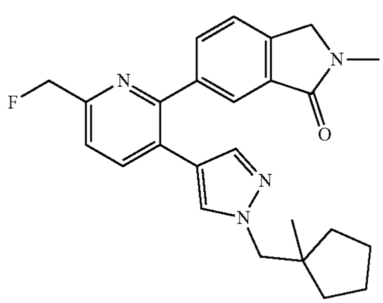 [SMILES: CN1Cc2ccc(-c3nc(CF)ccc3-c3cnn(CC4(C)CCCC4)c3)cc2C1=O] | 6-(6-(fluoromethyl)-3-(1-((1-methylcyclopentyl)methyl)-1H-pyrazol-4-yl)pyridin-2-yl)-2-methylisoindolin-1-one | 419 |
| 53 | 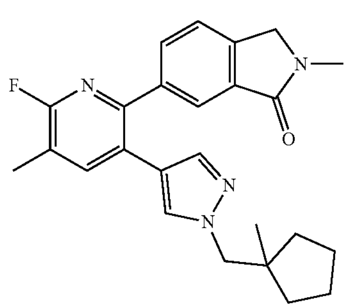 [SMILES: Cc1cc(-c2cnn(CC3(C)CCCC3)c2)c(-c2ccc3c(c2)C(=O)N(C)C3)nc1F] | 6-(6-fluoro-5-methyl-3-(1-((1-methylcyclopentyl)methyl)-1H-pyrazol-4-yl)pyridin-2-yl)-2-methylisoindolin-1-one | 419 |

TABLE 1-continued

| Example | Structure | Name | MS (M + 1) |
|---|---|---|---|
| 54 | 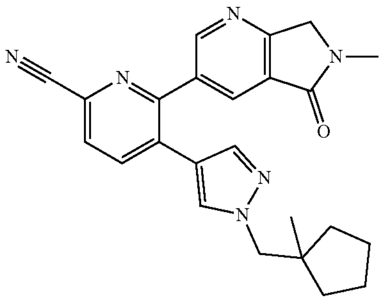 [SMILES: CN1Cc2ncc(-c3nc(C#N)ccc3-c3cnn(CC4(C)CCCC4)c3)cc2C1=O] | 5-(5-fluoro-1-((1-methylcyclopentyl)methyl)-1H-pyrazol-4-yl)-6-(6-methyl-5-oxo-6,7-dihydro-5H-pyrrolo[3,4-b]pyridin-3-yl)picolinonitrile | 431 |
| 55 | 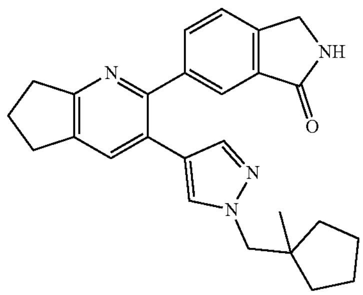 [SMILES: CC1(Cn2cc(-c3cc4c(nc3-c3ccc5c(c3)C(=O)NC5)CCC4)cn2)CCCC1] | 6-(3-(1-((1-methylcyclopentyl)methyl)-1H-pyrazol-4-yl)-6,7-dihydro-5H-cyclopenta[b]pyridin-2-yl)isoindolin-1-one | 413 |
| 56 | 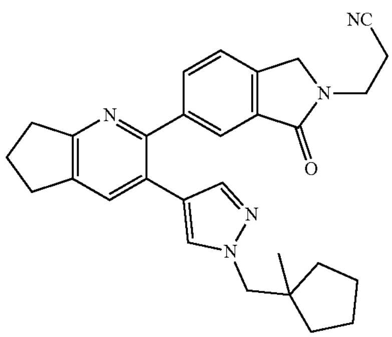 [SMILES: CC1(Cn2cc(-c3cc4c(nc3-c3ccc5c(c3)C(=O)N(CCC#N)C5)CCC4)cn2)CCCC1] | 3-(6-(3-(1-((1-methylcyclopentyl)methyl)-1H-pyrazol-4-yl)-6,7-dihydro-5H-cyclopenta[b]pyridin-2-yl)-1-oxoisoindolin-2-yl)propanenitrile | 466 |
| 57 | 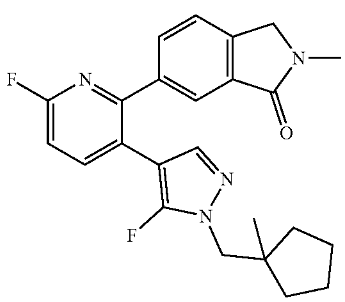 [SMILES: CN1Cc2ccc(-c3nc(F)ccc3-c3cnn(CC4(C)CCCC4)c3F)cc2C1=O] | 6-(6-fluoro-3-(5-fluoro-1-((1-methylcyclopentyl)methyl)-1H-pyrazol-4-yl)pyridin-2-yl)-2-methylisoindolin-1-one | 423 |
| 58 | 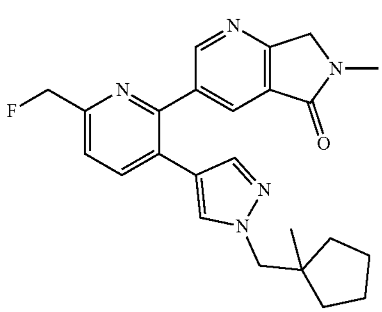 [SMILES: CN1Cc2ncc(-c3nc(CF)ccc3-c3cnn(CC4(C)CCCC4)c3)cc2C1=O] | 3-(6-(fluoromethyl)-3-(1-((1-methylcyclopentyl)methyl)-1H-pyrazol-4-yl)pyridin-2-yl)-6-methyl-6,7-dihydro-5H-pyrrolo[3,4-b]pyridin-5-one | 420 |

TABLE 1-continued

| Example | Structure | Name | MS (M + 1) |
|---|---|---|---|
| 59 | 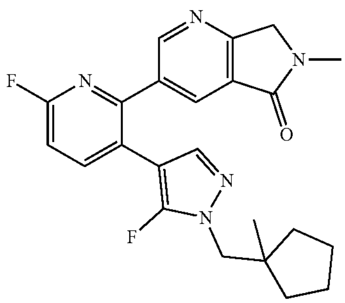 [SMILES: CN1Cc2ncc(-c3nc(F)ccc3-c3cnn(CC4(C)CCCC4)c3F)cc2C1=O] | 3-(6-fluoro-3-(5-fluoro-1-((1-methylcyclopentyl)methyl)-1H-pyrazol-4-yl)pyridin-2-yl)-6-methyl-6,7-dihydro-5H-pyrrolo[3,4-b]pyridin-5-one | 424 |
| 60 | 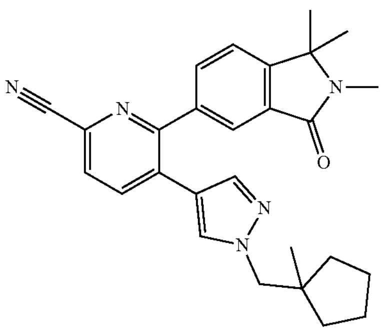 [SMILES: CN1C(=O)c2cc(-c3nc(C#N)ccc3-c3cnn(CC4(C)CCCC4)c3)ccc2C1(C)C] | 5-((1-((1-methylcyclopentyl)methyl)-1H-pyrazol-4-yl)-6-(1,1,2-trimethyl-3-oxoisoindolin-5-yl)picolinonitrile | 440 |
| 61 | 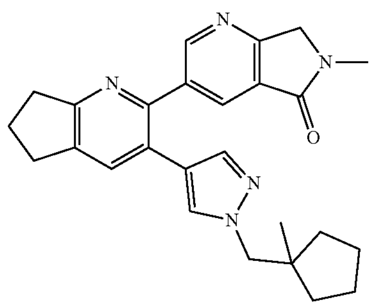 [SMILES: CN1Cc2ncc(-c3nc4c(cc3-c3cnn(CC5(C)CCCC5)c3)CCC4)cc2C1=O] | 6-methyl-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 428 |
| 62 | 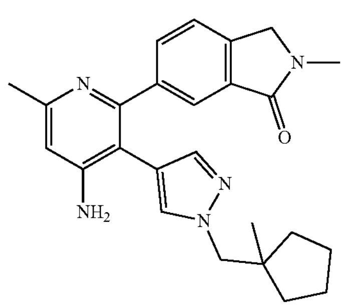 | 6-(4-amino-6-methyl-3-(1-((1-methylcyclopentyl)methyl)-1H-pyrazol-4-yl)pyridin-2-yl)-2-methylisoindolin-1-one | 417 |
| 63 | 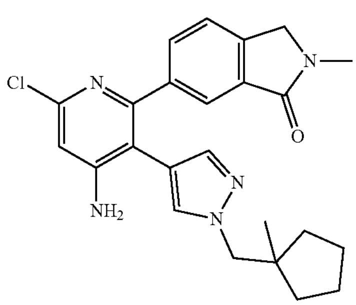 [SMILES: CN1Cc2ccc(-c3nc(Cl)cc(N)c3-c3cnn(CC4(C)CCCC4)c3)cc2C1=O] | 6-(4-amino-6-chloro-3-(1-((1-methylcyclopentyl)methyl)-1H-pyrazol-4-yl)pyridin-2-yl)-2-methylisoindolin-1-one | 436 |

TABLE 1-continued

| Example | Structure | Name | MS (M + 1) |
|---|---|---|---|
| 64 | 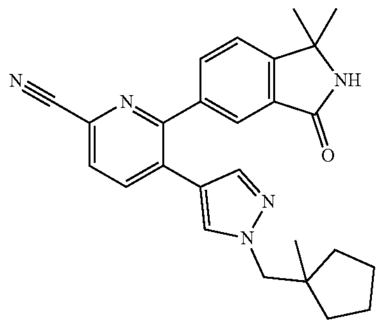 [SMILES: CC1(Cn2cc(-c3ccc(C#N)nc3-c3ccc4c(c3)C(=O)NC4(C)C)cn2)CCCC1] | 6-(1,1-dimethyl-3-oxoisoindolin-5-yl)-5-(1-((1-methylcyclopentyl)methyl)-1H-pyrazol-4-yl)picolinonitrile | 426 |
| 65 | 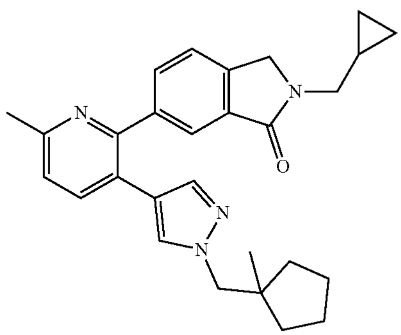 [SMILES: Cc1ccc(-c2cnn(CC3(C)CCCC3)c2)c(-c2ccc3c(c2)C(=O)N(CC2CC2)C3)n1] | 2-(cyclopropylmethyl)-6-(6-methyl-3-(1-((1-methylcyclopentyl)methyl)-1H-pyrazol-4-yl)pyridin-2-yl)isoindolin-1-one | 441 |
| 66 | 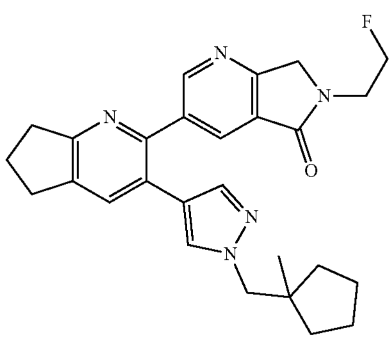 [SMILES: CC1(Cn2cc(-c3cc4c(nc3-c3cnc5c(c3)C(=O)N(CCF)C5)CCC4)cn2)CCCC1] | 6-(2-fluoroethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 460 |
| 67 | 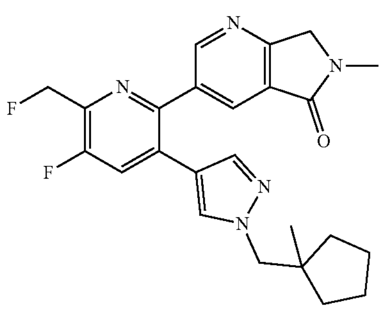 [SMILES: CN1Cc2ncc(-c3nc(CF)c(F)cc3-c3cnn(CC4(C)CCCC4)c3)cc2C1=O] | 3-(3-(5-fluoro-1-((1-methylcyclopentyl)methyl)-1H-pyrazol-4-yl)-6-(fluoromethyl)pyridin-2-yl)-6-methyl-6,7-dihydro-5H-pyrrolo[3,4-b]pyridin-5-one | 438 |
| 68 | 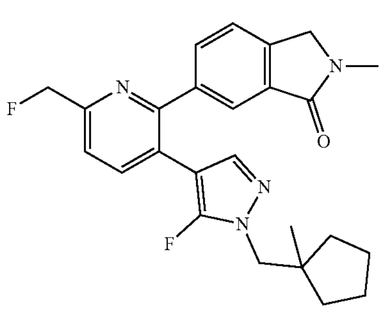 [SMILES: CN1Cc2ccc(-c3nc(CF)ccc3-c3cnn(CC4(C)CCCC4)c3F)cc2C1=O] | 6-(3-(5-fluoro-1-((1-methylcyclopentyl)methyl)-1H-pyrazol-4-yl)-6-(fluoromethyl)pyridin-2-yl)-2-methylisoindolin-1-one | 437 |

TABLE 1-continued

| Example | Structure | Name | MS (M + 1) |
|---|---|---|---|
| 69 | 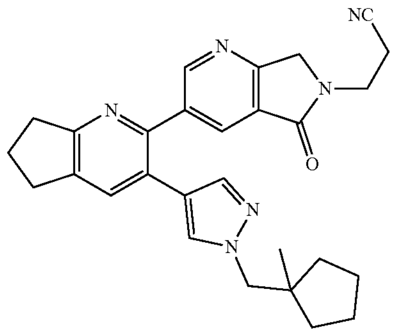 [SMILES: CC1(Cn2cc(-c3cc4c(nc3-c3cnc5c(c3)C(=O)N(CCC#N)C5)CCC4)cn2)CCCC1] | 3-(3-(3-(1-((1-methylcyclopentyl)methyl)-1H-pyrazol-4-yl)-6,7-dihydro-5H-cyclopenta[b]pyridin-2-yl)-5-oxo-5,7-dihydro-6H-pyrrolo[3,4-b]pyridin-6-yl)propanenitrile | 467 |
| 70 | 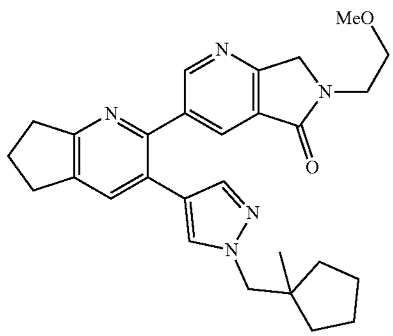 [SMILES: COCCN1Cc2ncc(-c3nc4c(cc3-c3cnn(CC5(C)CCCC5)c3)CCC4)cc2C1=O] | 6-(2-methoxyethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 472 |
| 71 | 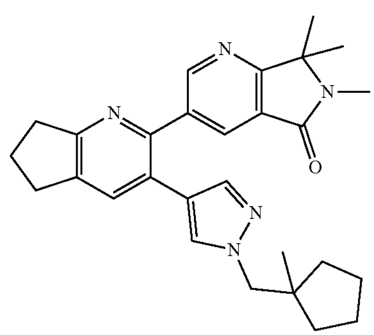 [SMILES: CN1C(=O)c2cc(-c3nc4c(cc3-c3cnn(CC5(C)CCCC5)c3)CCC4)cnc2C1(C)C] | 6,7,7-trimethyl-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 456 |
| 72 | 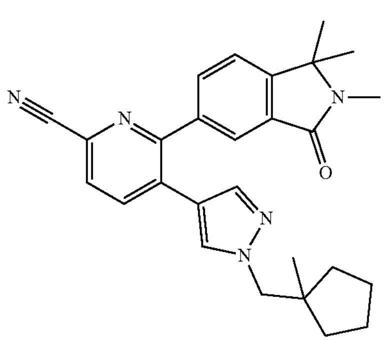 [SMILES: CN1C(=O)c2cc(-c3nc(C#N)ccc3-c3cnn(CC4(C)CCCC4)c3)ccc2C1(C)C] | 5-((1-((1-methylcyclopentyl)methyl)-1H-pyrazol-4-yl)-6-(1,1,2-trimethyl-3-oxoisoindolin-5-yl)picolinonitrile | 441 |

TABLE 1-continued

| Example | Structure | Name | MS (M + 1) |
|---|---|---|---|
| 73 | 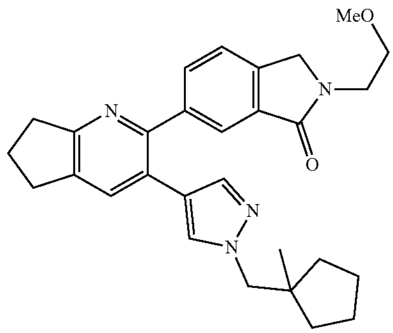 [SMILES: COCCN1Cc2ccc(-c3nc4c(cc3-c3cnn(CC5(C)CCCC5)c3)CCC4)cc2C1=O] | 2-(2-methoxyethyl)-6-(3-(1-((1-methylcyclopentyl)methyl)-1H-pyrazol-4-yl)-6,7-dihydro-5H-cyclopenta[b]pyridin-2-yl)isoindolin-1-one | 471 |
| 74 | 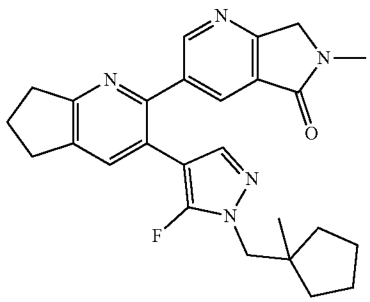 [SMILES: CN1Cc2ncc(-c3nc4c(cc3-c3cnn(CC5(C)CCCC5)c3F)CCC4)cc2C1=O] | 3-(3-(5-fluoro-1-((1-methylcyclopentyl)methyl)-1H-pyrazol-4-yl)-6,7-dihydro-5H-cyclopenta[b]pyridin-2-yl)-6-methyl-6,7-dihydro-5H-pyrrolo[3,4-b]pyridin-5-one | 446 |
| 75 | 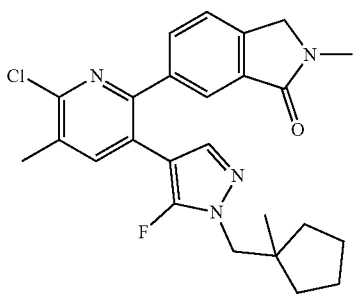 [SMILES: Cc1cc(-c2cnn(CC3(C)CCCC3)c2F)c(-c2ccc3c(c2)C(=O)N(C)C3)nc1Cl] | 6-(6-chloro-3-(5-fluoro-1-((1-methylcyclopentyl)methyl)-1H-pyrazol-4-yl)-5-methylpyridin-2-yl)-2-methylisoindolin-1-one | 453 |
| 76 | 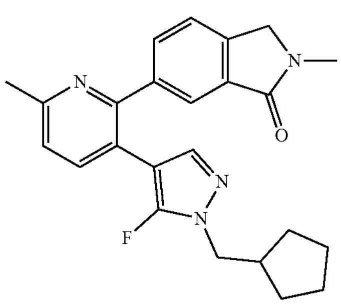 | 6-(3-(1-(cyclopentylmethyl)-5-fluoro-1H-pyrazol-4-yl)-6-methylpyridin-2-yl)-2-methylisoindolin-1-one | 405 |
| 77 | 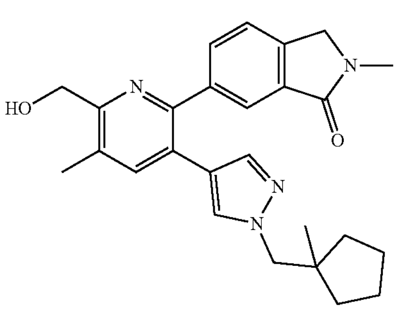 [SMILES: Cc1cc(-c2cnn(CC3(C)CCCC3)c2)c(-c2ccc3c(c2)C(=O)N(C)C3)nc1CO] | 6-(6-(hydroxymethyl)-5-methyl-3-(1-((1-methylcyclopentyl)methyl)-1H-pyrazol-4-yl)pyridin-2-yl)-2-methylisoindolin-1-one | 431 |

TABLE 1-continued

| Example | Structure | Name | MS (M + 1) |
|---|---|---|---|
| 78 | 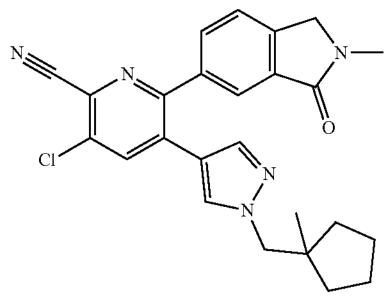 [SMILES: CN1Cc2ccc(-c3nc(C#N)c(Cl)cc3-c3cnn(CC4(C)CCCC4)c3)cc2C1=O] | 3-chloro-6-(2-methyl-3-oxoisoindolin-5-yl)-5-(1-((1-methylcyclopentyl)methyl)-1H-pyrazol-4-yl)picolinonitrile | 447 |
| 79 | 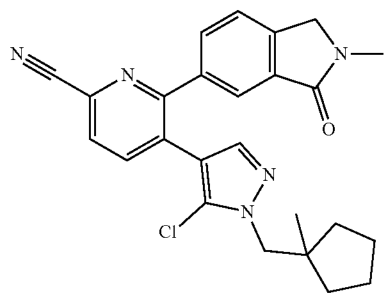 [SMILES: CN1Cc2ccc(-c3nc(C#N)ccc3-c3cnn(CC4(C)CCCC4)c3Cl)cc2C1=O] | 5-(5-chloro-1-((1-methylcyclopentyl)methyl)-1H-pyrazol-4-yl)-6-(2-methyl-3-oxoisoindolin-5-yl)picolinonitrile | 446 |
| 80 | 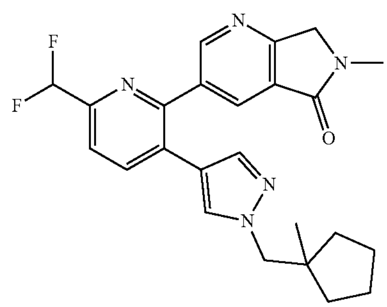 [SMILES: CN1Cc2ncc(-c3nc(C(F)F)ccc3-c3cnn(CC4(C)CCCC4)c3)cc2C1=O] | 3-(6-(difluoromethyl)-3-(1-((1-methylcyclopentyl)methyl)-1H-pyrazol-4-yl)pyridin-2-yl)-6-methyl-6,7-dihydro-5H-pyrrolo[3,4-b]pyridin-5-one | 438 |
| 81 | 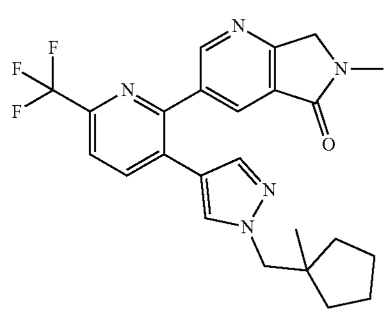 [SMILES: CN1Cc2ncc(-c3nc(C(F)(F)F)ccc3-c3cnn(CC4(C)CCCC4)c3)cc2C1=O] | 6-methyl-3-(3-(1-((1-methylcyclopentyl)methyl)-1H-pyrazol-4-yl)-6-(trifluoromethyl)pyridin-2-yl)-6,7-dihydro-5H-pyrrolo[3,4-b]pyridin-5-one | 456 |
| 82 | 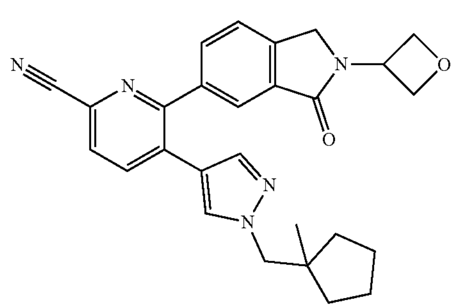 [SMILES: CC1(Cn2cc(-c3ccc(C#N)nc3-c3ccc4c(c3)C(=O)N(C3COC3)C4)cn2)CCCC1] | 5-(1-((1-methylcyclopentyl)methyl)-1H-pyrazol-4-yl)-6-(2-(oxetan-3-yl)-3-oxoisoindolin-5-yl)picolinonitrile | 454 |

TABLE 1-continued

| Example | Structure | Name | MS (M + 1) |
|---|---|---|---|
| 83* | 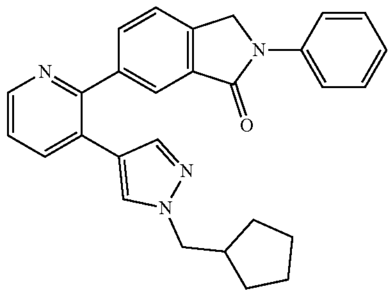 [SMILES: O=C1c2cc(-c3ncccc3-c3cnn(CC4CCCC4)c3)ccc2CN1c1ccccc1] | 6-(3-(1-(cyclopentylmethyl)-1H-pyrazol-4-yl)pyridin-2-yl)-2-phenylisoindolin-1-one | 435 |

*Boronic ester obtained by following literature procedure: Lawson, J. D., et al. PCT Int. Appl. (2013), WO 2013148603 A1 Oct. 03, 2013.

Example 84

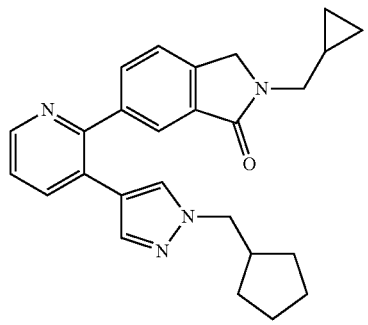 [SMILES: O=C1c2cc(-c3ncccc3-c3cnn(CC4CCCC4)c3)ccc2CN1CC1CC1]

6-(3-(1-(Cyclopentylmethyl)-1H-pyrazol-4-yl)pyridin-2-yl)-2-(cyclopropylmethyl)isoindolin-1-one (Scheme 2)

Step 1: Methyl 5-(3-(1-(cyclopentylmethyl)-1H-pyrazol-4-pyridine-2-yl)-2-methylbenzoate Combine 2-chloro-3-(1-(cyclopentylmethyl)-1H-pyrazol-4-yl)pyridine (intermediate F2, 400 mg, 1.53 mmol), (3-(methoxycarbonyl)-4-methylphenyl)boronic acid (intermediate C4, 593 mg, 3.06 mmol), 1,1'-bis(di-tert-butylphosphino)ferrocene palladium dichloride (100 mg, 0.153 mmol), and $K_3PO_4$ (1 M in water, 4.58 mL, 4.58 mmol). The system was placed under a $N_2$ atmosphere and THF (15.3 mL) was added before heating the mixture to 110° C. for 10 min under microwave irradiation. The reaction was diluted with water and EtOAc and the organic was dried over anhydrous sodium sulfate, filtered, and concentrated under reduced pressure. The crude residue was purified by silica gel column (0-70% EtOAc/hexanes) to yield the title compound. MS: 376 (M+1).

Step 2: Methyl 2-(bromomethyl)-5-(3-(1-(cyclopentylmethyl)-1H-pyrazol-4-yl)pyridin-2-yl)benzoate NBS (270 mg, 1.52 mmol), benzoyl peroxide (153 mg, 0.63 mmol), and methyl 5-(3-(1-(cyclopentylmethyl)-1H-pyrazol-4-yl)pyridin-2-yl)-2-methylbenzoate (475 mg, 1.27 mmol) and carbon tetrachloride (12 mL) were combined in a vial. The system was sealed and heated to 80° C. for 1 h. The reaction was then cooled, filtered and concentrated and the title compound was used without further purification. MS: 454, 456 (M+1).

Step 3: 6-(3-(1-(Cyclopentylmethyl)-1H-pyrazol-4-yl)pyridin-2-yl)-2-(cyclopropylmethyl)isoindolin-1-one Cyclopropylmethanamine (8.52 mg, 0.12 mmol) and methyl 2-(bromomethyl)-5-(3-(1-(cyclopentylmethyl)-1H-pyrazol-4-yl)pyridin-2-yl)benzoate (18.2 mg, 0.04 mmol) were combined in flask with DMF (400 µL). The reaction was stirred at RT for 15 minutes and was concentrated to remove excess solvent. The crude mixture was purified by mass triggered reverse phase HPLC (ACN/water with 0.1% TFA modifier) to afford the title compound. MS: 413 (M+1). $^1$H NMR (499 MHz, DMSO-$d_6$): δ 8.27 (d, J=4.8 Hz, 1H), 7.66 (d, J=7.8 Hz, 1H), 7.30-7.31 (m, 3H), 7.19 (dd, J=7.93, 4.80 Hz, 1H), 7.08 (s, 1H), 6.94 (s, 1H), 4.30 (s, 2H), 3.58 (d, J=7.5 Hz, 2H), 2.17-2.21 (m, 4H); 1.82-1.92 (m, 1H), 1.07-1.22 (m, 7H), 0.69-0.78 (m, 2H), 0.21 (d, J=7.7 Hz, 2H).

The following examples in Table 2 were prepared according to Scheme 2 using the procedure outlined in the synthesis of Example 84 using commercially available amines in step 3.

TABLE 2

| Example | Structure | Name | MS (M + 1) |
|---|---|---|---|
| 85 | 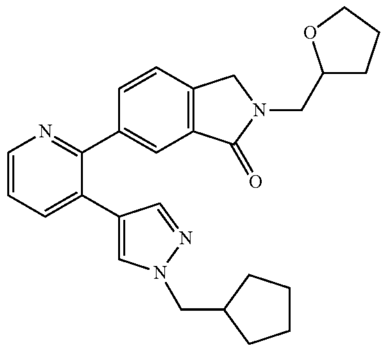 [SMILES: O=C1c2cc(-c3ncccc3-c3cnn(CC4CCCC4)c3)ccc2CN1CC1CCCO1] | 6-(3-(1-(cyclopentylmethyl)-1H-pyrazol-4-yl)pyridin-2-yl)-2-((tetrahydrofuran-2-yl)methyl)isoindolin-1-one | 443 |
| 86 | 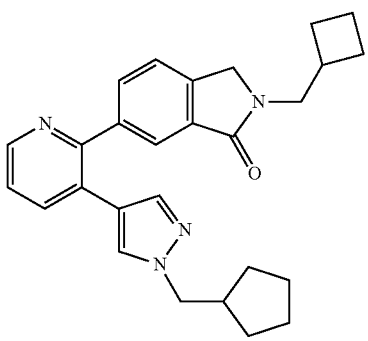 [SMILES: O=C1c2cc(-c3ncccc3-c3cnn(CC4CCCC4)c3)ccc2CN1CC1CCC1] | 2-(cyclobutylmethyl)-6-(3-(1-(cyclopentylmethyl)-1H-pyrazol-4-yl)pyridin-2-yl)isoindolin-1-one | 427 |
| 87 | 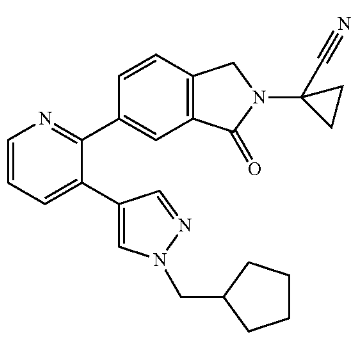 [SMILES: N#CC1(N2Cc3ccc(-c4ncccc4-c4cnn(CC5CCCC5)c4)cc3C2=O)CC1] | 1-(6-(3-(1-(cyclopentylmethyl)-1H-pyrazol-4-yl)pyridin-2-yl)-1-oxoisoindolin-2-yl)cyclopropane-1-carbonitrile | 424 |
| 88 | 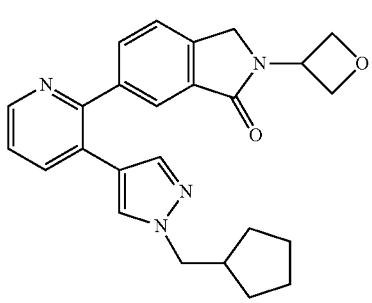 [SMILES: O=C1c2cc(-c3ncccc3-c3cnn(CC4CCCC4)c3)ccc2CN1C1COC1] | 6-(3-(1-(cyclopentylmethyl)-1H-pyrazol-4-yl)pyridin-2-yl)-2-(oxetan-3-yl)isoindolin-1-one | 415 |

TABLE 2-continued

| Example | Structure | Name | MS (M + 1) |
|---|---|---|---|
| 89 | 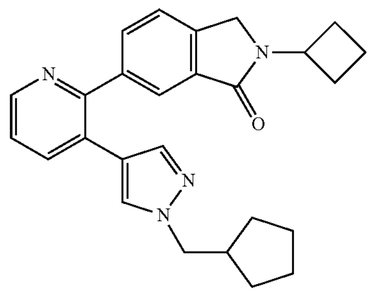 [SMILES: O=C1c2cc(-c3ncccc3-c3cnn(CC4CCCC4)c3)ccc2CN1C1CCC1] | 2-cyclobutyl-6-(3-(1-(cyclopentylmethyl)-1H-pyrazol-4-yl)pyridin-2-yl)isoindolin-1-one | 413 |
| 90 | 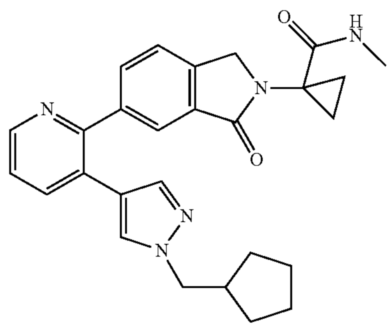 [SMILES: CNC(=O)C1(N2Cc3ccc(-c4ncccc4-c4cnn(CC5CCCC5)c4)cc3C2=O)CC1] | 1-(6-(3-(1-(cyclopentylmethyl)-1H-pyrazol-4-yl)pyridin-2-yl)-1-oxoisoindolin-2-yl)-N-methylcyclopropane-1-carboxamide | 456 |
| 91 | 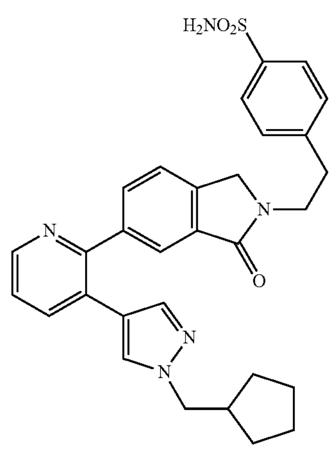 [SMILES: NS(=O)(=O)c1ccc(CCN2Cc3ccc(-c4ncccc4-c4cnn(CC5CCCC5)c4)cc3C2=O)cc1] | 4-(2-(6-(3-(1-(cyclopentylmethyl)-1H-pyrazol-4-yl)pyridin-2-yl)-1-oxoisoindolin-2-yl)ethyl)benzenesulfonamide | 542 |
| 92 | 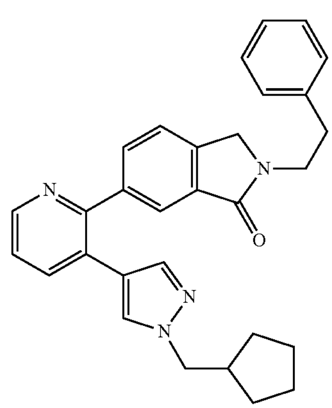 [SMILES: O=C1c2cc(-c3ncccc3-c3cnn(CC4CCCC4)c3)ccc2CN1CCc1ccccc1] | 6-(3-(1-(cyclopentylmethyl)-1H-pyrazol-4-yl)pyridin-2-yl)-2-phenethylisoindolin-1-one | 463 |

TABLE 2-continued

| Example | Structure | Name | MS (M + 1) |
|---|---|---|---|
| 93 | 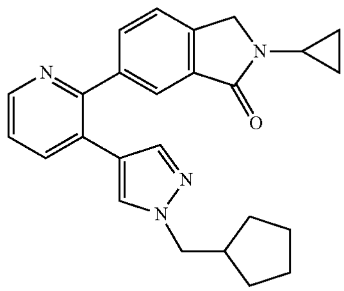 [SMILES: O=C1c2cc(-c3ncccc3-c3cnn(CC4CCCC4)c3)ccc2CN1C1CC1] | 6-(3-(1-(cyclopentyl-methyl)-1H-pyrazol-4-yl)pyridin-2-yl)-2-cyclopropylisoindolin-1-one | 399 |
| 94 | 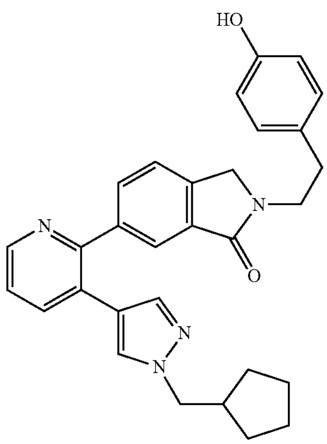 [SMILES: O=C1c2cc(-c3ncccc3-c3cnn(CC4CCCC4)c3)ccc2CN1CCc1ccc(O)cc1] | 6-(3-(1-(cyclopentylmethyl)-1H-pyrazol-4-yl)pyridin-2-yl)-2-(4-hydroxyphenethyl)isoindolin-1-one | 465 |

Example 95

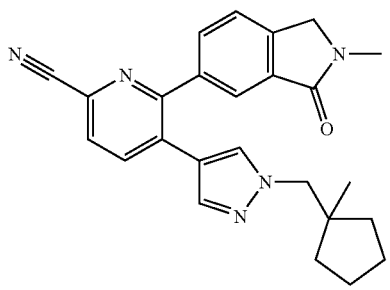 [SMILES: CN1Cc2ccc(-c3nc(C#N)ccc3-c3cnn(CC4(C)CCCC4)c3)cc2C1=O]

6-(6-Methyl-5-oxo-6,7-dihydro-5H-pyrrolo[3,4-b]pyridin-3-yl)-5-(1-((1-methylcyclopentyl)methyl)-1H-pyrazol-4-yl)picolinonitrile (Scheme 3)

3-Bromo-6-methyl-6,7-dihydro-5H-pyrrolo[3,4-b]pyridin-5-one (intermediate B1, 54.5 mg, 0.24 mmol), bis(pinacolato)diboron (66.0 mg, 0.26 mmol) and potassium acetate (58.9 mg, 0.60 mmol) were added to a 4 mL reaction vial. The vial was evacuated and charged with nitrogen, after which dioxane (1.6 mL) was added. The system was evacuated and flushed with nitrogen (3×), then chloro(2-dicyclohexylphosphino-2',4',6'-triisopropyl-1,1'-biphenyl)[2-(2'-amino-1,1'-biphenyl)]palladium(II) (9.44 mg, 0.012 mmol) was added. An additional evacuation and nitrogen flush sequence was undertaken, and then the reaction was stirred at 100° C. After 90 minutes the reaction mixture was cooled to room temperature, and then 6-chloro-5-(1-((1-methylcyclopentyl)-methyl)-1H-pyrazol-4-yl)picolinonitrile (intermediate G1, 60.2 mg, 0.20 mmol), followed by 1,1'-bis(di-tert-butylphosphino)ferrocene palladium dichloride (9.78 mg, 0.015 mmol) and potassium carbonate (3 M in water, 200 µL, 0.600 mmol) was added. The system was heated to 80° C. for 8 h and was worked-up by diluting with ethyl acetate and washing the organic with water (2×). The organic was dried over anhydrous sodium sulfate, filtered and evaporated. The crude residue was purified by silica gel column (0-40% 3:1 EtOAc:EtOH/hexanes) to yield the title compound. MS: 413 (M+1). $^1$H NMR (500 MHz, CDCl$_3$): δ 8.79 (d, J=1.7 Hz, 1H), 8.17 (d, J=1.9 Hz, 1H), 7.91 (d, J=8.0 Hz, 1H), 7.73 (d, J=8.0 Hz, 1H), 7.32 (s, 1H), 7.02 (s, 1H), 4.49 (s, 2H), 3.89 (s, 2H), 3.25 (s, 3H), 1.75-1.54 (m, 4H), 1.43 (m, 2H), 1.27 (m, 2H), 0.85 (s, 3H).

The following examples in Table 3 were prepared according to Scheme 3 using the procedure outlined in the synthesis of Example 95 using known or prepared intermediates. Alternative conditions are using chloro[(di(1-adamantyl)-N-butylphosphine)-2-(2-amino-biphenyl)] palladium(II) as the sole palladium catalyst to effect the one-pot borylation/Suzuki reaction at 50° C., using hypoboric acid and Hünig's base in the borylation step and then aqueous K$_3$PO$_4$ in the subsequent Suzuki reaction.

TABLE 3

| Example | Structure | Name | MS (M + 1) |
|---|---|---|---|
| 96 | 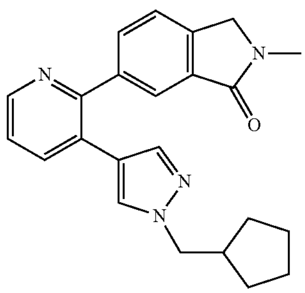 [SMILES: CN1Cc2ccc(-c3ncccc3-c3cnn(CC4CCCC4)c3)cc2C1=O] | 6-(3-(1-(cyclopentylmethyl)-1H-pyrazol-4-yl)pyridin-2-yl)-2-methylisoindolin-1-one | 373 |
| 97 | 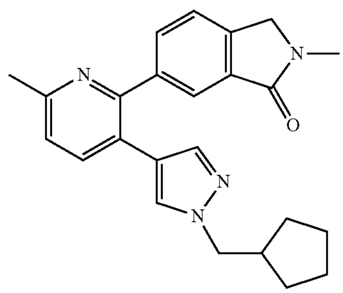 | 6-(3-(1-(cyclopentylmethyl)-1H-pyrazol-4-yl)-6-methylpyridin-2-yl)-2-methylisoindolin-1-one | 387 |
| 98 | 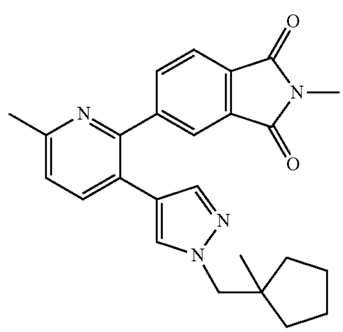 | 2-methyl-5-(6-methyl-3-(1-((1-methylcyclopentyl)methyl)-1H-pyrazol-4-yl)pyridin-2-yl)isoindoline-1,3-dione | 415 |
| 99 | 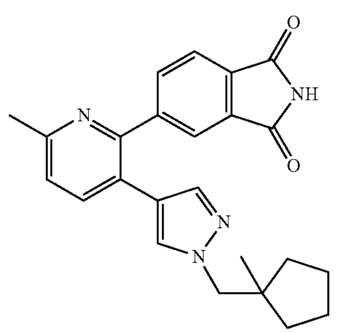 [SMILES: Cc1ccc(-c2cnn(CC3(C)CCCC3)c2)c(-c2ccc3c(c2)C(=O)NC3=O)n1] | 5-(6-methyl-3-(1-((1-methylcyclopentyl)methyl)-1H-pyrazol-4-yl)pyridin-2-yl)isoindoline-1,3-dione | 401 |
| 100 | 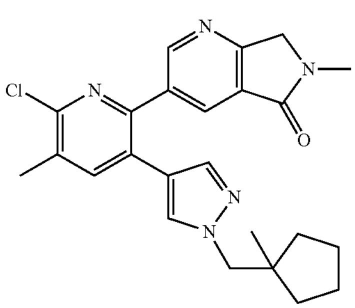 [SMILES: Cc1cc(-c2cnn(CC3(C)CCCC3)c2)c(-c2cnc3c(c2)C(=O)N(C)C3)nc1Cl] | 3-(6-chloro-5-methyl-3-(1-((1-methylcyclopentyl)methyl)-1H-pyrazol-4-yl)pyridin-2-yl)-6-methyl-6,7-dihydro-5H-pyrrolo[3,4-b]pyridin-5-one | 436 |

TABLE 3-continued

| Example | Structure | Name | MS (M + 1) |
|---|---|---|---|
| 101 | 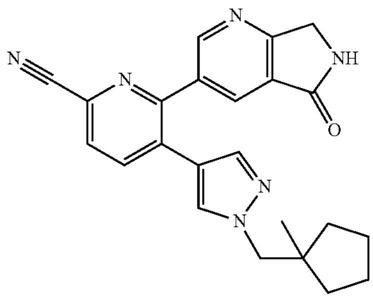 [SMILES: CC1(Cn2cc(-c3ccc(C#N)nc3-c3cnc4c(c3)C(=O)NC4)cn2)CCCC1] | 5-(1-((1-methylcyclopentyl)methyl)-1H-pyrazol-4-yl)-6-(5-oxo-6,7-dihydro-5H-pyrrolo[3,4-b]pyridin-3-yl)picolinonitrile | 399 |
| 102 | 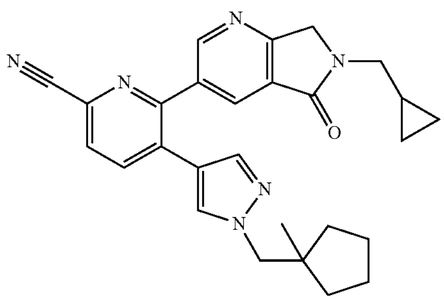 [SMILES: CC1(Cn2cc(-c3ccc(C#N)nc3-c3cnc4c(c3)C(=O)N(CC3CC3)C4)cn2)CCCC1] | 6-(6-(cyclopropylmethyl)-5-oxo-6,7-dihydro-5H-pyrrolo[3,4-b]pyridin-3-yl)-5-(1-((1-methylcyclopentyl)methyl)-1H-pyrazol-4-yl)picolinonitrile | 453 |
| 103 | 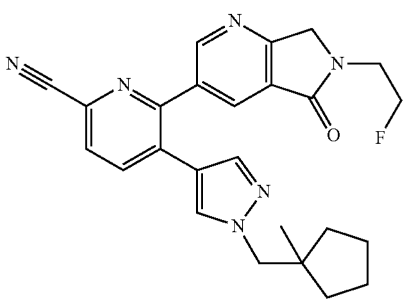 [SMILES: CC1(Cn2cc(-c3ccc(C#N)nc3-c3cnc4c(c3)C(=O)N(CCF)C4)cn2)CCCC1] | 6-(6-(2-fluoroethyl)-5-oxo-6,7-dihydro-5H-pyrrolo[3,4-b]pyridin-3-yl)-5-(1-((1-methylcyclopentyl)methyl)-1H-pyrazol-4-yl)picolinonitrile | 445 |
| 104 | 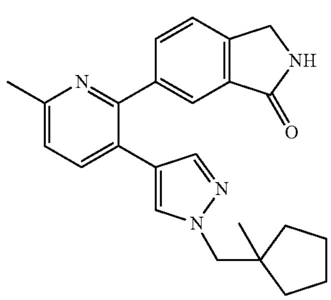 [SMILES: Cc1ccc(-c2cnn(CC3(C)CCCC3)c2)c(-c2ccc3c(c2)C(=O)NC3)n1] | 6-(6-methyl-3-(1-((1-methylcyclopentyl)methyl)-1H-pyrazol-4-yl)pyridin-2-yl)isoindolin-1-one | 387 |
| 105 | 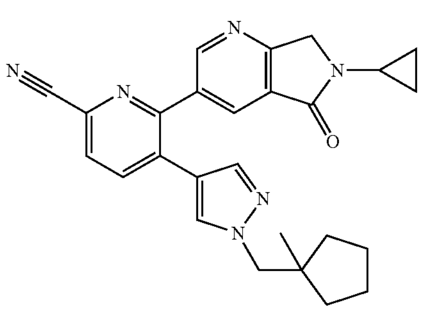 [SMILES: CC1(Cn2cc(-c3ccc(C#N)nc3-c3cnc4c(c3)C(=O)N(C3CC3)C4)cn2)CCCC1] | 6-(6-cyclopropyl-5-oxo-6,7-dihydro-5H-pyrrolo[3,4-b]pyridin-3-yl)-5-(1-((1-methylcyclopentyl)methyl)-1H-pyrazol-4-yl)picolinonitrile | 439 |

TABLE 3-continued

| Example | Structure | Name | MS (M + 1) |
|---|---|---|---|
| 106 | 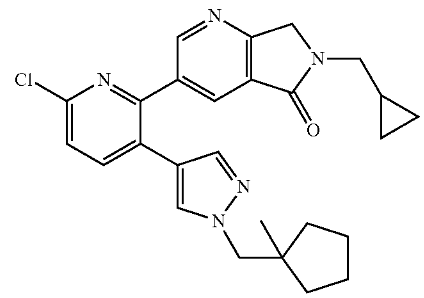 [SMILES: CC1(Cn2cc(-c3ccc(Cl)nc3-c3cnc4c(c3)C(=O)N(CC3CC3)C4)cn2)CCCC1] | 3-(6-chloro-3-(1-((1-methylcyclopentyl)methyl)-1H-pyrazol-4-yl)pyridin-2-yl)-6-(cyclopropylmethyl)-6,7-dihydro-5H-pyrrolo[3,4-b]pyridin-5-one | 462 |

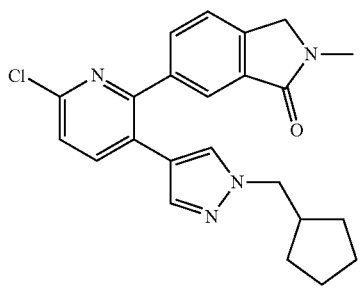 [SMILES: CN1Cc2ccc(-c3nc(Cl)ccc3-c3cnn(CC4CCCC4)c3)cc2C1=O]

6-(6-Chloro-3-(1-(cyclopentylmethyl)-1H-pyrazol-4-yl)pyridin-2-yl)-2-methylisoindolin-1-one (Scheme 4)

Step:1 3-(1-(Cyclopentylmethyl)-1H-pyrazol-4-yl)-2-(2-methyl-3-oxoisoindolin-5-yl)pyridine 1-oxide To a solution of 6-(3-(1-(cyclopentylmethyl)-1H-pyrazol-4-yl)pyridin-2-yl)-2-methylisoindolin-1-one (Example 96, 100 mg, 0.268 mmol) in DCM (1.5 mL) at 25° C. was added m-CPBA (93 mg, 0.537 mmol). After 3 h at RT, calcium hydroxide (80 mg, 1.07 mmol) and MeOH (1.5 mL) were added and the resultant white solid was filtered off (wash with DCM/MeOH). The filtrate was concentrated and title compound was obtained and used without further purification. MS: 389 (M+1)

Step 2: 6-(6-Chloro-3-(1-(cyclopentylmethyl)-1H-pyrazol-4-yl)pyridin-2-yl)-2-methylisoindolin-1-one 3-(1-(Cyclopentylmethyl)-1H-pyrazol-4-yl)-2-(2-methyl-3-oxoisoindolin-5-yl)pyridine-1-oxide (105 mg, 0.270 mmol) was dissolved in DCM (2.00 mL) at 25° C. Ethyl phosphorodichloridate (0.096 mL, 0.811 mmol) and diisopropylamine (0.116 mL, 0.811 mmol) was added dropwise to the reaction mixture. The resulting solution was stirred at 25° C. for 3 h and the crude reaction was directly loaded onto a silica gel column (0-60% acetone/hexanes) to yield the title compound. MS: 407 (M+1). $^1$H NMR (400 MHz, CDCl$_3$): δ 7.91 (s, 1H), 7.71 (s, 1H), 7.59 (d, J=7.32 Hz, 1H), 7.42 (d, J=7.33 Hz, 1H), 7.26-7.34 (m, 2H), 6.94 (s, 1H), 6.94 (s, 1H), 4.40 (s, 2H), 3.91 (s, 2H), 3.21 (s, 3H), 2.17-2.30 (m, 2H), 1.54-1.58 (m, 5H), 1.10-1.26 (m, 2H).

The following examples in Table 4 were prepared according to Scheme 4 using the procedure outlined in the synthesis of Example 107 using prepared intermediates.

TABLE 4

| Example | Structure | Name | MS (M + 1) |
|---|---|---|---|
| 108 | 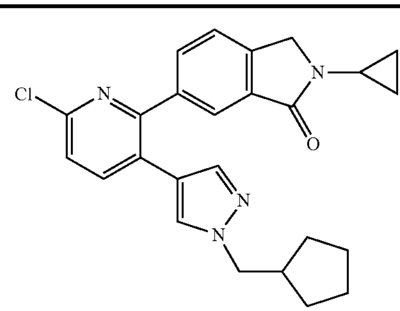 | 6-(6-chloro-3-(1-(cyclopentylmethyl)-1H-pyrazol-4-yl)pyridin-2-yl)-2-cyclopropylisoindolin-1-one | 433 |

Example 109

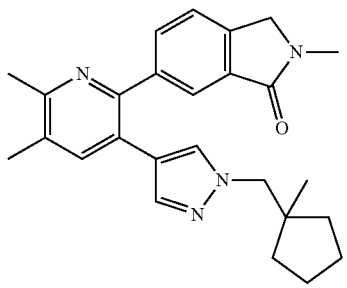 [SMILES: Cc1cc(-c2cnn(CC3(C)CCCC3)c2)c(-c2ccc3c(c2)C(=O)N(C)C3)nc1C]

6-(5,6-Dimethyl-3-(1-((1-methylcyclopentyl)methyl)-1H-pyrazol-4-yl)pyridin-2-yl)-2-methylisoindolin-1-one (Scheme 5)

2,4,6-Trimethyl-1,3,5,2,4,6-trioxatriborinane (6.93 mg, 0.055 mmol), 6-(6-chloro-5-methyl-3-(1-((1-methylcyclopentyl)methyl)-1H-pyrazol-4-yl)pyridin-2-yl)-2-methylisoindolin-1-one (Example 38, 20 mg, 0.046 mmol) and 1,1'-bis(di-tert-butylphosphino)ferrocene palladium dichloride (3.00 mg, 4.60 µmol) were placed in a 4 mL reaction vial and evacuated and charged with nitrogen. 1,4-Dioxane (1 mL) and potassium (3 M in water, 0.138 mL, 0.138 mmol) were added to the sealed vial and the system was heated to 100° C. After 2 h, the crude reaction mixture was cooled and purified by mass triggered reverse phase HPLC (ACN/water with 0.1% NH$_3$OH modifier) to afford the title compound. MS: 415 (M+1). $^1$H NMR (500 MHz, CDCl$_3$): δ 7.9 (s, 1H), 7.6 (d, J=8.6 Hz, 1H), 7.57 (s, 1H), 7.4 (d, J=7.8 Hz, 1H), 7.3 (s, 1H), 6.86 (s, 1H), 4.4 (s, 2H), 3.86 (s, 2H), 3.23 (s, 2H), 2.6 (s, 2H), 2.4 (s, 2H), 1.6-1.73 (m, 4H), 1.44 (m, 2H), 1.26 (m, 2H), 0.85 (s, 2H).

Example 110

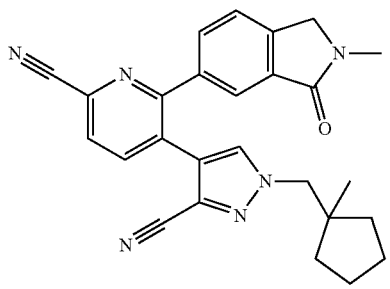 [SMILES: CN1Cc2ccc(-c3nc(C#N)ccc3-c3cn(CC4(C)CCCC4)nc3C#N)cc2C1=O]

5-(3-Cyano-1-((1-methylcyclopentyl)methyl)-1H-pyrazol-4-yl)-6-(2-methyl-3-oxoisoindolin-5-yl)picolinonitrile (Scheme 6)

A mixture of 5-(5-chloro-1-((1-methylcyclopentyl)methyl)-1H-pyrazol-4-yl)-6-(2-methyl-3-oxoisoindolin-5-yl)picolinonitrile (Example 79, 11.4 mg, 0.026 mmol), dicyanozinc (9.0 mg, 0.077 mmol) and chloro(2-dicyclohexylphosphino-2',4',6'-triisopropyl-1,1'-biphenyl)[2-(2'-amino-1,1'-biphenyl)]palladium(II) (2.01 mg, 2.56 µmol) in DMF (4 mL) was heated to 200° C. under microwave irradiation for 30 min. The crude reaction was concentrated and directly purified by column chromatography on silica gel (20:1 CH$_2$Cl$_2$/MeOH) to afford the title compound. MS: 437 (M+1). $^1$H NMR (500 MHz, CDCl$_3$): δ 8.01 (d, J=7.5 Hz, 1H), 7.80 (d, J=8 Hz, 1H), 7.76 (dd, J=7.5, 1.5 Hz, 1H), 7.73 (s, 1H), 7.54 (d, J=8 Hz, 1H), 7.62 (dd, J=8, 1.5 Hz, 1H), 7.30 (s, 1H), 4.44 (s, 2H), 4.16 (s, 2H), 3.22 (s, 3H), 1.73-1.27 (m, 8H), 0.95 (s, 3H).

Example 111

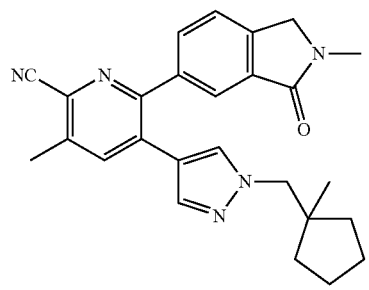 [SMILES: Cc1cc(-c2cnn(CC3(C)CCCC3)c2)c(-c2ccc3c(c2)C(=O)N(C)C3)nc1C#N]

3-Methyl-6-(2-methyl-3-oxoisoindolin-5-yl)-5-(1-((1-methylcyclopentyl)methyl)-1H-pyrazol-4-yl)picolinonitrile (Scheme 6)

6-(6-Chloro-5-methyl-3-(1-((1-methylcyclopentyl)methyl)-1H-pyrazol-4-yl)pyridin-2-yl)-2-methylisoindolin-1-one (Example 38, 70 mg, 0.161 mmol), bis(tri-tert-butylphosphine)palladium(0) (8.22 mg, 0.016 mmol) and zinc cyanide (0.020 mL, 0.322 mmol) were dissolved in dioxane (1.5 mL) in a sealed tube. The reaction was heated at 180° C. under microwave irradiation for 15 min and the mixture was filtered and the solvent was removed under reduced pressure. The residue was dissolved in EtOAc and washed with aqueous saturated NaHCO$_3$, water, and brine and the organic was dried over anhydrous Na$_2$SO$_4$, filtered and concentrated. The material was purified by silica gel chromatography (5-100% EtOAc/hexanes) to give the title compound. MS: 426 (M+1). $^1$H NMR (500 MHz, CDCl$_3$): δ 7.90 (s, 1H), 7.75 (s, 1H), 7.62 (d, J=6.5 Hz, 1H), 7.49 (d, J=8 Hz, 1H), 7.39 (s, 1H), 6.94 (s, 1H), 4.45 (s, 2H), 3.90 (s, 2H), 3.24 (s, 3H), 2.66 (s, 3H), 1.63 (m, 4H), 1.43 (m, 4H), 0.85 (s, 3H).

The following examples in Table 5 were prepared according to Scheme 6 using the procedure outlined in the synthesis of Example 111 using prepared intermediates with alternative conditions being in DMF using chloro(2-dicyclohexylphosphino-2',4',6'-triisopropyl-1,1'-biphenyl)[2-(2'-amino-1,1'-biphenyl)]palladium(II) catalyst.

TABLE 5

| Example | Structure | Name | MS (M + 1) |
|---|---|---|---|
| 112 | 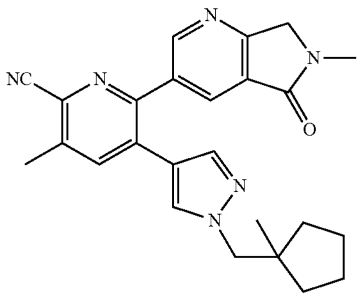 [SMILES: Cc1cc(-c2cnn(CC3(C)CCCC3)c2)c(-c2cnc3c(c2)C(=O)N(C)C3)nc1C#N] | 3-methyl-6-(6-methyl-5-oxo-6,7-dihydro-5H-pyrrolo[3,4-b]pyridin-3-yl)-5-(1-((1-methylcyclopentyl)-methyl)-1H-pyrazol-4-yl)picolinonitrile | 427 |
| 112A | 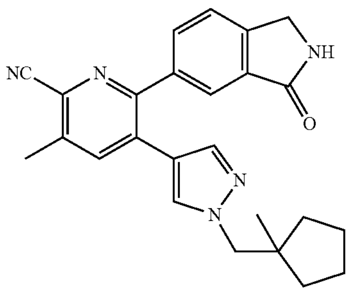 [SMILES: Cc1cc(-c2cnn(CC3(C)CCCC3)c2)c(-c2ccc3c(c2)C(=O)NC3)nc1C#N] | 3-methyl-5-(1-((1-methylcyclopentyl)methyl)-1H-pyrazol-4-yl)-6-(3-oxoisoindolin-5-yl)picolinonitrile | 412 |

Example 113

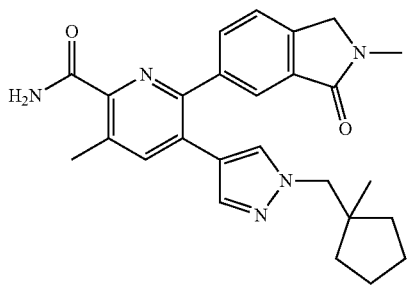 [SMILES: Cc1cc(-c2cnn(CC3(C)CCCC3)c2)c(-c2ccc3c(c2)C(=O)N(C)C3)nc1C(N)=O]

3-Methyl-6-(2-methyl-3-oxoisoindolin-5-yl)-5-(1-((1-methylcyclopentyl)methyl)-1H-pyrazol-4-yl) picolinamide (Scheme 7)

To 3-methyl-6-(2-methyl-3-oxoisoindolin-5-yl)-5-(1-((1-methylcyclopentyl)-methyl)-1H-pyrazol-4-yl)picolinonitrile (Example 111, 19 mg, 0.045 mmol) in methanol (1 mL) was added sodium hydroxide (1 M in water, 0.447 mL, 0.447 mmol). The system was heated to 60° C. for 2 h before filtration and purification purified by mass triggered reverse phase HPLC (ACN/water with 0.1% $NH_3OH$ modifier) to give the title compound. MS: 444 (M+1). $^1$H NMR (500 MHz, $CDCl_3$): δ 8.03 (d, J=1.1 Hz, 1H), 7.95 (d, J=3.6 Hz, 1H), 7.69 (s, 1H), 7.53 (dd, J=8 Hz, 1.7 Hz, 1H), 7.40 (d, J=8.5 Hz, 1H), 7.35 (s, 1H), 6.97 (s, 1H), 5.46 (d, J=3.6 Hz, 1H), 4.43 (s, 2H), 3.89 (s, 2H), 3.25 (s, 3H), 2.83 (s, 3H), 1.57-1.68 (m, 4H), 1.45-1.50 (m, 2H), 1.25-1.31 (m, 2H), 0.87 (s, 3H).

The following example in Table 6 was prepared according to Scheme 6 using the procedure outlined in the synthesis of Example 111 using prepared intermediates with alternative conditions being in DMF using chloro(2-dicyclohexylphosphino-2',4',6'-triisopropyl-1,1'-biphenyl)[2-(2'-amino-1,1'-biphenyl)]palladium(II) catalyst.

TABLE 6

| Example | Structure | Name | MS (M + 1) |
|---|---|---|---|
| 113A | 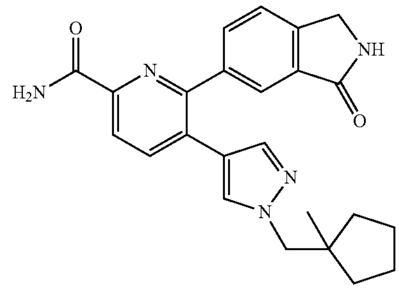 [SMILES: CC1(Cn2cc(-c3ccc(C(N)=O)nc3-c3ccc4c(c3)C(=O)NC4)cn2)CCCC1] | 5-(1-((1-methylcyclopentyl)methyl)-1H-pyrazol-4-yl)-6-(3-oxoisoindolin-5-yl)picolinamide | 416 |

Example 114

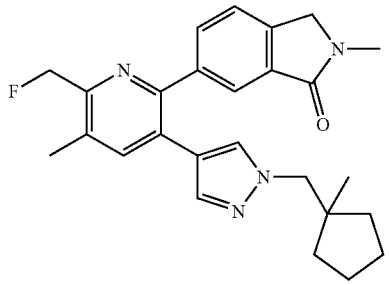 [SMILES: Cc1cc(-c2cnn(CC3(C)CCCC3)c2)c(-c2ccc3c(c2)C(=O)N(C)C3)nc1CF]

6-(6-(Fluoromethyl)-5-methyl-3-(1-((1-methylcyclopentyl)methyl)-1H-pyrazol-4-yl)pyridin-2-yl)-2-methylisoindolin-1-one (Scheme 8)

To a solution of 6-(6-(hydroxymethyl)-5-methyl-3-(1-((1-methylcyclopentyl)methyl)-1H-pyrazol-4-yl)pyridin-2-yl)-2-methylisoindolin-1-one (Example 77, 14 mg, 0.033 mmol) in DCM (2 mL) was added DAST (5.16 μL, 0.039 mmol) at 0° C. The reaction mixture was stirred for 1 h at RT before it was quenched with aqueous sodium hydrogen carbonate. The product was extracted with chloroform and the organic was washed with brine, then dried over anhydrous $Na_2SO_4$, filtered and concentrated under reduced pressure. The residue was purified by prep-TLC (50% 3:1 EtOAc:EtOH/hexanes) to give the title compound. MS: 433 (M+1). $^1$H NMR (500 MHz, $CDCl_3$): δ 7.95 (s, 1H), 7.65 (s, 1H), 7.58 (dt, J=8, 1.8 Hz, 1H), 7.41 (d, J=7.8 Hz, 1H), 7.33 (s, 1H), 6.9 (s, 1H), 5.58 (d, J=47.6 Hz, 2H), 4.41 (s, 2H), 3.87 (s, 2H), 3.23 (s, 3H), 2.54 (s, 3H), 1.56-1.68 (m, 4H), 1.44 (m, 2H), 1.26 (m, 2H), 0.85 (s, 3H).

The following example in Table 6 was prepared according to Scheme 8 using the procedure outlined in the synthesis of Example 114 using prepared intermediates.

Example 116

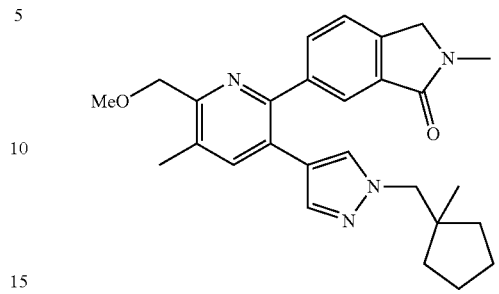

6-(6-(Methoxymethyl)-5-methyl-3-(1-((1-methylcyclopentyl)methyl)-1H-pyrazol-4-yl)pyridin-2-yl)-2-methylisoindolin-1-one (Scheme 8)

To a solution of 6-(6-(hydroxymethyl)-5-methyl-3-(1-((1-methylcyclopentyl)methyl)-1H-pyrazol-4-yl)pyridin-2-yl)-2-methylisoindolin-1-one (Example 77, 18 mg, 0.042 mmol) in THF (1 mL) was added sodium hydride (5.02 mg, 0.125 mmol) at 0° C. After 15 min, iodomethane (17.80 mg, 0.125 mmol) was added and the reaction was stirred for 30 min, before warming to RT for 1 h. The reaction was quenched with saturated aqueous $NaHCO_3$ and was partitioned with EtOAc. The organic layer was separated, dried over anhydrous sodium sulfate, filtered and concentrated to dryness. The crude material was purified by mass triggered reverse phase HPLC (ACN/water with 0.1% $NH_3OH$ modifier) to afford the title compound. MS: 445 (M+1). $^1$H NMR (500 MHz, $CDCl_3$): δ 7.97 (s, 1H), 7.6 (s, 1H), 7.56 (d, J=7.7 Hz, 1H), 7.4 (d, J=7.7 Hz, 1H), 7.32 (s, 1H), 6.87 (s, 1H), 4.68 (s, 2H), 4.4 (s, 2H), 3.86 (s, 2H), 3.47 (s, 3H), 3.23 (s, 3H), 2.50 (s, 3H), 1.55-1.68 (m, 4H), 1.44 (m, 2H), 1.25 (m, 2H), 0.85 (s, 3H).

TABLE 6

| Example | Structure | Name | MS (M + 1) |
|---|---|---|---|
| 115 | 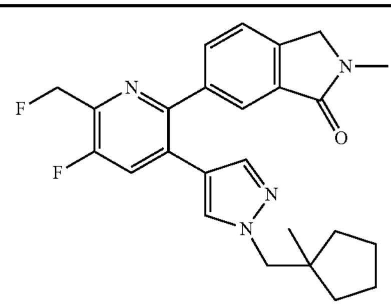 | 6-(5-fluoro-6-(fluoromethyl)-3-(1-((1-methylcyclopentyl)-methyl)-1H-pyrazol-4-yl)pyridin-2-yl)-2-methylisoindolin-1-one | 437 |

Example 117

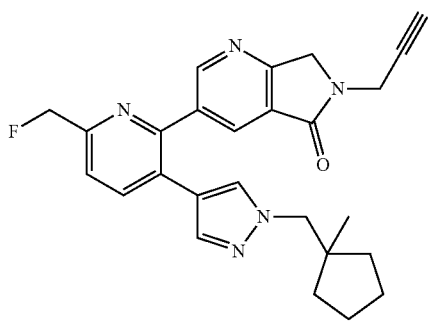 [SMILES: C#CCN1Cc2ncc(-c3nc(CF)ccc3-c3cnn(CC4(C)CCCC4)c3)cc2C1=O]

3-(6-(Fluoromethyl)-3-(1-((1-methylcyclopentyl)
methyl)-1H-pyrazol-4-yl)pyridin-2-yl)-6-(prop-2-yn-
1-yl)-6,7-dihydro-5H-pyrrolo[3,4-b]pyridin-5-one
(Scheme 9)

Step 1: 3-(6-(Fluoromethyl)-3-(1-((1-methylcyclo-
pentyl)methyl)-1H-pyrazol-4-yl)pyridin-2-yl)-6,7-
dihydro-5H-pyrrolo[3,4-b]pyridin-5-one To a degassed solution of 3-(4,4,5,5-tetramethyl-1,3,2-dioxaborolan-2-yl)-6,7-dihydro-5H-pyrrolo[3,4-b]pyridin-5-one (intermediate C1, 150 mg, 0.192 mmol), 2-chloro-6-(fluoromethyl)-3-(1-((1-methylcyclopentyl)methyl)-1H-pyrazol-4-yl)pyridine (intermediate G15, 59.2 mg, 0.192 mmol) and potassium phosphate (82 mg, 0.384 mmol) in dioxane (2 mL) and water (0.2 mL) was added 1,1'-bis(di-tert-butylphosphino)ferrocene palladium dichloride (12.5 mg, 0.019 mmol) at 25° C. in a Schlenk tube under $N_2(g)$. The resulting mixture was stirred at 50° C. for 3 h and the mixture was diluted with EtOAc (20 mL) and water (10 mL) before being filtered through celite pad. The filtrate was separated and the aqueous phase was extracted with EtOAc (20 mL×3). The combined organic layers were washed with water (20 mL) and brine (15 mL), dried over anhydrous sodium sulfate, filtered and concentrated. The crude product was purified by prep-TLC (1:1 petroleum ether/EtOAc) to the title compound. MS: 406 (M+1).

Step 2: 3-(6-(Fluoromethyl)-3-(1-((1-methylcyclo-
pentyl)methyl)-1H-pyrazol-4-yl)pyridin-2-yl)-6-
(prop-2-yn-1-yl)-6,7-dihydro-5H-pyrrolo[3,4-b]pyri-
din-5-one To a solution of 3-(6-(fluoromethyl)-3-(1-((1-methylcyclopentyl)methyl)-1H-pyrazol-4-yl)pyridin-2-yl)-6,7-dihydro-5H-pyrrolo[3,4-b]pyridin-5-one (30 mg, 0.074 mmol) in dry THF (1 mL) at 0° C. was added NaH (2.96 mg, 0.074 mmol) in a Schlenk tube. After 30 min at 0° C., 3-bromoprop-1-yne (8.80 mg, 0.074 mmol) was added and the mixture was warmed to 25° C. The mixture was stirred for 16 h at RT before being diluted with saturated aqueous $NH_4Cl$ (0.1 mL). The reaction was concentrated and purified by reverse phase HPLC (MeCN/water with 0.1% TFA modifier) to afford the title compound. MS: 444 (M+1). $^1H$ NMR (400 MHz, methanol-$d_4$): δ 0.79 (3H, s), 1.18-1.25 (4H, m), 1.40 (4H, dd, J=12.13, 6.65 Hz), 3.84 (2H, s), 4.48 (2H, s), 5.42 (1H, s), 5.54 (1H, s), 6.27 (1H, br. s.), 6.94 (1H, s), 7.24 (1H, s), 7.48 (1H, d, J=7.83 Hz), 7.80 (1H, d, J=7.83 Hz), 8.18 (1H, s), 8.75 (1H, s).

The following example in Table 7 was prepared according to Scheme 9 using the procedure outlined in the synthesis of Example 117 using prepared intermediates and commercially available alkyl halides.

TABLE 7

| Example | Structure | Name | MS (M + 1) |
|---------|-----------|------|------------|
| 118 | 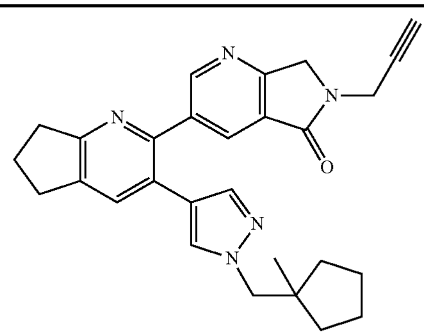 | 3-(3-(1-((1-methylcyclopentyl)methyl)-1H-pyrazol-4-yl)-6,7-dihydro-5H-cyclopenta[b]pyridin-2-yl)-6-(prop-2-yn-1-yl)-6,7-dihydro-5H-pyrrolo[3,4-b]pyridin-5-one | 452 |
| 118A | 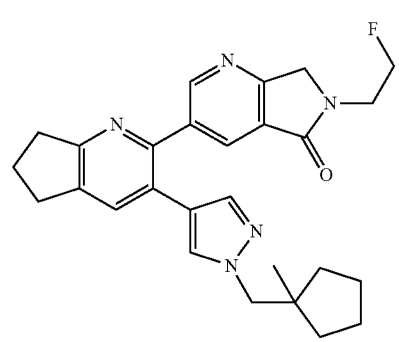 [SMILES: CC1(Cn2cc(-c3cc4c(nc3-c3cnc5c(c3)C(=O)N(CCF)C5)CCC4)cn2)CCCC1] | 6-(2-fluoroethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 460 |

TABLE 7-continued

| Example | Structure | Name | MS (M + 1) |
| --- | --- | --- | --- |
| 119 | 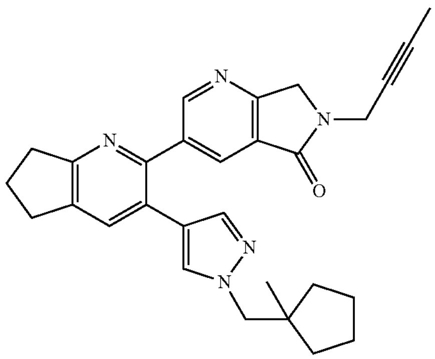 [SMILES: CC#CCN1Cc2ncc(-c3nc4c(cc3-c3cnn(CC5(C)CCCC5)c3)CCC4)cc2C1=O] | 6-(but-2-yn-1-yl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one | 466 |
| 120 | 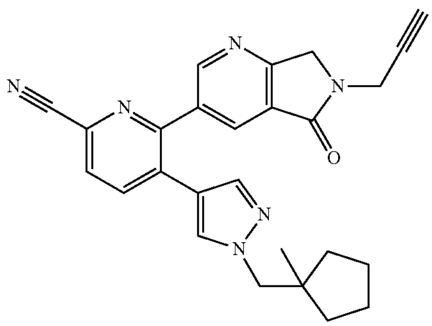 [SMILES: C#CCN1Cc2ncc(-c3nc(C#N)ccc3-c3cnn(CC4(C)CCCC4)c3)cc2C1=O] | 5-(1-((1-methylcyclopentyl)methyl)-1H-pyrazol-4-yl)-6-(5-oxo-6-(prop-2-yn-1-yl)-6,7-dihydro-5H-pyrrolo[3,4-b]pyridin-3-yl)picolinonitrile | 437 |
| 120A | 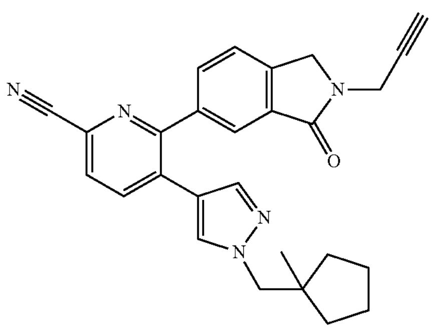 [SMILES: C#CCN1Cc2ccc(-c3nc(C#N)ccc3-c3cnn(CC4(C)CCCC4)c3)cc2C1=O] | 5-(1-((1-methylcyclopentyl)methyl)-1H-pyrazol-4-yl)-6-(3-oxo-2-((prop-2-yn-1-yl)isoindolin-5-yl)picolinonitrile | 436 |
| 121 | 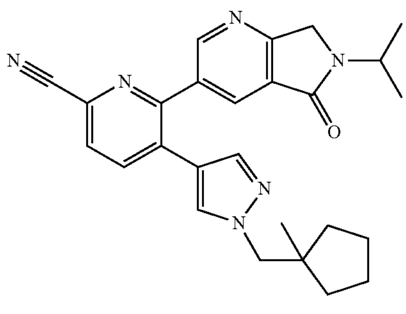 [SMILES: CC(C)N1Cc2ncc(-c3nc(C#N)ccc3-c3cnn(CC4(C)CCCC4)c3)cc2C1=O] | 6-(6-isopropyl-5-oxo-6,7-dihydro-5H-pyrrolo[3,4-b]pyridin-3-yl)-5-(1-((1-methylcyclopentyl)methyl)-1H-pyrazol-4-yl)picolinonitrile | 441 |

TABLE 7-continued

| Example | Structure | Name | MS (M + 1) |
|---|---|---|---|
| 122 | 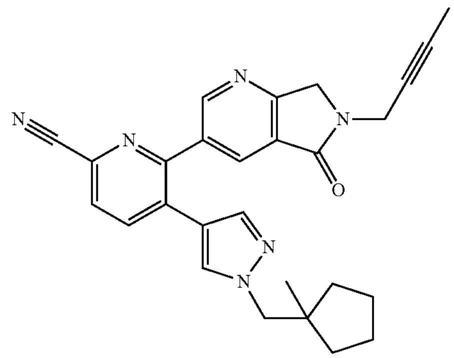 [SMILES: CC#CCN1Cc2ncc(-c3nc(C#N)ccc3-c3cnn(CC4(C)CCCC4)c3)cc2C1=O] | 6-(6-(but-2-yn-1-yl)-5-oxo-6,7-dihydro-5H-pyrrolo[3,4-b]pyridin-3-yl)-5-(1-((1-methylcyclopentyl)methyl)-1H-pyrazol-4-yl)picolinonitrile | 451 |
| 123 | 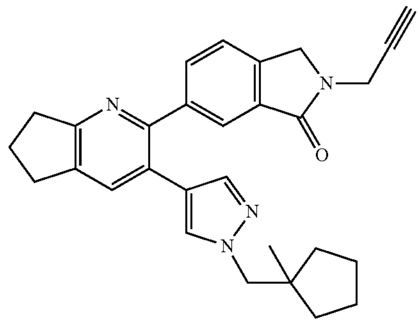 [SMILES: C#CCN1Cc2ccc(-c3nc4c(cc3-c3cnn(CC5(C)CCCC5)c3)CCC4)cc2C1=O] | 6-(3-(1-((1-methylcyclopentyl)methyl)-1H-pyrazol-4-yl)-6,7-dihydro-5H-cyclopenta[b]pyridin-2-yl)-2-(prop-2-yn-1-yl)isoindolin-1-one | 451 |

Example 124

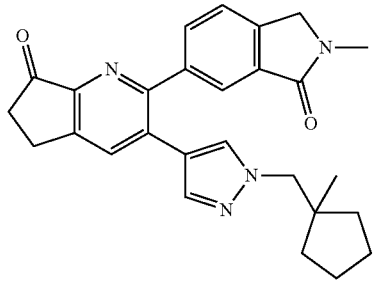 [SMILES: CN1Cc2ccc(-c3nc4c(cc3-c3cnn(CC5(C)CCCC5)c3)CCC4=O)cc2C1=O]

2-(2-Methyl-3-oxoisoindolin-5-yl)-3-(1-((1-methylcyclopentyl)methyl)-1H-pyrazol-4-yl)-5,6-dihydro-7H-cyclopenta[b]pyridin-7-one Step 1: 2-(2-Methyl-3-oxoisoindolin-5-yl)-3-(1-((1-methylcyclopentyl)methyl)-1H-pyrazol-4-yl)-6,7-dihydro-5H-cyclopenta[b]pyridin-7-yl acetate To a vial was added 2-chloro-3-(1-((1-methylcyclopentyl)methyl)-1H-pyrazol-4-yl)-6,7-dihydro-5H-cyclopenta[b]pyridin-7-yl acetate (intermediate G18, 40 mg, 0.107 mmol), THF (3 mL), water (0.3 mL), 2-methyl-6-(4,4,5,5-tetramethyl-1,3,2-dioxaborolan-2-yl)isoindolin-1-one (intermediate C1, 35.1 mg, 0.128 mmol), K$_3$PO$_4$ (68.1 mg, 0.321 mmol) and 1,1'-bis(di-tert-butylphosphino)ferrocene palladium dichloride (6.97 mg, 10.70 µmol). The reaction mixture was placed under N$_2$(g) and was stirred for 2 h at 40° C. The reaction mixture was filtered and was concentrated in vacuo before purification by purified by prep-TLC (100% EtOAc) to give the title compound. MS: 485 (M+1).

Step 2: 6-(7-Hydroxy-3-(1-((1-methylcyclopentyl)methyl)-1H-pyrazol-4-yl)-6,7-dihydro-5H-cyclopenta[b]pyridin-2-yl)-2-methylisoindolin-1-one To a vial was added 2-(2-methyl-3-oxoisoindolin-5-yl)-3-(1-((1-methylcyclopentyl)methyl)-1H-pyrazol-4-yl)-6,7-dihydro-5H-cyclopenta[b]pyridin-7-yl acetate (35 mg, 0.072 mmol), MeOH (3 mL), water (0.3 mL) and sodium hydroxide (5.78 mg, 0.144 mmol). The reaction mixture was stirred for 1.5 h at 28° C. before being concentrated under reduced pressure. The residue was dissolved in EtOAc (30 mL) and was stirred for 10 min, before being filtered and concentrated to give the title compound, which was carried forward without further purification. MS: 443 (M+1).

Step 3: 2-(2-Methyl-3-oxoisoindolin-5-yl)-3-(1-((1-methylcyclopentyl)methyl)-1H-pyrazol-4-yl)-5,6-dihydro-7H-cyclopenta[b]pyridin-7-one To a vial was added 6-(7-hydroxy-3-(1-((1-methylcyclopentyl)methyl)-1H-pyrazol-4-yl)-6,7-dihydro-5H-cyclopenta[b]pyridin-2-yl)-2-methylisoindolin-1-one (22 mg, 0.050 mmol), DCM (5 mL) and manganese(IV) oxide (43.2 mg, 0.497 mmol). The mixture was stirred for 3 h at 28° C. after which the reaction mixture was filtered and concentrated to dryness. The resultant residue was purified by reverse phase HPLC (MeCN/water with 0.1% TFA modifier) to give the title compound. MS: 441 (M+1). $^1$H NMR (400 MHz, methanol-d$_4$): δ 8.18 (1H, s), 7.63-7.69 (3H, m), 7.43 (1H, s), 7.12 (1H, s), 4.53 (2H, s), 3.86 (2H, s), 3.23-3.26

(2H, m), 3.18 (3H, s), 2.77-2.81 (2H, m), 1.54-1.59 (4H, m), 1.35-1.39 (2H, m), 1.16-1.17 (2H, m), 1.11-1.20 (2H, m), 0.76 (3H, s).

Example 125

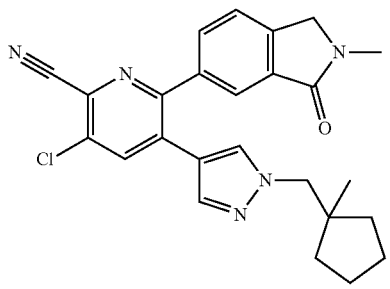 [SMILES: CN1Cc2ccc(-c3nc(C#N)c(Cl)cc3-c3cnn(CC4(C)CCCC4)c3)cc2C1=O]

3-Chloro-6-(2-methyl-3-oxoisoindolin-5-yl)-5-(1-((1-methylcyclopentyl)methyl)-1H-pyrazol-4-yl)picolinonitrile (Scheme 11)

To a solution of 3-amino-6-(2-methyl-3-oxoisoindolin-5-yl)-5-(1-((1-methylcyclopentyl)methyl)-1H-pyrazol-4-yl)picolinonitrile (Example 51, 50 mg, 0.117 mmol) in water (3 mL) was added HCl (37%, 3 mL, 36.5 mmol). The solution was stirred at 0° C. before sodium nitrite (12.13 mg, 0.176 mmol) in water (0.5 mL) was added dropwise. The reaction was stirred 20 min at 0° C. Copper(I) chloride (15.0 mg, 0.152 mmol) was added to the reaction mixture and the system was heat for 30 min at 80° C. The reaction cooled and neutralized with NaOH (2 M in water) and extracted with DCM (10 mL×3). The combined organics were dried over anhydrous $Na_2SO_4$, filtered and concentrated. The residue was purified by reverse phase HPLC (MeCN/water with 0.1% TFA modifier) to give the title compound. MS: 446 (M+1). $^1$H NMR (400 MHz, methanol-$d_4$): δ 8.29 (1H, s), 7.76 (1H, s), 7.60-7.75 (2H, m), 7.46 (1H, s), 7.26 (1H, s), 4.58 (2H, s), 3.91 (2H, s), 3.22 (3H, s), 1.65-1.70 (4H, m), 1.35-1.45 (2H, m), 1.15-1.25 (2H, m), 0.82 (3H, s).

Example 126

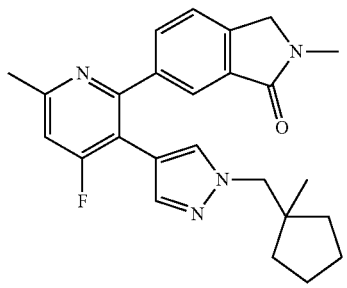 [SMILES: Cc1cc(F)c(-c2cnn(CC3(C)CCCC3)c2)c(-c2ccc3c(c2)C(=O)N(C)C3)n1]

6-(4-fluoro-6-methyl-3-(1-((1-methylcyclopentyl)methyl)-1H-pyrazol-4-yl)pyridin-2-yl)-2-methylisoindolin-1-one (Scheme 12)

Sodium nitrite (4.98 mg, 0.072 mmol) was added to a stirred, cooled 0° C. mixture of 6-(4-amino-6-methyl-3-(1-((1-methylcyclopentyl)methyl)-1H-pyrazol-4-yl)pyridin-2-yl)-2-methylisoindolin-1-one (Example 62, 5 mg, 0.012 mmol) in hydrogen fluoride-pyridine (23.85 mg, 0.241 mmol). The reaction was heated to 60° C. and was then stirred at 30° C. for 2 h. The reaction was quenched with an ice-cold saturated solution of aqueous $Na_2CO_3$. The organic layer was separated and concentrated to dryness. The crude material was purified by prep-TLC (100:10:1 hexanes/3:1 EtOAc:MeOH/$NH_3$OH) to give the title compound. MS: 419 (M+1). $^1$H NMR (500 MHz, CDCl$_3$): δ 7.94 (1H, s), 7.54 (1H, dd, J=8 Hz, 1.8 Hz), 7.39 (1H, d, J=7.8 Hz), 7.17 (1H, s), 7.12 (1H, s), 7.0 (1H, d, J=10.3 Hz), 4.40 (2H, s), 3.92 (2H, s), 3.21 (3H, s), 2.63 (3H, s), 1.58-1.66 (m, 8H), 1.44-1.51 (4H, m), 0.86 (3H, s).

Example 127

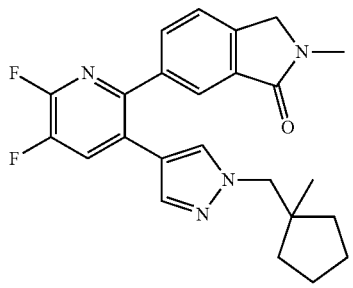 [SMILES: CN1Cc2ccc(-c3nc(F)c(F)cc3-c3cnn(CC4(C)CCCC4)c3)cc2C1=O]

6-(5,6-Difluoro-3-(1-((1-methylcyclopentyl)methyl)-1H-pyrazol-4-yl)pyridin-2-yl)-2-methylisoindolin-1-one (Scheme 13)

Step 1: 6-(3-Chloro-5,6-difluoropyridin-2-yl)-2-methylisoindolin-1-one

3-Chloro-5,6-difluoro-2-iodopyridine (100 mg, 0.363 mmol), 2-methyl-6-(4,4,5,5-tetramethyl-1,3,2-dioxaborolan-2-yl)isoindolin-1-one (intermediate C1, 99 mg, 0.363 mmol), PdCl$_2$(dppf) (26.6 mg, 0.036 mmol) and potassium carbonate (1 M in water, 1.45 mL, 1.45 mmol) were added into a vial with dioxane (5 mL). The system was degassed three times before it was heated to 50° C. for 4 h. The reaction mixture was cooled to RT and diluted with water and EtOAc. The organic was separated, dried over anhydrous sodium sulfate, and was concentrated to dryness. The resultant residue was purified by silica gel chromatography (0-40% EtOAc/hexanes) to afford the title compound. MS: 295 (M+1).

Step 2: 6-(5,6-Difluoro-3-(1-((1-methylcyclopentyl)methyl)-1H-pyrazol-4-yl)pyridin-2-yl)-2-methylisoindolin-1-one 6-(3-Chloro-5,6-difluoropyridin-2-yl)-2-methylisoindolin-1-one (15 mg, 0.051 mmol), 1-((1-methylcyclopentyl)methyl)-4-(4,4,5,5-tetramethyl-1,3,2-dioxaborolan-2-yl)-1H-pyrazole (intermediate A, 14.8 mg, 0.051 mmol), 1,1'-bis(di-tert-butylphosphino)ferrocene palladium (2.65 mg, 4.07 μmol) and potassium carbonate (1 M in water, 0.153 mL, 0.153 mmol) were added into a vial with dioxane (1 mL). The system was degassed three times and was stirred at RT for 2 h, and then at 100° C. for 5 h. The reaction mixture was cooled to RT and diluted with water and EtOAc.

The organic was separated, dried over anhydrous sodium sulfate, and was concentrated to dryness. The crude material was purified by silica gel chromatography (0-30% 3:1 EtOAc:EtOH/hexanes) to afford the title compound. MS: 423 (M+1). $^1$H NMR (500 MHz, CDCl$_3$): δ 7.9 (s, 1H), 7.67 (t, J=8.5 Hz, 1H), 7.57 (d, J=7 Hz, 1H), 7.43 (d, J=7 Hz, 1H), 7.29 (s, 1H), 6.95 (s, 1H), 4.41 (s, 2H), 3.89 (s, 2H), 3.23 (s, 3H), 1.61 (m, 4H), 1.43 (m, 4H), 0.85 (s, 3H).

Example 128

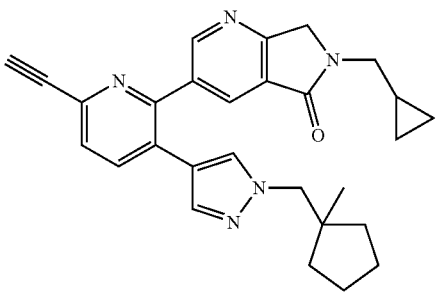 [SMILES: C#Cc1ccc(-c2cnn(CC3(C)CCCC3)c2)c(-c2cnc3c(c2)C(=O)N(CC2CC2)C3)n1]

6-(Cyclopropylmethyl)-3-(6-ethynyl-3-(1-((1-methylcyclopentyl)methyl)-1H-pyrazol-4-yl)pyridin-2-yl)-6,7-dihydro-5H-pyrrolo[3,4-b]pyridin-5-one
(Scheme 14)

Step 1: 3-Bromo-2-chloro-6-ethynylpyridine

To a solution of 5-bromo-6-chloropicolinaldehyde (900 mg, 4.08 mmol) and dimethyl (1-diazo-2-oxopropyl)phosphonate (1.57 g, 8.17 mmol) in MeOH (10 mL) was added K$_2$CO$_3$ (1.41 g, 10.21 mmol). The reaction mixture was stirred at 20° C. for 2 h before adding water (100 mL) and partitioning with EtOAc (3×100 mL). The combined organic layers were washed with brine (80 mL), dried over anhydrous Na$_2$SO$_4$, filtered and the filtrate was concentrated in vacuo. The crude product was purified by silica gel chromatography (15% EtOAc/petroleum ether) to give the title compound. MS: 217 (M+1).

Step 2: 3-Bromo-2-chloro-6-((triisopropylsilyl)ethynyl)pyridine

To a solution of 3-bromo-2-chloro-6-ethynylpyridine (550 mg, 2.54 mmol) in DMF (8 mL) was added NaH (203 mg, 5.08 mmol) at 0° C. The reaction mixture was stirred at for 30 min at 0° C. and then chlorotriisopropylsilane (637 mg, 3.30 mmol) was added. The reaction was allowed to warm to 20° C. and was stirred for 1.5 h. The reaction mixture was diluted with water (80 mL) and extracted with EtOAc (3×50 mL). The combined organic layers were washed with brine (30 mL), dried over Na$_2$SO$_4$, filtered and the filtrate was concentrated in vacuo. The crude product was purified by silica gel chromatography (100% petroleum ether) to yield the title compound. MS: 372, 374 (M+1)

Step 3: 2-Chloro-3-(1-((1-methylcyclopentyl)methyl)-1H-pyrazol-4-yl)-6-((triisopropylsilyl)ethynyl)pyridine To a solution of 1-((1-methylcyclopentyl)methyl)-4-(4,4,5,5-tetramethyl-1,3,2-dioxaborolan-2-yl)-1H-pyrazole (intermediate A, 234 mg, 0.805 mmol) and 3-bromo-2-chloro-6-((triisopropylsilyl)ethynyl)pyridine (250 mg, 0.671 mmol) in 1,4-dioxane (2 mL) and water (0.7 mL) were added tripotassium phosphate trihydrate (446 mg, 1.68 mmol) and 1,1'-bis(di-tert-butylphosphino)ferrocene palladium dichloride (43.7 mg, 0.067 mmol) under an atmosphere of N$_2$(g). The reaction mixture was stirred at 50° C. for 2 h. After cooling to RT, the reaction mixture was diluted with water (50 mL) and extracted with EtOAc (3×50 mL). The combined organic layers were washed with brine (20 mL), dried over anhydrous Na$_2$SO$_4$, filtered and the filtrate was concentrated in vacuo. The residue was purified by prep-TLC (9% EtOAc/petroleum ether) to give the title compound. MS: 457 (M+1).

Step 4: 6-(Cyclopropylmethyl)-3-(3-(1-((1-methylcyclopentyl)methyl)-1H-pyrazol-4-yl)-6-((triisopropylsilyl)ethynyl)pyridin-2-yl)-6,7-dihydro-5H-pyrrolo[3,4-b]pyridin-5-one To a solution of 3-bromo-6-(cyclopropylmethyl)-6,7-dihydro-5H-pyrrolo[3,4-b]pyridin-5-one (100 mg, 0.374 mmol) and bis(pinacolato)diboron (143 mg, 0.562 mmol) in 1,4-dioxane (2 mL) was added potassium acetate (92 mg, 0.936 mmol) and PdCl$_2$(dppf) (27.4 mg, 0.037 mmol) under an atmosphere of N$_2$(g). The reaction mixture was stirred at 90° C. for 2 h and then tripotassium phosphate trihydrate (199 mg, 0.749 mmol), 2-chloro-3-(1-((1-methylcyclopentyl)-methyl)-1H-pyrazol-4-yl)-6-((triisopropylsilyl)ethynyl) pyridine (171 mg, 0.374 mmol), water (0.7 mL), and 1,1'-bis(di-tert-butylphosphino)ferrocene palladium dichloride was added under an atmosphere of N$_2$(g). The reaction mixture was stirred at 90° C. for 1.5 h. The reaction mixture was cooled to RT, diluted with water (50 mL) and extracted with EtOAc (3×90 mL). The combined organic layers were washed with brine (40 mL), dried over anhydrous Na$_2$SO$_4$, filtered and the filtrate was concentrated in vacuo. The residue was purified by prep-TLC (25% EtOAc/petroleum ether) to yield the title compound. MS: 609 (M+1).

Step 6: 6-(Cyclopropylmethyl)-3-(6-ethynyl-3-(1-((1-methylcyclopentyl)methyl)-1H-pyrazol-4-yl) pyridin-2-yl)-6,7-dihydro-5H-pyrrolo[3,4-b]pyridin-5-one To a solution of 6-(cyclopropylmethyl)-3-(3-(1-((1-methylcyclopentyl)methyl)-1H-pyrazol-4-yl)-6-((triisopropylsilyl)ethynyl)pyridin-2-yl)-6,7-dihydro-5H-pyrrolo[3,4-b] pyridin-5-one (86 mg, 0.141 mmol) in THF (2 mL) was added TBAF (0.424 mL, 0.424 mmol) at 0° C. The reaction mixture was allowed to warm to RT and was stirred for 12 h. The reaction mixture was diluted with water (50 mL) and extracted with EtOAc (3×50 mL). The combined organic layers were washed with brine (10 mL), dried over anhydrous Na$_2$SO$_4$, filtered and the filtrate was concentrated in vacuo. The residue was purified by reverse phase HPLC (ACN/water with 0.1% TFA modifier) to yield the title compound. MS: 452 (M+1). $^1$H NMR (400 MHz, methanol-d$_4$): δ 8.82 (1H, s), 8.26 (1H, s), 7.42 (1H, d, J=8.0 Hz), 7.25 (1H, d, J=7.6 Hz), 7.32 (1H, m), 7.04 (1H, s), 4.65 (2H, s), 3.92 (2H, s), 3.52 (2H, d, J=6.8 Hz), 3.25 (1H, s), 1.62-1.64 (4H, m), 1.43-1.44 (2H, m), 1.27-1.29 (2H, m), 1.10 (1H, m), 0.85 (3H, s), 0.63-0.65 (2H, m), 0.37-0.38 (2H, m).

Example 129

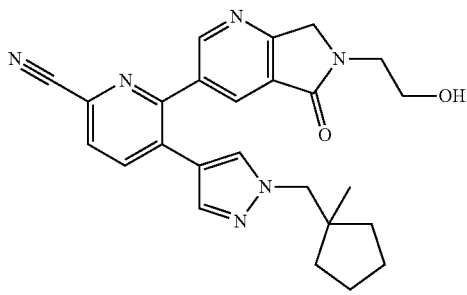 [SMILES: CC1(Cn2cc(-c3ccc(C#N)nc3-c3cnc4c(c3)C(=O)N(CCO)C4)cn2)CCCC1]

6-(6-(2-Hydroxyethyl)-5-oxo-6,7-dihydro-5H-pyrrolo[3,4-b]pyridin-3-yl)-5-(1-((1-methylcyclopentyl)methyl)-1H-pyrazol-4-yl)picolinonitrile (Scheme 15)

To a solution of NaBH$_4$ (39.8 mg, 1.052 mmol) in tert-butanol (3 mL) at 80° C. was added methyl 2-(3-(6-cyano-3-(1-((1-methylcyclopentyl)methyl)-1H-pyrazol-4-yl)pyridin-2-yl)-5-oxo-5H-pyrrolo[3,4-b]pyridin-6(7H)-yl) acetate (99 mg, 0.210 mmol). The reaction was stirred for 10 min and was then directly purified by silica gel chromatography (30/1 DCM/MeOH) to provide the title compound. MS: 443 (M+1). $^1$H NMR (500 MHz, CDCl$_3$): δ 8.79 (1H, s), 8.18 (1H, s), 7.93 (1H, J=8 Hz, d), 7.74 (1H, J=8 Hz, d), 7.33 (1H, s) 7.05 (1H, s), 5.30 (1H, s), 4.61 (2H, s), 3.94-3.96 (2H, m), 3.90-3.92 (2H, m), 3.80-3.83 (2H, m), 1.57-1.67 (3H, m), 1.43-1.48 (2H, m), 1.22-1.29 (3H, m), 0.85 (3H, s).

Assay Protocol

The utility of the compounds as M4 muscarinic receptor allosteric modulators may be demonstrated by methodology known in the art, including by the assay described herein. CHO-K1 cells stably transfected with human M4 receptor and chimeric G-protein Gαqi5 are thawed from liquid N$_2$ storage, resuspended in growth medium, plated in black, clear bottom 384 well plates, and incubated 16-20 hours at 37° C., 5% CO$_2$. On the day of assay, growth medium is removed, the cells are washed 2 times with wash buffer, and cells are incubated in dye loading buffer at 37° C., 5% CO$_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 8

| Example | M4 PAM IP (nM) |
|---|---|
| 1 | 39 |
| 1A | 67 |
| 1B | 75 |
| 2 | 16 |
| 3 | 38 |
| 4 | 37 |
| 5 | 20 |
| 6 | 20 |
| 7 | 22 |
| 8 | 142 |
| 9 | 12 |
| 10 | 54 |
| 11 | 11 |
| 12 | 348 |
| 13 | 613 |
| 14 | 687 |
| 15 | 94 |
| 16 | 297 |
| 17 | 278 |
| 18 | 8 |
| 19 | 9 |
| 20 | 9 |
| 21 | 22 |
| 22 | 28 |
| 23 | 34 |
| 24 | 20 |
| 25 | 21 |
| 26 | 32 |
| 27 | 11 |
| 28 | 10 |
| 29 | 13 |
| 30 | 18 |
| 31 | 74 |
| 32 | 7 |
| 33 | 7 |
| 34 | 15 |
| 34A | 44 |
| 35 | 9 |
| 36 | 6 |
| 37 | 7 |
| 38 | 33 |
| 39 | 37 |
| 39A | 58 |
| 39B | 25 |
| 40 | 49 |
| 41 | 64 |
| 42 | 37 |
| 43 | 20 |
| 43A | 26 |
| 44 | 54 |
| 45 | 41 |
| 46 | 90 |
| 47 | 20 |
| 48 | 76 |
| 49 | 32 |
| 50 | 38 |
| 51 | 75 |
| 52 | 40 |
| 53 | 61 |
| 54 | 8 |
| 55 | 38 |
| 56 | 72 |
| 57 | 44 |
| 58 | 35 |
| 59 | 14 |
| 60 | 99 |
| 61 | 59 |
| 62 | 293 |
| 63 | 489 |
| 64 | 119 |
| 65 | 136 |
| 66 | 39 |
| 67 | 25 |
| 68 | 23 |
| 69 | 34 |
| 70 | 47 |
| 71 | 35 |
| 72 | 41 |

TABLE 8-continued

| Example | M4 PAM IP (nM) |
|---|---|
| 73 | 52 |
| 74 | 24 |
| 75 | 80 |
| 76 | 9 |
| 77 | 85 |
| 78 | 32 |
| 79 | 108 |
| 80 | 26 |
| 81 | 46 |
| 82 | 310 |
| 83 | 100 |
| 84 | 47 |
| 85 | 60 |
| 86 | 62 |
| 87 | 319 |
| 88 | 240 |
| 89 | 32 |
| 90 | 359 |
| 91 | 49 |
| 92 | 45 |
| 93 | 58 |
| 94 | 29 |
| 95 | 21 |
| 96 | 56 |
| 97 | 16 |
| 98 | 29 |
| 99 | 19 |
| 100 | 26 |
| 101 | 18 |
| 102 | 35 |
| 103 | 33 |
| 104 | 14 |
| 105 | 36 |
| 106 | 43 |
| 107 | 15 |
| 108 | 17 |
| 109 | 48 |
| 110 | 86 |
| 111 | 35 |
| 112 | 27 |
| 112A | 36 |
| 113 | 69 |
| 113A | 205 |
| 114 | 57 |
| 115 | 47 |
| 116 | 326 |
| 117 | 32 |
| 118 | 79 |
| 118A | 50 |
| 119 | 71 |
| 120 | 26 |
| 120A | 17 |
| 121 | 134 |
| 122 | 41 |
| 123 | 48 |
| 124 | 30 |
| 125 | 26 |
| 126 | 71 |
| 127 | 90 |
| 128 | 62 |
| 129 | 39 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

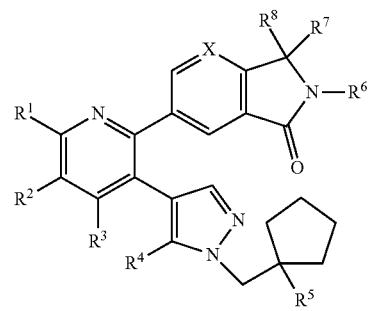

wherein:

X is N or CH;

$R^1$ is selected from the group consisting of:
(1) hydrogen,
(2) halogen,
(3) —CN,
(4) —$C_{1-6}$alkyl, which is unsubstituted or substituted with a hydroxy, or 1-3 fluoro,
(5) —O—$C_{1-6}$alkyl, which is unsubstituted or substituted with a hydroxy, or 1-3 fluoro,
(6) —C≡CH,
(7) —(C=O)—$NH_2$, and
(8) —(C=O)—NH(—$C_{1-6}$alkyl);

$R^2$ is selected from the group consisting of:
(1) hydrogen,
(2) halogen,
(3) —$C_{1-6}$alkyl, and
(4) —$NH_2$,
or $R^1$ and $R^2$ are joined together with a —$(CH_2)_3$— or —(C=O)$(CH_2)_2$— to form a 5-membered ring, which is unsubstituted or substituted with a hydroxy, or 1-3 fluoro,
or $R^1$ and $R^2$ are joined together with a —$(CH_2)_4$—, —(C=O)$(CH_2)_3$—, —$(CH_2)$(C=O)$(CH_2)_2$— to form a 6-membered ring, which is unsubstituted or substituted with a hydroxy, or 1-3 fluoro;

$R^3$ is selected from the group consisting of:
(1) hydrogen,
(2) halogen,
(3) —CN,
(4) —$C_{1-6}$alkyl, and
(5) —$NH_2$;

$R^4$ is selected from the group consisting of:
(1) hydrogen,
(2) —CN,
(3) chloro, and
(4) fluoro;

$R^5$ is selected from the group consisting of:
(1) hydrogen, and
(2) —$CH_3$;

$R^6$ is selected from the group consisting of:
(1) hydrogen,
(2) —$C_{1-6}$alkyl, which is unsubstituted or substituted with a —CN, 1-3 fluoro, or phenyl which is unsubstituted or substituted with a hydroxy or a —$SO_2$—$NH_2$,
(3) —$C_{3-6}$cycloalkyl, which is unsubstituted or substituted with a —CN, or —(C=O)—$NH_2$;
(4) —($CH_{2-5}$cycloalkyl-O—), (5) —C$_{1-6}$alkyl-C$_{3-6}$cycloalkyl,
(6) —C$_{1-6}$alkyl-(CH$_{2-5}$ cycloalkyl-O—),
(7) —C$_{1-6}$alkyl-O—C$_{1-6}$alkyl,
(8) —C$_{1-6}$alkyl-C≡CH,
(9) —C$_{1-6}$alkyl-C$_{1-6}$alkyl, and
(10) phenyl;
each of R$^7$ and R$^8$ is independently selected from the group consisting of:
(1) hydrogen, and
(2) C$_{1-6}$alkyl,
or R$_7$ and R$^8$ taken together form a keto group;
or a pharmaceutically acceptable salt thereof;
with the proviso that the compound is other than:
6-(2-methyl-3-oxoisoindolin-5-yl)-5-(1-((1-methylcyclopentyl)methyl)-1H-pyrazol-4-yl)picolinonitrile.

2. The compound of claim 1, or a pharmaceutically acceptable salt thereof, wherein X is N.

3. The compound of claim 1, or a pharmaceutically acceptable salt thereof, wherein X is CH.

4. The compound of claim 1, or a pharmaceutically acceptable salt thereof, wherein R$^1$ is selected from the group consisting of:
(1) hydrogen,
(2) fluoro,
(3) chloro,
(4) —CN, and
(5) methyl.

5. The compound of claim 1, or a pharmaceutically acceptable salt thereof, wherein R$^2$ is selected from the group consisting of:
(1) hydrogen, and
(2) methyl.

6. The compound of claim 1, or a pharmaceutically acceptable salt thereof, wherein R$^1$ and R$^2$ are joined together with a —(CH$_2$)$_3$— to form a 5-membered ring, which is unsubstituted or substituted with a hydroxy, or 1-3 fluoro.

7. The compound of claim 1, or a pharmaceutically acceptable salt thereof, wherein R$^3$ is selected from the group consisting of:
(1) hydrogen,
(2) —CN, and
(2) methyl.

8. The compound of claim 1, or a pharmaceutically acceptable salt thereof, wherein R$^6$ is selected from the group consisting of:
(1) hydrogen,
(2) —C$_{1-6}$alkyl, which is unsubstituted or substituted with a —CN, 1-3 fluoro, or phenyl which is unsubstituted or substituted with a hydroxy or a —SO$_2$—NH$_2$, and
(3) —C$_{1-6}$alkyl-C$_{3-6}$cycloalkyl.

9. The compound of claim 1, or a pharmaceutically acceptable salt thereof, wherein R$^7$ is hydrogen and R$^8$ is hydrogen.

10. A compound which is selected from the group consisting of:
3-(6-fluoro-5-methyl-3-(1-((1-methylcyclopentyl)methyl)-1H-pyrazol-4-yl)pyridin-2-yl)-6-methyl-6,7-dihydro-5H-pyrrolo[3,4-b]pyridin-5-one;
(R)-6-(cyclopropylmethyl)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
(S)-6-(cyclopropylmethyl)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
6-(3-(1-(cyclopentylmethyl)-1H-pyrazol-4-yl)-6-methylpyridin-2-yl)-2-(cyclopropylmethyl)-isoindolin-1-one;
6-(3-(1-(cyclopentylmethyl)-1H-pyrazol-4-yl)-6-methylpyridin-2-yl)-2-phenethylisoindolin-1-one;
6-(3-(1-(cyclopentylmethyl)-1H-pyrazol-4-yl)-6-methylpyridin-2-yl)-2-((tetrahydrofuran-2-yl)methyl)isoindolin-1-one;
6-(3-(1-(cyclopentylmethyl)-1H-pyrazol-4-yl)-6-methylpyridin-2-yl)-2-cyclopropylisoindolin-1-one;
6-(3-(1-(cyclopentylmethyl)-1H-pyrazol-4-yl)-4-fluoropyridin-2-yl)-2-(cyclopropylmethyl)-isoindolin-1-one;
6-(3-(1-(cyclopentylmethyl)-5-fluoro-1H-pyrazol-4-yl)pyridin-2-yl)-2-(cyclopropylmethyl)-isoindolin-1-one;
6-(3-(1-(cyclopentylmethyl)-5-fluoro-1H-pyrazol-4-yl)-6-methylpyridin-2-yl)-2-(cyclopropylmethyl)isoindolin-1-one;
6-(cyclopropylmethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
5-(1-(cyclopentylmethyl)-1H-pyrazol-4-yl)-6-(2-methyl-3-oxoisoindolin-5-yl)picolinonitrile;
5-(1-(cyclopentylmethyl)-1H-pyrazol-4-yl)-6-(2-(cyclopropylmethyl)-3-oxoisoindolin-5-yl)-N-methylpicolinamide    5-(1-(cyclopentylmethyl)-1H-pyrazol-4-yl)-6-(2-cyclopropyl-3-oxoisoindolin-5-yl)-N-methylpicolinamide    5-(1-(cyclopentylmethyl)-1H-pyrazol-4-yl)-N-methyl-6-(2-methyl-3-oxoisoindolin-5-yl)picolinamide    5-(1-(cyclopentylmethyl)-1H-pyrazol-4-yl)-6-(2-(cyclopropylmethyl)-3-oxoisoindolin-5-yl)picolinamide    5-(1-(cyclopentylmethyl)-1H-pyrazol-4-yl)-6-(2-cyclopropyl-3-oxoisoindolin-5-yl)picolinamide    5-(1-(cyclopentylmethyl)-1H-pyrazol-4-yl)-6-(2-methyl-3-oxoisoindolin-5-yl)picolinamide    5-(1-(cyclopentylmethyl)-1H-pyrazol-4-yl)-6-(2-(cyclopropylmethyl)-3-oxoisoindolin-5-yl)picolinonitrile;
5-(1-(cyclopentylmethyl)-1H-pyrazol-4-yl)-6-(2-cyclopropyl-3-oxoisoindolin-5-yl)picolinonitrile;
5-(1-(cyclopentylmethyl)-1H-pyrazol-4-yl)-6-(3-oxoisoindolin-5-yl)picolinonitrile;
6-(3-(1-(cyclopentylmethyl)-1H-pyrazol-4-yl)-6-fluoropyridin-2-yl)-2-(cyclopropylmethyl)isoindolin-1-one;
6-(3-(1-(cyclopentylmethyl)-1H-pyrazol-4-yl)-6-fluoropyridin-2-yl)-2-methylisoindolin-1-one;
6-(3-(1-(cyclopentylmethyl)-1H-pyrazol-4-yl)-6-fluoropyridin-2-yl)-2-cyclopropylisoindolin-1-one;
6-(3-(1-((1-methylcyclopentyl)methyl)-1H-pyrazol-4-yl)pyridin-2-yl)isoindolin-1-one;
2-methyl-6-(3-(1-((1-methylcyclopentyl)methyl)-1H-pyrazol-4-yl)pyridin-2-yl)isoindolin-1-one;
2-cyclopropyl-6-(3-(1-((1-methylcyclopentyl)methyl)-1H-pyrazol-4-yl)pyridin-2-yl)isoindolin-1-one;
2-methyl-6-(6-methyl-3-(1-((1-methylcyclopentyl)methyl)-1H-pyrazol-4-yl)pyridin-2-yl)isoindolin-1-one;
2-cyclopropyl-6-(6-methyl-3-(1-((1-methylcyclopentyl)methyl)-1H-pyrazol-4-yl)pyridin-2-yl)isoindolin-1-one;
2-(cyclopropylmethyl)-6-(4-fluoro-3-(1-((1-methylcyclopentyl)methyl)-1H-pyrazol-4-yl)pyridin-2-yl)isoindolin-1-one;
2-(cyclopropylmethyl)-6-(3-(5-fluoro-1-((1-methylcyclopentyl)methyl)-1H-pyrazol-4-yl)-6-methylpyridin-2-yl)isoindolin-1-one;

2-(2-methyl-3-oxoisoindolin-5-yl)-3-(1-((1-methylcyclopentyl)methyl)-1H-pyrazol-4-yl)isonicotinonitrile;
6-(2-(cyclopropylmethyl)-3-oxoisoindolin-5-yl)-5-(1-((1-methylcyclopentyl)methyl)-1H-pyrazol-4-yl)picolinonitrile;
6-(2-cyclopropyl-3-oxoisoindolin-5-yl)-5-(1-((1-methylcyclopentyl)methyl)-1H-pyrazol-4-yl)picolinonitrile;
5-(1-((1-methylcyclopentyl)methyl)-1H-pyrazol-4-yl)-6-(3-oxoisoindolin-5-yl)picolinonitrile;
methyl 2-(6-(6-cyano-3-(1-((1-methylcyclopentyl)methyl)-1H-pyrazol-4-yl)pyridin-2-yl)-1-oxoisoindolin-2-yl)acetate;
2-cyclopropyl-6-(6-fluoro-3-(1-((1-methylcyclopentyl)methyl)-1H-pyrazol-4-yl)pyridin-2-yl)isoindolin-1-one;
6-(6-fluoro-3-(1-((1-methylcyclopentyl)methyl)-1H-pyrazol-4-yl)pyridin-2-yl)-2-methylisoindolin-1-one;
6-(6-fluoro-3-(1-((1-methylcyclopentyl)methyl)-1H-pyrazol-4-yl)pyridin-2-yl)isoindolin-1-one;
6-(6-chloro-5-methyl-3-(1-((1-methylcyclopentyl)methyl)-1H-pyrazol-4-yl)pyridin-2-yl)-2-methylisoindolin-1-one;
2-methyl-6-(3-(1-((1-methylcyclopentyl)methyl)-1H-pyrazol-4-yl)-6,7-dihydro-5H-cyclopenta[b]pyridin-2-yl)isoindolin-1-one;
(R)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
(S)-3-(7-fluoro-3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
6-(6-chloro-5-methyl-3-(1-((1-methylcyclopentyl)methyl)-1H-pyrazol-4-yl)pyridin-2-yl)isoindolin-1-one;
6-(5-fluoro-6-(hydroxymethyl)-3-(1-((1-methylcyclopentyl)methyl)-1H-pyrazol-4-yl)pyridin-2-yl)-2-methylisoindolin-1-one;
6-(2-(2-fluoroethyl)-3-oxoisoindolin-5-yl)-5-(1-((1-methylcyclopentyl)methyl)-1H-pyrazol-4-yl)picolinonitrile;
5-(5-fluoro-1-((1-methylcyclopentyl)methyl)-1H-pyrazol-4-yl)-6-(2-methyl-3-oxoisoindolin-5-yl)picolinonitrile;
5-(5-fluoro-1-((1-methylcyclopentyl)methyl)-1H-pyrazol-4-yl)-6-(3-oxoisoindolin-5-yl)picolinonitrile;
6-(2-cyclopropyl-3-oxoisoindolin-5-yl)-5-(5-fluoro-1-((1-methylcyclopentyl)methyl)-1H-pyrazol-4-yl)picolinonitrile;
6-(2-(cyclopropylmethyl)-3-oxoisoindolin-5-yl)-5-(5-fluoro-1-((1-methylcyclopentyl)methyl)-1H-pyrazol-4-yl)picolinonitrile;
6-(5,6-difluoro-3-(1-((1-methylcyclopentyl)methyl)-1H-pyrazol-4-yl)pyridin-2-yl)-2-methylisoindolin-1-one;
3-fluoro-6-(2-methyl-3-oxoisoindolin-5-yl)-5-(1-((1-methylcyclopentyl)methyl)-1H-pyrazol-4-yl)picolinonitrile;
6-(2-(cyclopropylmethyl)-3-oxoisoindolin-5-yl)-3-fluoro-5-(1-((1-methylcyclopentyl)methyl)-1H-pyrazol-4-yl)picolinonitrile;
2-(2-fluoroethyl)-6-(3-(1-((1-methylcyclopentyl)methyl)-1H-pyrazol-4-yl)-6,7-dihydro-5H-cyclopenta[b]pyridin-2-yl)isoindolin-1-one;
6-(5-fluoro-3-(1-((1-methylcyclopentyl)methyl)-1H-pyrazol-4-yl)pyridin-2-yl)-2-methylisoindolin-1-one;
3-amino-6-(2-methyl-3-oxoisoindolin-5-yl)-5-(1-((1-methylcyclopentyl)methyl)-1H-pyrazol-4-yl)picolinonitrile;
6-(6-(fluoromethyl)-3-(1-((1-methylcyclopentyl)methyl)-1H-pyrazol-4-yl)pyridin-2-yl)-2-methylisoindolin-1-one;
6-(6-fluoro-5-methyl-3-(1-((1-methylcyclopentyl)methyl)-1H-pyrazol-4-yl)pyridin-2-yl)-2-methylisoindolin-1-one;
5-(5-fluoro-1-((1-methylcyclopentyl)methyl)-1H-pyrazol-4-yl)-6-(6-methyl-5-oxo-6,7-dihydro-5H-pyrrolo[3,4-b]pyridin-3-yl)picolinonitrile;
6-(3-(1-((1-methylcyclopentyl)methyl)-1H-pyrazol-4-yl)-6,7-dihydro-5H-cyclopenta[b]pyridin-2-yl)isoindolin-1-one;
3-(6-(3-(1-((1-methylcyclopentyl)methyl)-1H-pyrazol-4-yl)-6,7-dihydro-5H-cyclopenta[b]pyridin-2-yl)-1-oxoisoindolin-2-yl)propanenitrile;
6-(6-fluoro-3-(5-fluoro-1-((1-methylcyclopentyl)methyl)-1H-pyrazol-4-yl)pyridin-2-yl)-2-methylisoindolin-1-one;
3-(6-(fluoromethyl)-3-(1-((1-methylcyclopentyl)methyl)-1H-pyrazol-4-yl)pyridin-2-yl)-6-methyl-6,7-dihydro-5H-pyrrolo[3,4-b]pyridin-5-one;
3-(6-fluoro-3-(5-fluoro-1-((1-methylcyclopentyl)methyl)-1H-pyrazol-4-yl)pyridin-2-yl)-6-methyl-6,7-dihydro-5H-pyrrolo[3,4-b]pyridin-5-one;
5-(1-((1-methylcyclopentyl)methyl)-1H-pyrazol-4-yl)-6-(1,1,2-trimethyl-3-oxoisoindolin-5-yl)picolinonitrile;
6-methyl-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
6-(4-amino-6-methyl-3-(1-((1-methylcyclopentyl)methyl)-1H-pyrazol-4-yl)pyridin-2-yl)-2-methylisoindolin-1-one;
6-(4-amino-6-chloro-3-(1-((1-methylcyclopentyl)methyl)-1H-pyrazol-4-yl)pyridin-2-yl)-2-methylisoindolin-1-one;
6-(1,1-dimethyl-3-oxoisoindolin-5-yl)-5-(1-((1-methylcyclopentyl)methyl)-1H-pyrazol-4-yl)picolinonitrile;
2-(cyclopropylmethyl)-6-(6-methyl-3-(1-((1-methylcyclopentyl)methyl)-1H-pyrazol-4-yl)pyridin-2-yl)isoindolin-1-one;
6-(2-fluoroethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
3-(3-(5-fluoro-1-((1-methylcyclopentyl)methyl)-1H-pyrazol-4-yl)-6-(fluoromethyl)pyridin-2-yl)-6-methyl-6,7-dihydro-5H-pyrrolo[3,4-b]pyridin-5-one;
6-(3-(5-fluoro-1-((1-methylcyclopentyl)methyl)-1H-pyrazol-4-yl)-6-(fluoromethyl)pyridin-2-yl)-2-methylisoindolin-1-one;
3-(3-(3-(1-((1-methylcyclopentyl)methyl)-1H-pyrazol-4-yl)-6,7-dihydro-5H-cyclopenta[b]pyridin-2-yl)-5-oxo-5,7-dihydro-6H-pyrrolo[3,4-b]pyridin-6-yl)propanenitrile;
6-(2-methoxyethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
6,7,7-trimethyl-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;
5-(1-((1-methylcyclopentyl)methyl)-1H-pyrazol-4-yl)-6-(1,1,2-trimethyl-3-oxoisoindolin-5-yl)picolinonitrile;
2-(2-methoxyethyl)-6-(3-(1-((1-methylcyclopentyl)methyl)-1H-pyrazol-4-yl)-6,7-dihydro-5H-cyclopenta[b]pyridin-2-yl)isoindolin-1-one;

3-(3-(5-fluoro-1-((1-methylcyclopentyl)methyl)-1H-pyrazol-4-yl)-6,7-dihydro-5H-cyclopenta[b]pyridin-2-yl)-6-methyl-6,7-dihydro-5H-pyrrolo[3,4-b]pyridin-5-one;

6-(6-chloro-3-(5-fluoro-1-((1-methylcyclopentyl)methyl)-1H-pyrazol-4-yl)-5-methylpyridin-2-yl)-2-methylisoindolin-1-one;

6-(3-(1-(cyclopentylmethyl)-5-fluoro-1H-pyrazol-4-yl)-6-methylpyridin-2-yl)-2-methylisoindolin-1-one;

6-(6-(hydroxymethyl)-5-methyl-3-(1-((1-methylcyclopentyl)methyl)-1H-pyrazol-4-yl)pyridin-2-yl)-2-methylisoindolin-1-one;

3-chloro-6-(2-methyl-3-oxoisoindolin-5-yl)-5-(1-((1-methylcyclopentyl)methyl)-1H-pyrazol-4-yl)picolinonitrile;

5-(5-chloro-1-((1-methylcyclopentyl)methyl)-1H-pyrazol-4-yl)-6-(2-methyl-3-oxoisoindolin-5-yl)picolinonitrile;

3-(6-(difluoromethyl)-3-(1-((1-methylcyclopentyl)methyl)-1H-pyrazol-4-yl)pyridin-2-yl)-6-methyl-6,7-dihydro-5H-pyrrolo[3,4-b]pyridin-5-one;

6-methyl-3-(3-(1-((1-methylcyclopentyl)methyl)-1H-pyrazol-4-yl)-6-(trifluoromethyl)pyridin-2-yl)-6,7-dihydro-5H-pyrrolo[3,4-b]pyridin-5-one;

5-(1-((1-methylcyclopentyl)methyl)-1H-pyrazol-4-yl)-6-(2-(oxetan-3-yl)-3-oxoisoindolin-5-yl)picolinonitrile;

6-(3-(1-(cyclopentylmethyl)-1H-pyrazol-4-yl)pyridin-2-yl)-2-phenylisoindolin-1-one;

6-(3-(1-(cyclopentylmethyl)-1H-pyrazol-4-yl)pyridin-2-yl)-2-(cyclopropylmethyl)isoindolin-1-one;

6-(3-(1-(cyclopentylmethyl)-1H-pyrazol-4-yl)pyridin-2-yl)-2-((tetrahydrofuran-2-yl)methyl)isoindolin-1-one;

2-(cyclobutylmethyl)-6-(3-(1-(cyclopentylmethyl)-1H-pyrazol-4-yl)pyridin-2-yl)isoindolin-1-one;

1-(6-(3-(1-(cyclopentylmethyl)-1H-pyrazol-4-yl)pyridin-2-yl)-1-oxoisoindolin-2-yl)cyclopropane-1-carbonitrile;

6-(3-(1-(cyclopentylmethyl)-1H-pyrazol-4-yl)pyridin-2-yl)-2-(oxetan-3-yl)isoindolin-1-one;

2-cyclobutyl-6-(3-(1-(cyclopentylmethyl)-1H-pyrazol-4-yl)pyridin-2-yl)isoindolin-1-one;

1-(6-(3-(1-(cyclopentylmethyl)-1H-pyrazol-4-yl)pyridin-2-yl)-1-oxoisoindolin-2-yl)-N-methylcyclopropane-1-carboxamide 4-(2-(6-(3-(1-(cyclopentylmethyl)-1H-pyrazol-4-yl)pyridin-2-yl)-1-oxoisoindolin-2-yl)ethyl)benzenesulfonamide 6-(3-(1-(cyclopentylmethyl)-1H-pyrazol-4-yl)pyridin-2-yl)-2-phenethylisoindolin-1-one;

6-(3-(1-(cyclopentyl-methyl)-1H-pyrazol-4-yl)pyridin-2-yl)-2-cyclopropylisoindolin-1-one;

6-(3-(1-(cyclopentylmethyl)-1H-pyrazol-4-yl)pyridin-2-yl)-2-(4-hydroxyphenethyl)isoindolin-1-one;

6-(6-Methyl-5-oxo-6,7-dihydro-5H-pyrrolo[3,4-b]pyridin-3-yl)-5-(1-((1-methylcyclopentyl)methyl)-1H-pyrazol-4-yl)picolinonitrile;

6-(3-(1-(cyclopentylmethyl)-1H-pyrazol-4-yl)pyridin-2-yl)-2-methylisoindolin-1-one;

6-(3-(1-(cyclopentylmethyl)-1H-pyrazol-4-yl)-6-methylpyridin-2-yl)-2-methylisoindolin-1-one;

2-methyl-5-(6-methyl-3-(1 #1-methylcyclopentyl)methyl)-1H-pyrazol-4-yl)pyridin-2-yl)isoindoline-1,3-dione;

5-(6-methyl-3-(1-((1-methylcyclopentyl)methyl)-1H-pyrazol-4-yl)pyridin-2-yl)isoindoline-1,3-dione;

3-(6-chloro-5-methyl-3-(1-((1-methylcyclopentyl)methyl)-1H-pyrazol-4-yl)pyridin-2-yl)-6-methyl-6,7-dihydro-5H-pyrrolo[3,4-b]pyridin-5-one;

5-(1-((1-methylcyclopentyl)methyl)-1H-pyrazol-4-yl)-6-(5-oxo-6,7-dihydro-5H-pyrrolo[3,4-b]pyridin-3-yl)picolinonitrile;

6-(6-(cyclopropylmethyl)-5-oxo-6,7-dihydro-5H-pyrrolo[3,4-b]pyridin-3-yl)-5-(1-((1-methylcyclopentyl)methyl)-1H-pyrazol-4-yl)picolinonitrile;

6-(6-(2-fluoroethyl)-5-oxo-6,7-dihydro-5H-pyrrolo[3,4-b]pyridin-3-yl)-5-(1-((1-methylcyclopentyl)methyl)-1H-pyrazol-4-yl)picolinonitrile;

6-(6-methyl-3-(1-((1-methylcyclopentyl)methyl)-1H-pyrazol-4-yl)pyridin-2-yl)isoindolin-1-one;

6-(6-cyclopropyl-5-oxo-6,7-dihydro-5H-pyrrolo[3,4-b]pyridin-3-yl)-5-(1-((1-methylcyclopentyl)methyl)-1H-pyrazol-4-yl)picolinonitrile;

3-(6-chloro-3-(1-((1-methylcyclopentyl)methyl)-1H-pyrazol-4-yl)pyridin-2-yl)-6-(cyclopropylmethyl)-6,7-dihydro-5H-pyrrolo [3,4-b]pyridin-5-one;

6-(6-chloro-3-(1-(cyclopentylmethyl)-1H-pyrazol-4-yl)pyridin-2-yl)-2-methylisoindolin-1-one;

6-(6-chloro-3-(1-(cyclopentylmethyl)-1H-pyrazol-4-yl)pyridin-2-yl)-2-cyclopropylisoindolin-1-one;

6-(5,6-dimethyl-3-(1-((1-methylcyclopentyl)methyl)-1H-pyrazol-4-yl)pyridin-2-yl)-2-methylisoindolin-1-one;

5-(3-cyano-1-((1-methylcyclopentyl)methyl)-1H-pyrazol-4-yl)-6-(2-methyl-3-oxoisoindolin-5-yl)picolinonitrile;

3-methyl-6-(2-methyl-3-oxoisoindolin-5-yl)-5-(1-((1-methylcyclopentyl)methyl)-1H-pyrazol-4-yl)picolinonitrile;

3-methyl-6-(6-methyl-5-oxo-6,7-dihydro-5H-pyrrolo[3,4-b]pyridin-3-yl)-5-(1-((1-methylcyclopentyl)methyl)-1H-pyrazol-4-yl)picolinonitrile;

3-methyl-5-(1-((1-methylcyclopentyl)methyl)-1H-pyrazol-4-yl)-6-(3-oxoisoindolin-5-yl)picolinonitrile;

3-methyl-6-(2-methyl-3-oxoisoindolin-5-yl)-5-(1-((1-methylcyclopentyl)methyl)-1H-pyrazol-4-yl)picolinamide 5-(1-((1-methylcyclopentyl)methyl)-1H-pyrazol-4-yl)-6-(3-oxoisoindolin-5-yl)picolinamide 6-(6-(fluoromethyl)-5-methyl-3-(14(1-methylcyclopentyl)methyl)-1H-pyrazol-4-yl)pyridin-2-yl)-2-methylisoindolin-1-one;

6-(5-fluoro-6-(fluoromethyl)-3-(1-((1-methylcyclo-pentyl)-methyl)-1H-pyrazol-4-yl)pyridin-2-yl)-2-methylisoindolin-1-one;

6-(6-(methoxymethyl)-5-methyl-3-(1-((1-methylcyclopentyl)methyl)-1H-pyrazol-4-yl)pyridin-2-yl)-2-methylisoindolin-1-one;

3-(6-(fluoromethyl)-3-(1-((1-methylcyclopentyl)methyl)-1H-pyrazol-4-yl)pyridin-2-yl)-6-(prop-2-yn-1-yl)-6,7-dihydro-5H-pyrrolo[3,4-b]pyridin-5-one;

3-(3-(1-((1-methylcyclopentyl)methyl)-1H-pyrazol-4-yl)-6,7-dihydro-5H-cyclopenta[b]pyridin-2-yl)-6-(prop-2-yn-1-yl)-6,7-dihydro-5H-pyrrolo[3,4-b]pyridin-5-one;

6-(2-fluoroethyl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;

6-(but-2-yn-1-yl)-3-(3-(1-((1-methylcyclopentyl)methyl)-1H-pyrazol-4-yl)-6,7-dihydro-5H-cyclopenta[b]pyridin-2-yl)-6,7-dihydro-5H-pyrrolo[3,4-b]pyridin-5-one;

5-(1-((1-methylcyclopentyl)methyl)-1H-pyrazol-4-yl)-6-(5-oxo-6-(prop-2-yn-1-yl)-6,7-dihydro-5H-pyrrolo[3,4-b]pyridin-3-yl)picolinonitrile;

5-(1-((1-methylcyclopentyl)methyl)-1H-pyrazol-4-yl)-6-(3-oxo-2-(prop-2-yn-1-yl)isoindolin-5-yl)picolinonitrile;

6-(6-isopropyl-5-oxo-6,7-dihydro-5H-pyrrolo[3,4-b]pyridin-3-yl)-5-(1-((1-methylcyclopentyl)methyl)-1H-pyrazol-4-yl)picolinonitrile;

6-(6-(but-2-yn-1-yl)-5-oxo-6,7-dihydro-5H-pyrrolo[3,4-b]pyridin-3-yl)-5-(1-((1-methylcyclopentyl)methyl)-1H-pyrazol-4-yl)picolinonitrile;

6-(3-(1-((1-methylcyclopentyl)methyl)-1H-pyrazol-4-yl)-6,7-dihydro-5H-cyclopenta[b]pyridin-2-yl)-2-(prop-2-yn-1-yl)isoindolin-1-one;

2-(2-methyl-3-oxoisoindolin-5-yl)-3-(1-((1-methylcyclopentyl)methyl)-1H-pyrazol-4-yl)-5,6-dihydro-7H-cyclopenta[b]pyridin-7-one;

3-chloro-6-(2-methyl-3-oxoisoindolin-5-yl)-5-(1-((1-methylcyclopentyl)methyl)-1H-pyrazol-4-yl)picolinonitrile;

6-(4-fluoro-6-methyl-3-(1-((1-methylcyclopentyl)methyl)-1H-pyrazol-4-yl)pyridin-2-yl)-2-methylisoindolin-1-one;

6-(5,6-difluoro-3-(1-((1-methylcyclopentyl)methyl)-1H-pyrazol-4-yl)pyridin-2-yl)-2-methylisoindolin-1-one; and 6-(cyclopropylmethyl)-3-(6-ethynyl-3-(1-((1-methylcyclopentyl)methyl)-1H-pyrazol-4-yl)pyridin-2-yl)-6,7-dihydro-5H-pyrrolo[3,4-b]pyridin-5-one;

or a pharmaceutically acceptable salt thereof.

11. A pharmaceutical composition which comprises an inert carrier and a compound of claim 1, or a pharmaceutically acceptable salt thereof.

* * * * *